US008022040B2

(12) United States Patent
Bertozzi et al.

(10) Patent No.: US 8,022,040 B2
(45) Date of Patent: Sep. 20, 2011

(54) HYDROXYAPATITE-BINDING PEPTIDES FOR BONE GROWTH AND INHIBITION

(75) Inventors: Carolyn R. Bertozzi, Berkeley, CA (US); Jie Song, Shrewsbury, MA (US); Seung-Wuk Lee, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 54 days.

(21) Appl. No.: 11/720,427

(22) PCT Filed: Nov. 29, 2005

(86) PCT No.: PCT/US2005/043214
§ 371 (c)(1),
(2), (4) Date: Apr. 22, 2008

(87) PCT Pub. No.: WO2006/062776
PCT Pub. Date: Jun. 15, 2006

(65) Prior Publication Data
US 2008/0279908 A1 Nov. 13, 2008

Related U.S. Application Data

(60) Provisional application No. 60/631,660, filed on Nov. 29, 2004.

(51) Int. Cl.
*A61K 38/08* (2006.01)
(52) U.S. Cl. ............... 514/21.6; 514/21.7; 514/21.8; 530/324; 423/308
(58) Field of Classification Search ............ 514/2, 21.6, 514/21.7, 21.8; 530/324; 423/308
See application file for complete search history.

(56) References Cited

U.S. PATENT DOCUMENTS

| 4,351,337 | A | * | 9/1982 | Sidman ......................... 424/425 |
| 4,774,091 | A | * | 9/1988 | Yamahira et al. .............. 424/426 |
| 5,023,082 | A | * | 6/1991 | Friedman et al. .............. 424/426 |
| 5,039,660 | A | * | 8/1991 | Leonard et al. ................ 424/499 |
| 5,171,574 | A | * | 12/1992 | Kuberasampath et al. ... 424/423 |
| 5,223,409 | A | | 6/1993 | Ladner et al. |
| 5,338,665 | A | | 8/1994 | Schatz et al. |
| 5,432,018 | A | | 7/1995 | Dower et al. |
| 5,461,034 | A | | 10/1995 | Rodan et al. |
| 5,498,530 | A | | 3/1996 | Schatz et al. |
| 5,519,115 | A | * | 5/1996 | Mapelli et al. ................. 530/324 |
| 5,556,744 | A | * | 9/1996 | Weiner et al. ..................... 435/5 |
| 5,733,731 | A | | 3/1998 | Schatz et al. |
| 5,817,480 | A | * | 10/1998 | Murry et al. .................. 435/69.1 |
| 5,922,545 | A | | 7/1999 | Mattheakis et al. |
| 6,479,460 | B1 | | 11/2002 | Bab et al. |
| 7,790,161 | B2 | * | 9/2010 | Shen et al. ................... 424/130.1 |
| 2003/0026805 | A1 | * | 2/2003 | Athwal et al. ................. 424/145.1 |
| 2004/0071718 | A1 | * | 4/2004 | Tsai ............................ 424/185.1 |
| 2004/0146892 | A1 | * | 7/2004 | Murphy et al. ..................... 435/6 |
| 2004/0161444 | A1 | | 8/2004 | Song et al. |
| 2004/0241801 | A1 | * | 12/2004 | Anderson et al. ............. 435/69.1 |
| 2007/0039070 | A1 | * | 2/2007 | Bloksberg et al. ............ 800/284 |

FOREIGN PATENT DOCUMENTS

| EP | 0471407 | * | 2/1992 |
| WO | W09640987 A1 | | 12/1996 |
| WO | W09815833 A1 | | 4/1998 |

OTHER PUBLICATIONS

Barany, George (Int. J. Peptide Protein Res 30, 705-739, 1987).*
Lloyd-Williams (Tetrahedron 49, 11065-11133, 1993).*
Abe Makoto, Bone 46(5), 1359-1368, 2010.*
Shapses S. A., Calcified Tissue International 73(1), 86-92, 2003.*
Leboy Phoebe S., Annals of the New York Academy of Sciences 1068, 14-18, 2006.*
Canalis Ernesto, Annals of the New York Academy of Sciences 1116, 50-58, 2007.*
Ramoya Anna, Endocrinology 149(9), 4374-81, 2008.*
Hsu, D. R., Molecular Cell 1:673-683, 1998.*
Addadi, Angew. Chem. Int. Ed. Engl. 31, 153 (1992).
Weiner, J. Mater. Chem. 7, 689 (1997).
He, Nat. Mater. 2. 552 (2003).
Tye, J Bio. Chem. 278, 7949 (2003).
Whaley, Nature 405, 665 (2000).
Lee, Science, 296, 892 (2002).
Mao, Science, 303, 213 (2004).
Reiss, Nano Lett., 4, 1127 (2004).
Scott, Science 249: 386 (1990).
Devlin, Science 249: 404 (1990).
Altschul, Nucleic Acids Res., 25: 3389-3402 (1997).
Bella, Science, 266, 75 (1994).
Hunter, Biochem. J., 302, 175 (1994).
George, J. Biol. Chem., 271, 32869 (1996).
Hartgerink, Science, 294, 1684 (2001).
McLafferty, Gene, 15, 29 (1993).
Lowman, H.B. 1997. Bacteriophage display and discovery of peptide leads for drug development. Annu. Rev. Biophys. Biomol. Struct. 26:401-424.

* cited by examiner

*Primary Examiner* — David Lukton
(74) *Attorney, Agent, or Firm* — Robin C. Chiang; Lawrence Berkeley National Laboratory

(57) ABSTRACT

Hydroxyapatite (HA)-binding peptides are selected using combinatorial phage library display. Pseudo-repetitive consensus amino acid sequences possessing periodic hydroxyl side chains in every two or three amino acid sequences are obtained. These sequences resemble the $(Gly-Pro-Hyp)_x$ repeat of human type I collagen, a major component of extracellular matrices of natural bone. A consistent presence of basic amino acid residues is also observed. The peptides are synthesized by the solid-phase synthetic method and then used for template-driven HA-mineralization. Microscopy reveal that the peptides template the growth of polycrystalline HA crystals ~40 nm in size.

54 Claims, 24 Drawing Sheets

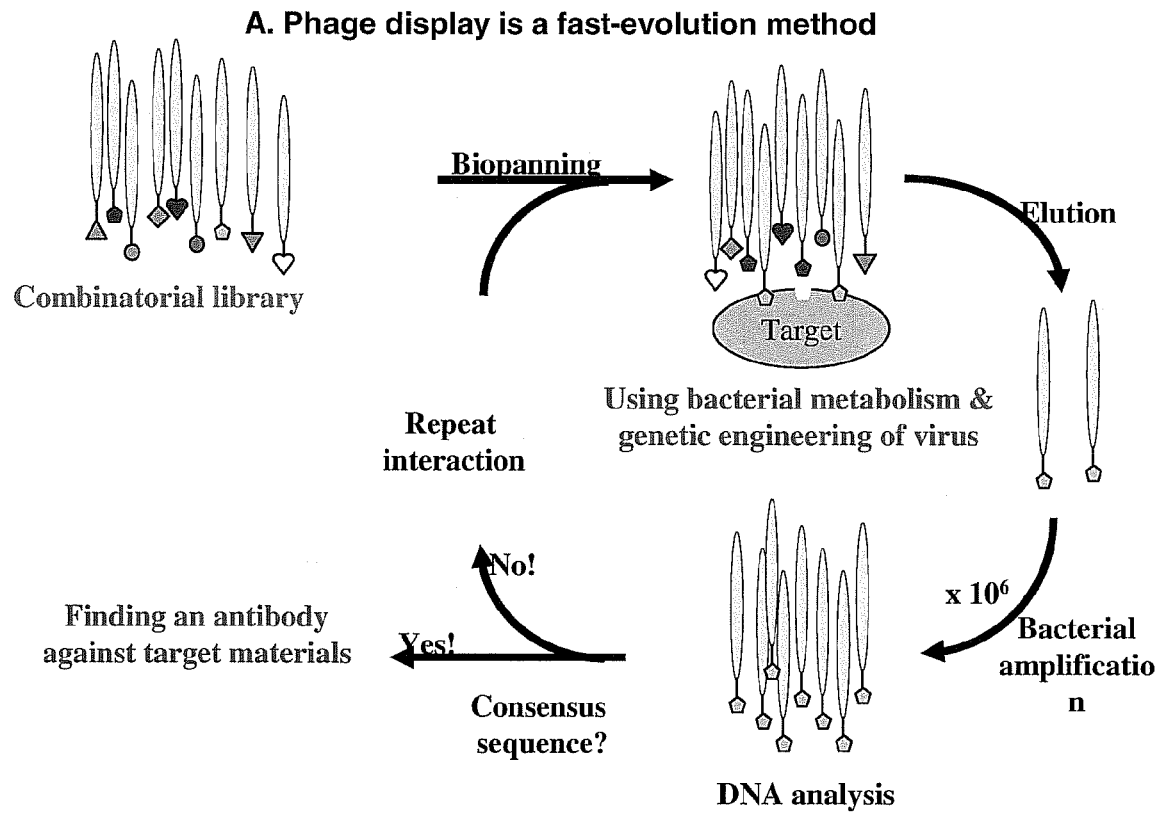
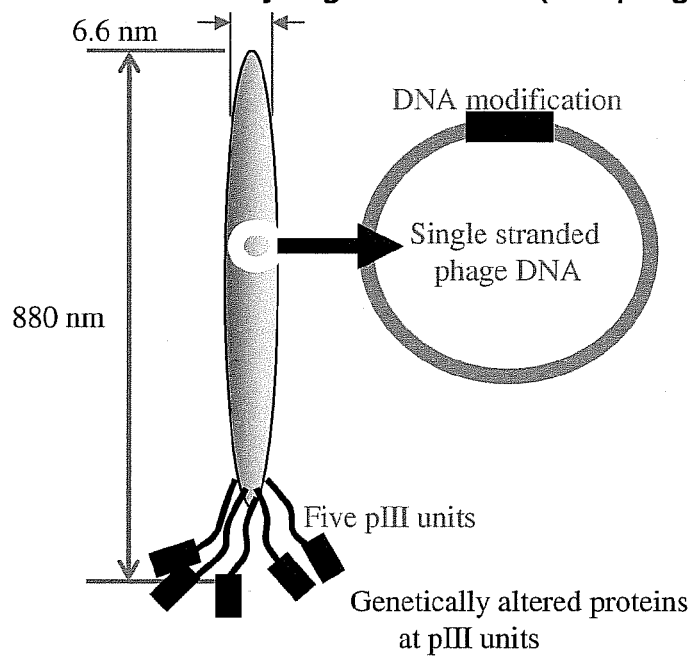
Fig. 1

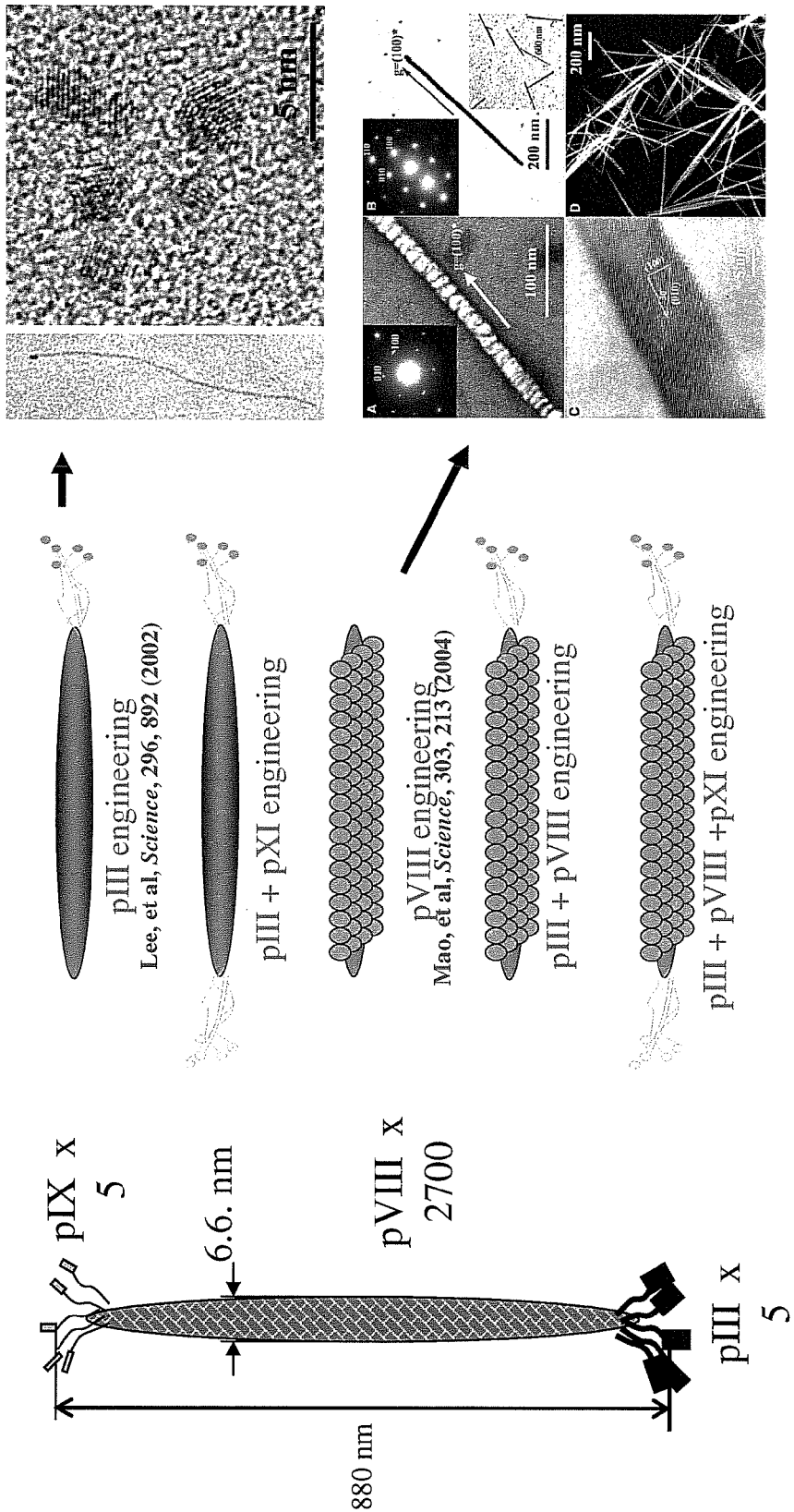
Fig. 2. Virus templated nanocrystal synthesis

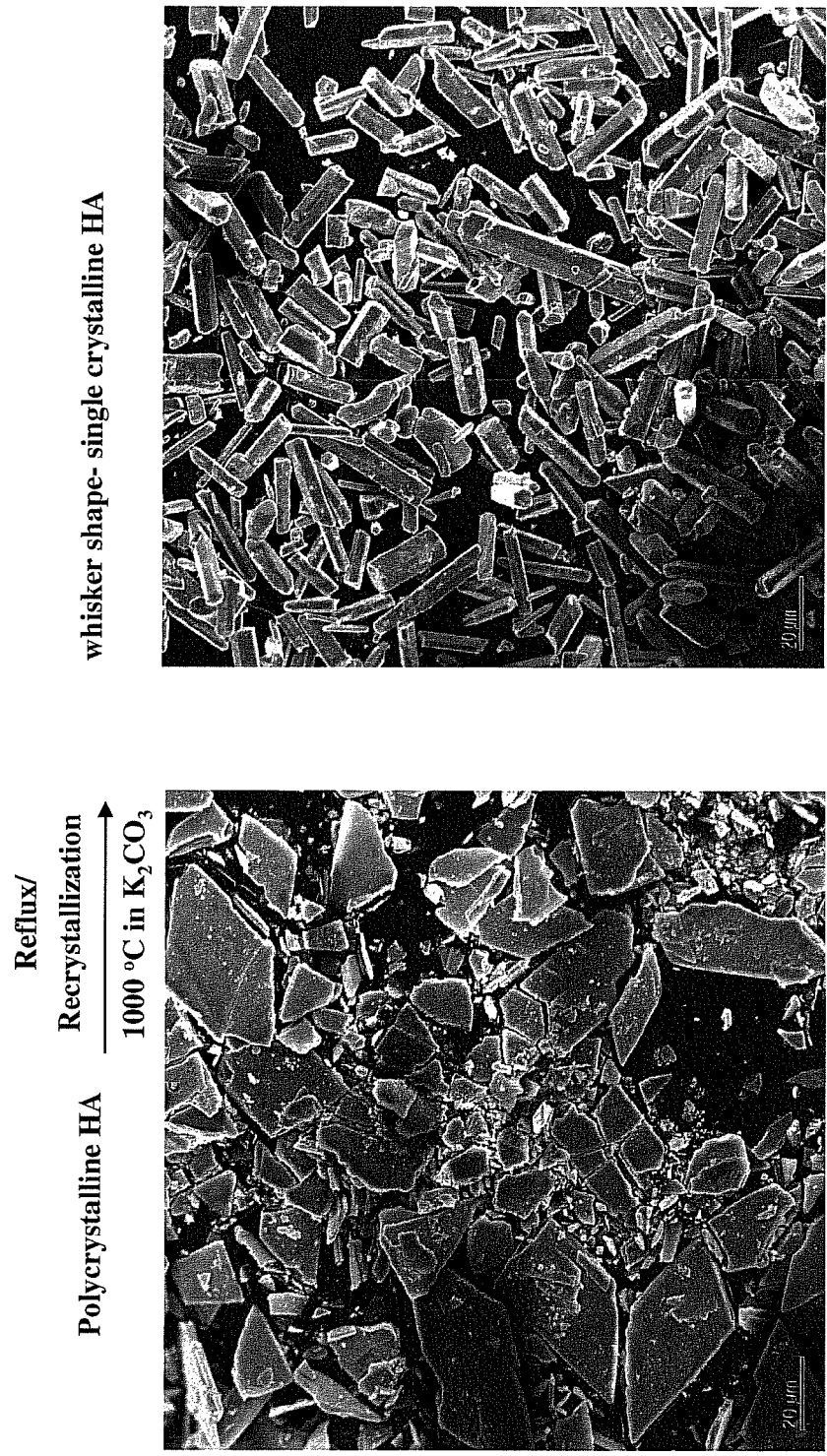
Fig. 3. Preparation of single crystal hydroxyapatite(HA)

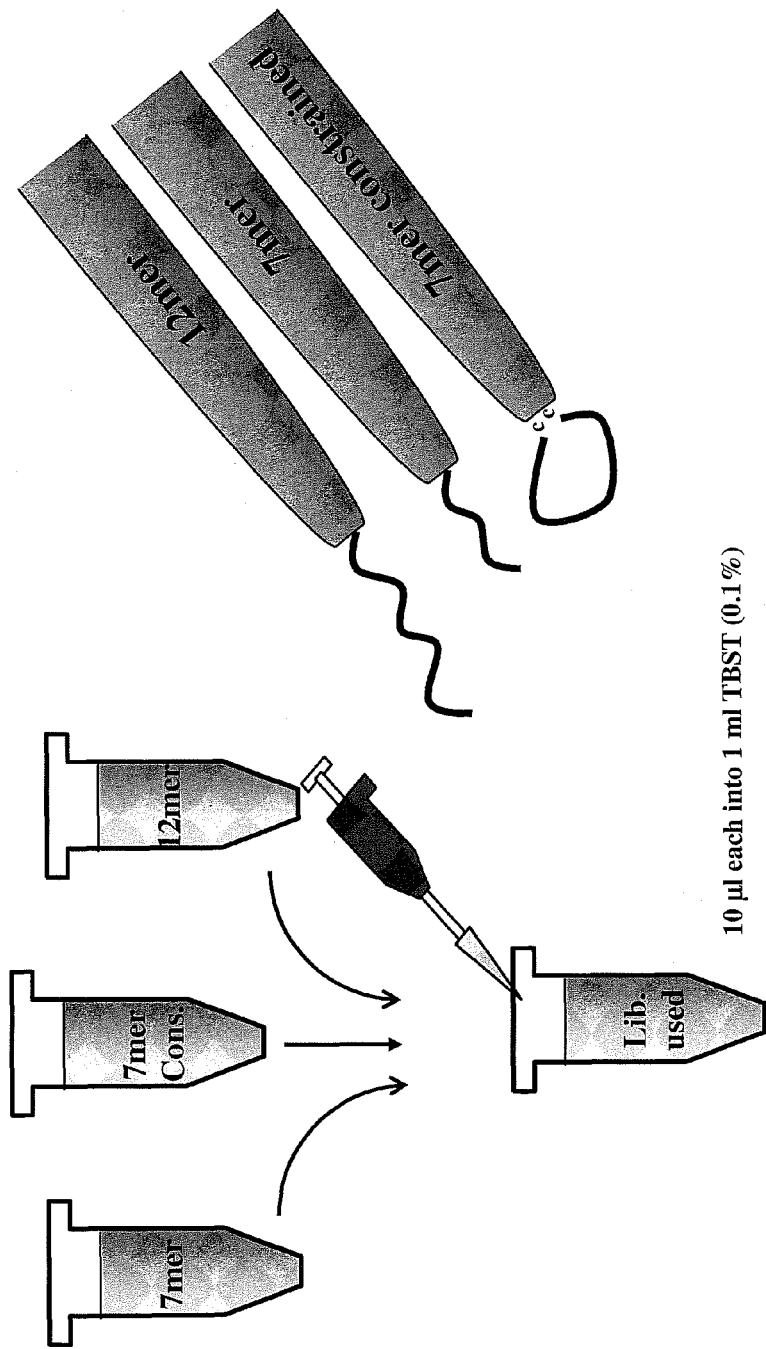
Fig. 4. M13 phage library used

Fig. 5. Characteristics of HA binding protein sequences

A. Single crystal HA (4th round)

| Sample | Pos 1 | Pos 2 | Pos 3 | Pos 4 | Pos 5 |

Fig. 6

7mer constrained

| | | Pos 1 | Pos 2 | Pos 3 | Pos 4 | Pos 5 | Pos 6 | Pos 7 | |
|---|---|---|---|---|---|---|---|---|---|
| 1 | W4a-4.25 | A | Ala | Ser | His | Asn | Pro | Lys | Leu | C |
| 2 | W4a-4.26 | A | Pro | Ala | Lys | Gln | Lys | Ala | His | C |
| 3 | W4a-4.33 | A | Pro | Ala | Tyr | Gln | Tyr | Ala | His | C |
| 4 | W4a-4.22 | A | Ser | Ala | Ser | Gly | Thr | Pro | Ser | C |
| 5 | W4a-4.16 | A | Thr | Arg | Phe | Tyr | Asp | Ser | Leu | C |
| 6 | W4a-4.20 | A | Gln | Asn | Pro | Arg | Gln | Ile | Tyr | C |
| 7 | W4a-4.21 | A | Gln | Asn | Pro | Arg | Gln | Ile | Tyr | C |
| 8 | W4a-4.39 | A | Gln | Asn | Pro | Arg | Gln | Ile | Lys | C |
| 9 | W4a-4.36 | A | Gln | Asn | Pro | Arg | Gln | Ile | Tyr | C |
| 10 | W4a-4.17 | A | Thr | Gly | Pro | Thr | Ser | Leu | Ser | C |
| 11 | W4a-4.37 | A | Thr | Gly | Pro | Thr | Ser | Leu | Ser | C |
| 12 | W4a-4.2 | A | Asn | Pro | Gln | Met | Gln | Arg | Ser | C |
| 13 | W4a-4.31 | A | Asn | Pro | Gln | Met | Gln | Arg | Ser | C |
| 14 | W4a-4.6 | A | Asn | Pro | Gln | Met | Gln | Arg | Ser | C |
| 15 | W4a-4.8 | A | Asn | Pro | Gln | Met | Gln | Arg | Ser | C |
| 16 | W4a-4.9 | A | Asn | Pro | Gln | Met | Gln | Arg | Ser | C |
| 17 | W4a-4.5 | A | Lys | Pro | Met | Gln | Phe | Val | His | C |
| 18 | W4a-4.7 | A | Ser | Ser | Tyr | Gly | Tyr | His | Ala | C |
| 19 | W4a-4.1 | A | Ser | Thr | Gln | Ala | His | Pro | Trp | C |
| 20 | W4a-4.10 | A | Gly | Ile | Ser | Arg | Leu | Phe | Ser | C |
| 21 | W4a-4.14 | A | Asn | Tyr | Pro | Thr | Leu | Lys | Ser | C |
| 22 | W4a-4.18 | A | Asn | Tyr | Pro | Thr | Leu | Lys | Ser | C |
| 23 | W4a-4.24 | A | Asn | Tyr | Pro | Thr | Leu | Lys | Ser | C |
| 24 | W4a-4.27 | A | Asn | Tyr | Pro | Thr | Leu | Lys | Ser | C |
| 25 | W4a-4.30 | A | Asn | Tyr | Pro | Thr | Leu | Lys | Ser | C |
| 26 | W4a-4.32 | A | Asn | Tyr | Pro | Thr | Leu | Lys | Ser | C |
| 27 | W4a-4.40 | A | Asn | Tyr | Pro | Tyr | Leu | Lys | Ser | C |

| Sample | Pos 1 | Pos 2 | Pos 3 | Pos 4 | Pos 5 | Pos 6 | Pos 7 |
|---|---|---|---|---|---|---|---|
| 1 W4a-4.12 | His | Ala | Pro | Val | Gln | Pro | Asn |

| Sample | Pos 1 | Pos 2 | Pos 3 | Pos 4 | Pos 5 | Pos 6 | Pos 7 | Pos 8 | Pos 9 | Pos 10 | Pos 11 | Pos 12 |
|---|---|---|---|---|---|---|---|---|---|---|---|---|
| 1 W4a-4.15 | Asn | Pro | Tyr | His | Pro | Thr | Ile | Pro | Gln | Ser | Val | His |
| 2 W4a-4.19 | Asn | Pro | Tyr | His | Pro | Thr | Ile | Pro | Gln | Ser | Val | His |
| 3 W4a-4.23 | Asn | Pro | Tyr | His | Pro | Thr | Ile | Pro | Gln | Ser | Val | His |
| 4 W4a-4.3 | Asn | Pro | Thr | His | Pro | Thr | Ile | Pro | Gln | Ser | Ile | His |
| 5 W4a-4.38 | His | Gln | Phe | Ile | Ser | Pro | Glu | Pro | Phe | Leu | Thr | Thr |
| 6 W4a-4.11 | Ser | Pro | Asn | Phe | Ser | Trp | Leu | Pro | Leu | Gly | Thr | Thr |
| 7 W4a-4.4 | Ser | Pro | Asn | Phe | Ser | Trp | Leu | Pro | Leu | Gly | Thr | Thr |
| 8 W4a-4.13 | Ser | Val | Ser | Val | Gly | Met | Lys | Pro | Ser | Pro | Arg | Pro |
| 9 W4a-4.34 | Ser | Val | Ser | Val | Gly | Met | Lys | Pro | Ser | Pro | Arg | Pro |
| 10 W4a-4.35 | Thr | Pro | Leu | Thr | Ser | Pro | Ser | Leu | Val | Arg | Pro | Gln |

| | Pos 1 | Pos 2 | Pos 3 | Pos 4 | Pos 5 | Pos 6 | Pos 7 |
|---|---|---|---|---|---|---|---|
| 1 W4A-1-10 | Ala | Asn | Pro | Pro | Leu | Ser | Leu |
| 2 W4A-1-9 | Ala | Lys | Gln | Thr | Val | Pro | Val |
| 3 W4A-1-15 | Ala | Thr | Phe | Ser | Pro | Leu | Leu |
| 4 W4A-1-5 | Asp | Gln | Tyr | Trp | Gly | Arg | Arg |
| 5 W4A-1-14 | Glu | Pro | Asn | His | Thr | Thr | Phe |
| 6 W4A-1-18 | His | Met | Leu | Ala | Gln | Leu | Phe |
| 7 W4A-1-12 | Ile | Gly | Tyr | Pro | Val | Leu | Pro |
| 8 W4A-1-31 | Lys | Leu | Ser | Ala | Trp | Ser | Phe |
| 9 W4A-1-11 | Lys | Tyr | Pro | Leu | Pro | Ala | Pro |
| 10 W4A-1-6 | Met | Thr | Leu | Pro | Thr | Ile | Arg |
| 11 W4A-1-16 | Phe | Met | Ala | Ala | Lys | Ser | Ser |
| 12 W4A-1-1 | Ser | Met | Tyr | Asp | Thr | His | Ser |
| 13 W4A-1-32 | Ser | Thr | Leu | Ala | Ser | Met | Arg |
| 14 W4A-1-23 | Ser | Leu | Met | Thr | Thr | Pro | Pro |
| 15 W4A-1-13 | Trp | Leu | Pro | Pro | Arg | Thr | Gln |

| | Pos 1 | Pos 2 | Pos 3 | Pos 4 | Pos 5 | Pos 6 | Pos 7 |
|---|---|---|---|---|---|---|---|
| 1 W4A-1-22 | A | C | Arg | Pro | His | Thr | Ile | Thr | Asn |
| 2 W4A-1-17 | A | C | Gln | Ser | Ser | Tyr | Asn | Pro | Ile |
| 3 W4A-1-25 | A | C | Gln | Thr | His | Ala | Arg | His | Gln |
| 4 W4A-1-21 | A | C | Glu | Thr | Arg | Thr | Gln | Leu | Leu |
| 5 W4A-1-29 | A | C | His | His | Gln | Ser | Ser | Pro | Ala |
| 6 W4A-1-20 | A | C | Leu | Gln | Lys | Ser | Pro | Ser | Leu |
| 7 W4A-1-4 | A | C | Pro | Pro | Lys | Asn | Ser | Arg | Gly |
| 8 W4A-1-19 | A | C | Ser | Ala | Lys | Lys | Ser | Phe | Ser |
| 9 W4A-1-24 | A | C | Ser | Gln | His | Ser | Thr | Gln | Asp |
| 10 W4A-1-27 | A | C | Thr | Ile | His | Thr | Lys | Pro | Ala |
| 11 W4A-1-8 | A | C | Thr | Lys | Asp | Pro | Leu | Pro | Ser |

| | Pos 1 | Pos 2 | Pos 3 | Pos 4 | Pos 5 | Pos 6 | Pos 7 | Pos 8 | Pos 9 | Pos 10 | Pos 11 | Pos 12 |
|---|---|---|---|---|---|---|---|---|---|---|---|---|
| 1 W4A-1-2 | Arg | Thr | Pro | Leu | Gln | Pro | Leu | Glu | Asp | Phe | Arg | Pro |
| 2 W4A-1-7 | Asn | Thr | Thr | Thr | Asp | Thr | Pro | Ser | Pro | Ser | Gln | Phe |
| 3 W4A-1-3 | Thr | Leu | Asp | Lys | Tyr | His | Arg | Leu | Leu | Ser | Arg | Tyr |
| 4 W4A-1-28 | Tyr | Pro | Ile | Met | Ser | His | Thr | Cys | Cys | His | Gly | Val |

Fig. 7

| 7mer constrained | | Pos 1 | Pos 2 | Pos 3 | Pos 4 | Pos 5 | Pos 6 | Pos 7 | |
|---|---|---|---|---|---|---|---|---|---|
| 1 | W4A-2-19 | A | Arg | His | Thr | Leu | Pro | Leu | His | C |
| 2 | W4A-2-18 | A | Asn | Phe | Ala | Met | Asn | Leu | Arg | C |
| 3 | W4A-2-29 | A | Asn | Phe | Ala | Met | Asn | Leu | Arg | C |
| 4 | W4A-2-15 | A | Asn | Pro | Gln | Met | Gln | Arg | Ser | C |
| 5 | W4A-2-24 | A | Asn | Pro | Gln | Met | Gln | Arg | Ser | C |
| 6 | W4A-2-32 | A | Asn | Pro | Gln | Met | Gln | Lys | Ser | C |
| 7 | W4A-2-13 | A | Asn | Tyr | Pro | Thr | Leu | Lys | Ser | C |
| 8 | W4A-2-27 | A | Asn | Tyr | Pro | Thr | Leu | Ile | Tyr | C |
| 9 | W4A-2-11 | A | Gln | Asn | Pro | Arg | Gln | Ile | Tyr | C |
| 10 | W4A-2-20 | A | Gln | Asn | Pro | Arg | Gln | Ile | Tyr | C |
| 11 | W4A-2-3 | A | Gln | Asn | Pro | Arg | Gln | Ile | Leu | C |
| 12 | W4A-2-6 | A | Gln | Asn | Pro | Arg | Gln | Pro | Ser | C |
| 13 | W4A-2-22 | A | Glu | Thr | Tyr | Ala | Arg | Ser | His | C |
| 14 | W4A-2-25 | A | Glu | Thr | Val | Cys | Ala | Val | His | C |
| 15 | W4A-2-14 | A | Lys | Pro | Met | Gln | Phe | Val | Leu | C |
| 16 | W4A-2-23 | A | Lys | Pro | Met | Gln | Phe | Ala | Leu | C |
| 17 | W4A-2-2 | A | Pro | Ala | Lys | Gln | Lys | Pro | Ser | C |
| 18 | W4A-2-26 | A | Pro | Thr | Thr | Trp | Gly | His | Ala | C |
| 19 | W4A-2-4 | A | Pro | Thr | Thr | Trp | Gly | His | Ala | C |
| 20 | W4A-2-7 | A | Ser | Ala | Ser | Gly | Thr | Pro | Trp | C |
| 21 | W4A-2-17 | A | Ser | Ser | Tyr | Glu | Tyr | His | Ala | C |
| 22 | W4A-2-9 | A | Ser | Ser | Thr | Glu | Tyr | His | Pro | C |
| 23 | W4A-2-30 | A | Ser | Thr | Gln | Ala | His | Pro | Ala | C |
| 24 | W4A-2-21 | A | Thr | Val | Leu | Gly | Thr | Phe | Ala | C |
| 25 | W4A-2-8 | A | Trp | Tyr | Pro | Asn | His | Leu | Ala | C |

| 7mer | | Pos 1 | Pos 2 | Pos 3 | Pos 4 | Pos 5 | Pos 6 | Pos 7 |
|---|---|---|---|---|---|---|---|---|
| 1 | W4A-2-1 | Thr | Thr | Tyr | Asn | Ser | Pro | Pro |
| 2 | W4A-2-5 | Met | Thr | Ser | Gln | Thr | Leu | Arg |

| 12mer | | Pos 1 | Pos 2 | Pos 3 | Pos 4 | Pos 5 | Pos 6 | Pos 7 | Pos 8 | Pos 9 | Pos 10 | Pos 11 | Pos 12 |
|---|---|---|---|---|---|---|---|---|---|---|---|---|---|
| 1 | W4A-2-12 | Trp | Pro | Ala | Asn | Lys | Leu | Ser | Thr | Lys | Ser | Met | Tyr |
| 2 | W4A-2-28 | Trp | Pro | Ala | Asn | Lys | Leu | Ser | Thr | Lys | Ser | Met | Tyr |
| 3 | W4A-2-31 | Asn | Pro | Tyr | His | Pro | Thr | Ile | Pro | Gln | Ser | Val | His |

Fig. 8

| 7mer constrained | | Pos 1 | Pos 2 | Pos 3 | Pos 4 | Pos 5 | Pos 6 | Pos 7 | | | |
|---|---|---|---|---|---|---|---|---|---|---|---|
| 1 W4a-3-20 | A C | Arg | His | Thr | Leu | Pro | Leu | His | C | | |
| 2 W4a-3-1 | A C | Asn | Pro | Gln | Met | Gln | Arg | Ser | C | | |
| 3 W4a-3-38 | A C | Asn | Tyr | Pro | Thr | Leu | Lys | Ser | C | | |
| 4 W4a-3-40 | A C | Asn | Tyr | Pro | Thr | Leu | Lys | Ser | C | | |
| 5 W4a-3-24 | A C | Asp | Met | Arg | Gln | Gln | Arg | Ser | C | | |
| 6 W4a-3-14 | A C | Gln | Asn | Pro | Arg | Gln | Ile | Tyr | C | | |
| 7 W4a-3-18 | A C | Gln | Asn | Pro | Arg | Gln | Ile | Tyr | C | | |
| 8 W4a-3-21 | A C | Gln | Asn | Pro | Arg | Gln | Ile | Tyr | C | | |
| 9 W4a-3-22 | A C | Gln | Asn | Pro | Arg | Gln | Ile | Tyr | C | | |
| 10 W4a-3-27 | A C | Gln | Asn | Pro | Arg | Gln | Ile | Tyr | C | | |
| 11 W4a-3-31 | A C | Gln | Asn | Pro | Arg | Gln | Ile | Tyr | C | | |
| 12 W4a-3-32 | A C | Gln | Asn | Pro | Arg | Gln | Ile | Tyr | C | | |
| 13 W4a-3-39 | A C | Gln | Asn | Pro | Arg | Gln | Ile | Tyr | C | | |
| 14 W4a-3-4 | A C | Gln | Thr | His | Ser | Ser | Leu | Trp | C | | |
| 15 W4a-3-6 | A C | Gln | Thr | Tyr | Gln | Gln | Pro | Leu | C | | |
| 16 W4a-3-3 | A C | Gln | Thr | Tyr | Ala | Arg | Pro | Leu | C | | |
| 17 W4a-3-30 | A C | Gln | Thr | Ser | Arg | Leu | Phe | Ser | C | | |
| 18 W4a-3-35 | A C | Gly | Thr | Gln | Thr | Leu | Gln | Tyr | C | | |
| 19 W4a-3-34 | A C | Leu | Ala | Phe | Asn | Lys | His | Gly | C | | |
| 20 W4a-3-23 | A C | Lys | Ala | Met | Gln | Phe | Val | His | C | | |
| 21 W4a-3-16 | A C | Lys | Pro | Met | Gln | Phe | Val | His | C | | |
| 22 W4a-3-29 | A C | Lys | Pro | Met | Gln | Phe | Val | His | C | | |
| 23 W4a-3-37 | A C | Lys | Pro | Lys | Gln | Lys | Ala | His | C | | |
| 24 W4a-3-19 | A C | Pro | Ala | Ser | Gly | Thr | Pro | His | C | | |
| 25 W4a-3-33 | A C | Ser | Ala | His | His | His | Arg | His | C | | |
| 26 W4a-3-2 | A C | Ser | Ser | Tyr | Gln | Tyr | His | Ala | C | | |
| 27 W4a-3-28 | A C | Ser | Gly | Pro | Thr | Ser | Leu | Ser | C | | |
| 28 W4a-3-26 | A C | Thr | Gly | Pro | Thr | Ser | Leu | Ser | C | | |

| 12 mer | Pos 1 | Pos 2 | Pos 3 | Pos 4 | Pos 5 | Pos 6 | Pos 7 | Pos 8 | Pos 9 | Pos 10 | Pos 11 | Pos 12 |
|---|---|---|---|---|---|---|---|---|---|---|---|---|
| 1 W4a-3-36 | Leu | Arg | Ala | Phe | Pro | Ser | Leu | Pro | His | Thr | Val | Thr |

| sample | Pos 1 | Pos 2 | Pos 3 | Pos 4 | Pos 5 | Pos 6 | Pos 7 | Pos 8 | Pos 9 | Pos 10 | Pos 11 | Pos 12 |
|---|---|---|---|---|---|---|---|---|---|---|---|---|
| 1 HA410 | A | C | Asn | Gln | Arg | Gln | Met | Gln | Leu | C | | |
| 2 HA411 | A | C | Asn | Lys | Pro | Leu | Ser | Thr | Leu | C | | |
| 3 HA416 | A | C | His | Thr | Leu | Leu | Ser | Thr | Thr | C | | |
| 4 HA45 | A | C | Leu | Lys | Pro | Phe | Ser | Gly | Ala | C | | |
| 5 HA412 | A | C | Leu | Gly | Pro | Gly | Lys | Ala | Phe | C | | |
| 6 HA417 | A | C | Leu | Gly | Pro | Gly | Lys | Ala | Phe | C | | |
| 7 HA46 | A | C | Leu | Gly | Pro | Gly | Lys | Ala | Phe | C | | |
| 8 HA48 | A | C | Leu | Gly | Pro | Gly | Lys | Ala | Phe | C | | |
| 9 HA41 | A | C | Ser | Thr | Ser | Ala | Lys | His | Trp | C | | |
| 1 HA413 | Thr | Met | Gly | Phe | Thr | Ala | Pro | Arg | Phe | Pro | His | Tyr |
| 2 HA414 | Thr | Met | Gly | Phe | Thr | Ala | Pro | Arg | Phe | Pro | His | Trp |
| 3 HA415 | Thr | Met | Gly | Phe | Thr | Ala | Pro | Arg | Phe | Pro | His | Tyr |
| 4 HA42 | Thr | Met | Gly | Phe | Thr | Ala | Pro | Arg | Phe | Pro | His | Tyr |
| 5 HA43 | Thr | Met | Gly | Phe | Thr | Ala | Pro | Arg | Phe | Pro | His | Tyr |
| 6 HA44 | Thr | Met | Gly | Phe | Thr | Ala | Pro | Arg | Phe | Pro | His | Tyr |
| 7 HA47 | Thr | Met | Gly | Phe | Thr | Ala | Pro | Arg | Phe | Pro | His | Tyr |

Fig. 11

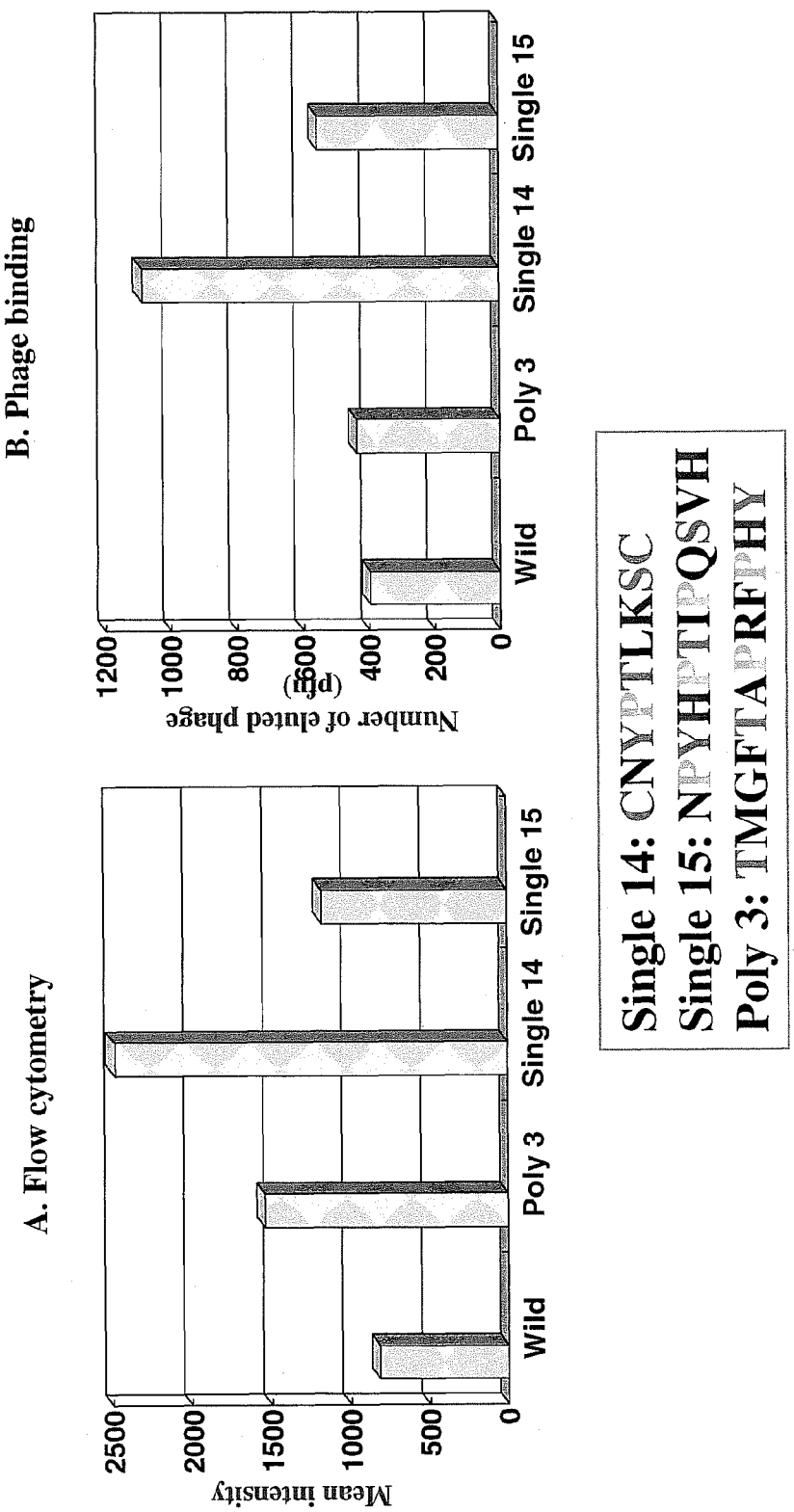
Fig. 12. Flow cytometry vs. phage binding assay
Single 14: CNYPTLKSC
Single 15: NPYHPTPQSVH
Poly 3: TMGFTAPRFPHY Fig. 14. Crystal structure of HA ($Ca_{10}(OH)_2(PO_4)_6$)

viewed down the a (or b) axis. (10.0) face.

Zeta potential of HA: -11.45 ±1.49mV
HA surfaces are negatively charged (h00) surface.

Fig. 15. Zeta potential measurement on single crystal HA surface at pH=7.5

Fig. 16. Computer simulation: N YH T QSVH-GGGK-biotin

Fig. 17. Computer simulation of HA binding peptide: N-DYHPTIPQSVH-GG

Fig. 18. Random coil structure of HA binding peptides

Fig. 19. Peptide templated HA nucleation on TEM grid

Fig. 23
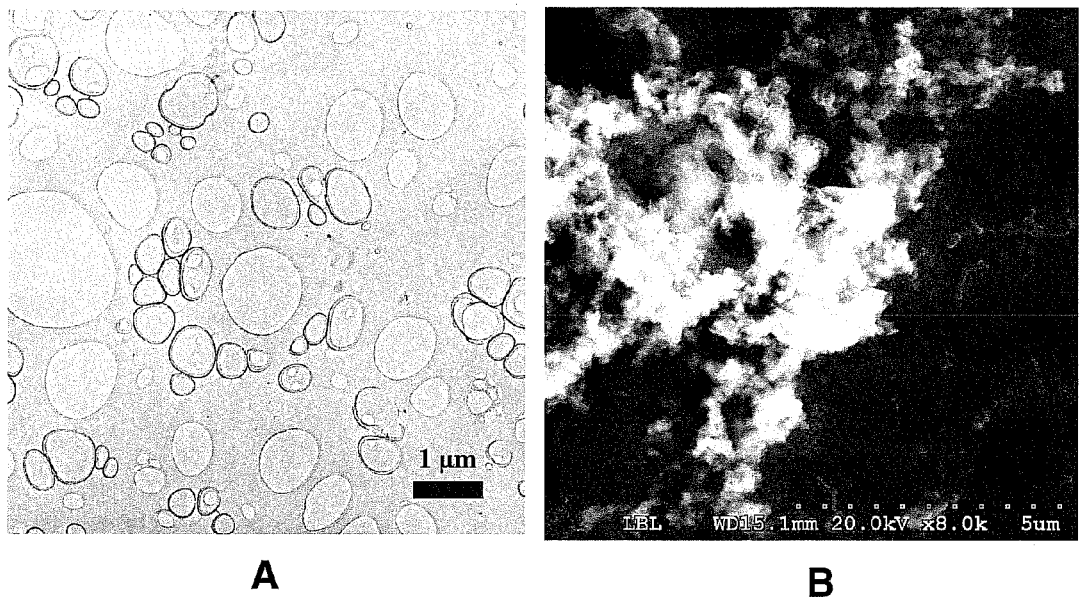
A  B
Fig. 24. Control peptide templated HA nucleation experiment
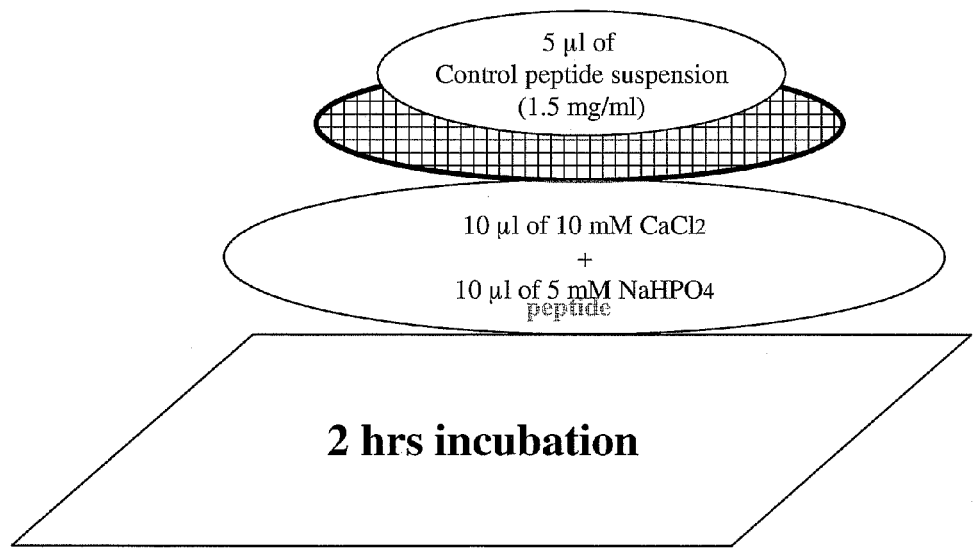

Fig. 25. Control experiment (peptide 1-3)
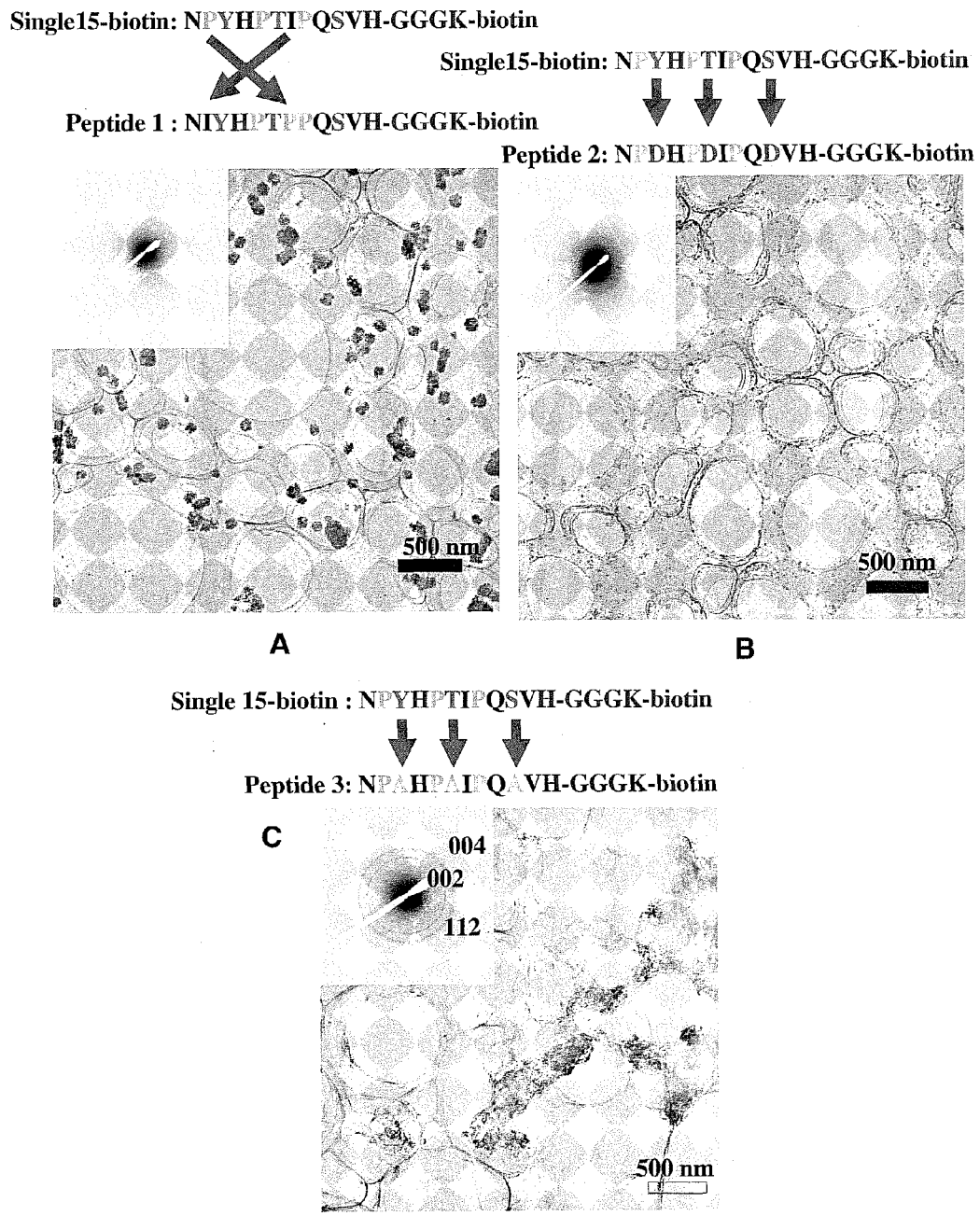

Fig. 26. Control experiment (peptides 4 and 5)
Single 15-biotin : NPYHPTIPQSVH-GGGK-biotin
Peptide 4: NPYAPTIPQSVA-GGGK-biotin
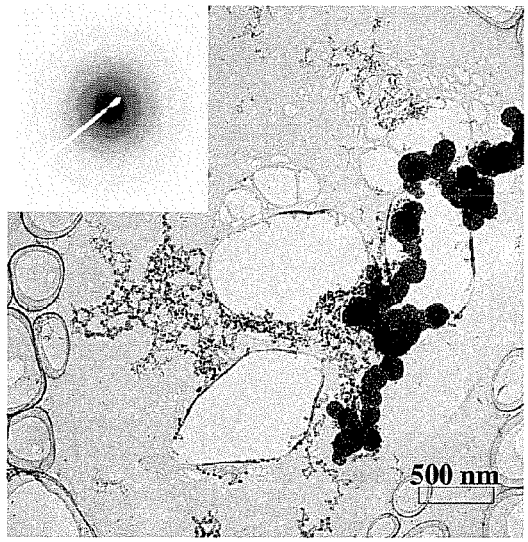
Single 15-biotin : NPYHPTIPQSVH-GGGK-biotin
Peptide 5: APYHPTIPASVH-GGGK-biotin
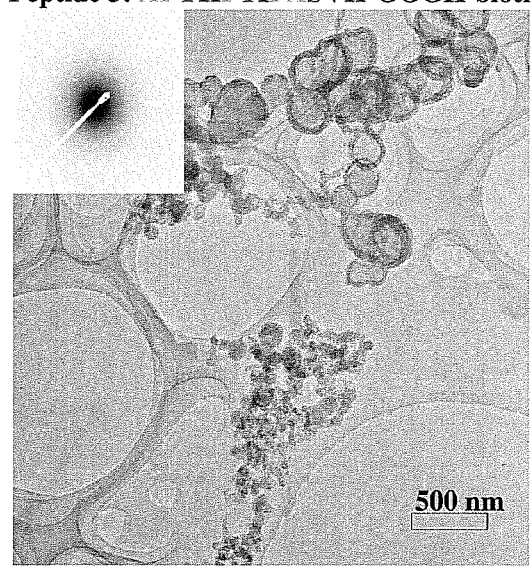

SEQUENCE LISTING

```
<160> NUMBER OF SEQ ID NOS: 273

<210> SEQ ID NO 1
<211> LENGTH: 7
<212> TYPE: PRT
<213> ORGANISM: Artificial
<220> FEATURE:
<223> OTHER INFORMATION: synthetic peptide

<400> SEQUENCE: 1

Arg Pro His Thr Ile Thr Asn
1               5

<210> SEQ ID NO 2
<211> LENGTH: 7
<212> TYPE: PRT
<213> ORGANISM: Artificial
```

```
-continued

<220> FEATURE:
<223> OTHER INFORMATION: synthetic peptide

<400> SEQUENCE: 2

Gln Ser Ser Tyr Asn Pro Ile
1               5

<210> SEQ ID NO 3
<211> LENGTH: 7
<212> TYPE: PRT
<213> ORGANISM: Artificial
<220> FEATURE:
<223> OTHER INFORMATION: synthetic peptide

<400> SEQUENCE: 3

Gln Thr His Ala Arg His Gln
1               5

<210> SEQ ID NO 4
<211> LENGTH: 7
<212> TYPE: PRT
<213> ORGANISM: Artificial
<220> FEATURE:
<223> OTHER INFORMATION: synthetic peptide

<400> SEQUENCE: 4

Glu Thr Arg Thr Gln Leu Leu
1               5

<210> SEQ ID NO 5
<211> LENGTH: 7
<212> TYPE: PRT
<213> ORGANISM: Artificial
<220> FEATURE:
<223> OTHER INFORMATION: Synthetic peptide

<400> SEQUENCE: 5

His His Gln Arg Ser Pro Ala
1               5

<210> SEQ ID NO 6
<211> LENGTH: 7
<212> TYPE: PRT
<213> ORGANISM: Artificial
<220> FEATURE:
<223> OTHER INFORMATION: Synthetic peptide

<400> SEQUENCE: 6

Leu Gln Lys Ser Pro Ser Leu
1               5

<210> SEQ ID NO 7
<211> LENGTH: 7
<212> TYPE: PRT
<213> ORGANISM: Artificial
<220> FEATURE:
<223> OTHER INFORMATION: Synthetic peptide

<400> SEQUENCE: 7

Pro Pro Lys Asp Ser Arg Gly
1               5

<210> SEQ ID NO 8
<211> LENGTH: 7
<212> TYPE: PRT
<213> ORGANISM: Artificial
<220> FEATURE:
<223> OTHER INFORMATION: Synthetic peptide
```

```
<400> SEQUENCE: 8

Ser Ala Lys Lys Val Phe Ser
1               5

<210> SEQ ID NO 9
<211> LENGTH: 7
<212> TYPE: PRT
<213> ORGANISM: Artificial
<220> FEATURE:
<223> OTHER INFORMATION: Synthetic peptide

<400> SEQUENCE: 9

Ser Gln His Ser Thr Gln Asp
1               5

<210> SEQ ID NO 10
<211> LENGTH: 7
<212> TYPE: PRT
<213> ORGANISM: Artificial
<220> FEATURE:
<223> OTHER INFORMATION: Synthetic peptide

<400> SEQUENCE: 10

Thr Ile His Ser Lys Pro Ala
1               5

<210> SEQ ID NO 11
<211> LENGTH: 7
<212> TYPE: PRT
<213> ORGANISM: Artificial
<220> FEATURE:
<223> OTHER INFORMATION: Synthetic peptide

<400> SEQUENCE: 11

Thr Lys Asp Trp Leu Pro Ser
1               5

<210> SEQ ID NO 12
<211> LENGTH: 7
<212> TYPE: PRT
<213> ORGANISM: Artificial
<220> FEATURE:
<223> OTHER INFORMATION: Synthetic peptide

<400> SEQUENCE: 12

Ala Asn Pro Pro Leu Ser Leu
1               5

<210> SEQ ID NO 13
<211> LENGTH: 7
<212> TYPE: PRT
<213> ORGANISM: Artificial
<220> FEATURE:
<223> OTHER INFORMATION: Synthetic peptide

<400> SEQUENCE: 13

Ala Lys Gln Thr Val Pro Val
1               5

<210> SEQ ID NO 14
<211> LENGTH: 7
<212> TYPE: PRT
<213> ORGANISM: Artificial
<220> FEATURE:
<223> OTHER INFORMATION: Synthetic peptide

<400> SEQUENCE: 14
```

```
Ala Thr Phe Ser Pro Pro Leu
1               5

<210> SEQ ID NO 15
<211> LENGTH: 7
<212> TYPE: PRT
<213> ORGANISM: Artificial
<220> FEATURE:
<223> OTHER INFORMATION: Synthetic peptide

<400> SEQUENCE: 15

Asp Gln Tyr Trp Gly Leu Arg
1               5

<210> SEQ ID NO 16
<211> LENGTH: 7
<212> TYPE: PRT
<213> ORGANISM: Artificial
<220> FEATURE:
<223> OTHER INFORMATION: Synthetic peptide

<400> SEQUENCE: 16

Glu Pro Asn His Thr Arg Phe
1               5

<210> SEQ ID NO 17
<211> LENGTH: 7
<212> TYPE: PRT
<213> ORGANISM: Artificial
<220> FEATURE:
<223> OTHER INFORMATION: Synthetic peptide

<400> SEQUENCE: 17

His Met Leu Ala Gln Thr Phe
1               5

<210> SEQ ID NO 18
<211> LENGTH: 7
<212> TYPE: PRT
<213> ORGANISM: Artificial
<220> FEATURE:
<223> OTHER INFORMATION: Synthetic peptide

<400> SEQUENCE: 18

Ile Gly Tyr Pro Val Leu Pro
1               5

<210> SEQ ID NO 19
<211> LENGTH: 7
<212> TYPE: PRT
<213> ORGANISM: Artificial
<220> FEATURE:
<223> OTHER INFORMATION: Synthetic peptide

<400> SEQUENCE: 19

Lys Leu Ser Ala Trp Ser Phe
1               5

<210> SEQ ID NO 20
<211> LENGTH: 7
<212> TYPE: PRT
<213> ORGANISM: Artificial
<220> FEATURE:
<223> OTHER INFORMATION: Synthetic peptide

<400> SEQUENCE: 20

Met Tyr Pro Leu Pro Ala Pro
```

```
1               5

<210> SEQ ID NO 21
<211> LENGTH: 7
<212> TYPE: PRT
<213> ORGANISM: Artificial
<220> FEATURE:
<223> OTHER INFORMATION: Synthetic peptide

<400> SEQUENCE: 21

Phe Thr Leu Pro Thr Ile Arg
1               5

<210> SEQ ID NO 22
<211> LENGTH: 7
<212> TYPE: PRT
<213> ORGANISM: Artificial
<220> FEATURE:
<223> OTHER INFORMATION: Synthetic peptide

<400> SEQUENCE: 22

Ser Met Ala Ala Lys Ser Ser
1               5

<210> SEQ ID NO 23
<211> LENGTH: 7
<212> TYPE: PRT
<213> ORGANISM: Artificial
<220> FEATURE:
<223> OTHER INFORMATION: Synthetic peptide

<400> SEQUENCE: 23

Ser Met Tyr Asp Thr His Ser
1               5

<210> SEQ ID NO 24
<211> LENGTH: 7
<212> TYPE: PRT
<213> ORGANISM: Artificial
<220> FEATURE:
<223> OTHER INFORMATION: Synthetic peptide

<400> SEQUENCE: 24

Ser Thr Leu Ala Ser Met Arg
1               5

<210> SEQ ID NO 25
<211> LENGTH: 7
<212> TYPE: PRT
<213> ORGANISM: Artificial
<220> FEATURE:
<223> OTHER INFORMATION: Synthetic peptide

<400> SEQUENCE: 25

Thr Leu Met Thr Thr Pro Pro
1               5

<210> SEQ ID NO 26
<211> LENGTH: 7
<212> TYPE: PRT
<213> ORGANISM: Artificial
<220> FEATURE:
<223> OTHER INFORMATION: Synthetic peptide

<400> SEQUENCE: 26

Trp Leu Pro Pro Arg Thr Gln
1               5
```

<210> SEQ ID NO 27
<211> LENGTH: 12
<212> TYPE: PRT
<213> ORGANISM: Artificial
<220> FEATURE:
<223> OTHER INFORMATION: synthetic peptide

<400> SEQUENCE: 27

Arg Thr Pro Leu Gln Pro Leu Glu Asp Phe Arg Pro
1               5                   10

<210> SEQ ID NO 28
<211> LENGTH: 12
<212> TYPE: PRT
<213> ORGANISM: Artificial
<220> FEATURE:
<223> OTHER INFORMATION: synthetic peptide

<400> SEQUENCE: 28

Asn Thr Thr Thr Asp Ile Pro Ser Pro Ser Gln Phe
1               5                   10

<210> SEQ ID NO 29
<211> LENGTH: 12
<212> TYPE: PRT
<213> ORGANISM: Artificial
<220> FEATURE:
<223> OTHER INFORMATION: synthetic peptide

<400> SEQUENCE: 29

Thr Leu Asp Lys Tyr Thr Arg Leu Leu Ser Arg Tyr
1               5                   10

<210> SEQ ID NO 30
<211> LENGTH: 12
<212> TYPE: PRT
<213> ORGANISM: Artificial
<220> FEATURE:
<223> OTHER INFORMATION: synthetic peptide

<400> SEQUENCE: 30

Tyr Pro Ile Met Ser His Thr Cys Cys His Gly Val
1               5                   10

<210> SEQ ID NO 31
<211> LENGTH: 7
<212> TYPE: PRT
<213> ORGANISM: Artificial
<220> FEATURE:
<223> OTHER INFORMATION: synthetic peptide

<400> SEQUENCE: 31

Tyr Glu Pro Ala Ala Ala Glu
1               5

<210> SEQ ID NO 32
<211> LENGTH: 7
<212> TYPE: PRT
<213> ORGANISM: Artificial
<220> FEATURE:
<223> OTHER INFORMATION: synthetic peptide

<400> SEQUENCE: 32

Ala Asn Pro Tyr His Arg His
1               5

<210> SEQ ID NO 33

```
<211> LENGTH: 7
<212> TYPE: PRT
<213> ORGANISM: Artificial
<220> FEATURE:
<223> OTHER INFORMATION: synthetic peptide

<400> SEQUENCE: 33

Ala Ser Gly Pro Thr Asn Val
1               5

<210> SEQ ID NO 34
<211> LENGTH: 7
<212> TYPE: PRT
<213> ORGANISM: Artificial
<220> FEATURE:
<223> OTHER INFORMATION: synthetic peptide

<400> SEQUENCE: 34

Gln Asn Tyr Leu Leu Pro Lys
1               5

<210> SEQ ID NO 35
<211> LENGTH: 7
<212> TYPE: PRT
<213> ORGANISM: Artificial
<220> FEATURE:
<223> OTHER INFORMATION: synthetic peptide

<400> SEQUENCE: 35

Gly Thr Gln Thr Pro Gln Pro
1               5

<210> SEQ ID NO 36
<211> LENGTH: 7
<212> TYPE: PRT
<213> ORGANISM: Artificial
<220> FEATURE:
<223> OTHER INFORMATION: synthetic peptide

<400> SEQUENCE: 36

His Ser Thr Gly Pro Thr Arg
1               5

<210> SEQ ID NO 37
<211> LENGTH: 7
<212> TYPE: PRT
<213> ORGANISM: Artificial
<220> FEATURE:
<223> OTHER INFORMATION: synthetic peptide

<400> SEQUENCE: 37

Leu Ser Lys Asn Pro Leu Leu
1               5

<210> SEQ ID NO 38
<211> LENGTH: 7
<212> TYPE: PRT
<213> ORGANISM: Artificial
<220> FEATURE:
<223> OTHER INFORMATION: synthetic peptide

<400> SEQUENCE: 38

Leu Ser Lys Asn Pro Leu Leu
1               5

<210> SEQ ID NO 39
<211> LENGTH: 7
<212> TYPE: PRT
```

```
<213> ORGANISM: Artificial
<220> FEATURE:
<223> OTHER INFORMATION: synthetic peptide

<400> SEQUENCE: 39

Lys Leu His Ala Ser Leu Ala
1               5

<210> SEQ ID NO 40
<211> LENGTH: 7
<212> TYPE: PRT
<213> ORGANISM: Artificial
<220> FEATURE:
<223> OTHER INFORMATION: synthetic peptide

<400> SEQUENCE: 40

Pro Leu Thr Gln Pro Ser His
1               5

<210> SEQ ID NO 41
<211> LENGTH: 7
<212> TYPE: PRT
<213> ORGANISM: Artificial
<220> FEATURE:
<223> OTHER INFORMATION: synthetic peptide

<400> SEQUENCE: 41

Pro His Asn Pro Gly Lys Leu
1               5

<210> SEQ ID NO 42
<211> LENGTH: 7
<212> TYPE: PRT
<213> ORGANISM: Artificial
<220> FEATURE:
<223> OTHER INFORMATION: synthetic peptide

<400> SEQUENCE: 42

Pro Thr Thr Met Thr Arg Trp
1               5

<210> SEQ ID NO 43
<211> LENGTH: 7
<212> TYPE: PRT
<213> ORGANISM: Artificial
<220> FEATURE:
<223> OTHER INFORMATION: synthetic peptide

<400> SEQUENCE: 43

Val His Leu Thr His Gly Gln
1               5

<210> SEQ ID NO 44
<211> LENGTH: 7
<212> TYPE: PRT
<213> ORGANISM: Artificial
<220> FEATURE:
<223> OTHER INFORMATION: synthetic peptide

<400> SEQUENCE: 44

Thr Leu Ala Pro Thr Phe Arg
1               5

<210> SEQ ID NO 45
<211> LENGTH: 7
<212> TYPE: PRT
<213> ORGANISM: Artificial
<220> FEATURE:
```

```
<223> OTHER INFORMATION: synthetic peptide

<400> SEQUENCE: 45

Val His Pro Arg Pro Ser Leu
1               5

<210> SEQ ID NO 46
<211> LENGTH: 7
<212> TYPE: PRT
<213> ORGANISM: Artificial
<220> FEATURE:
<223> OTHER INFORMATION: synthetic peptide

<400> SEQUENCE: 46

Thr Leu Leu Arg Thr Gln Val
1               5

<210> SEQ ID NO 47
<211> LENGTH: 7
<212> TYPE: PRT
<213> ORGANISM: Artificial
<220> FEATURE:
<223> OTHER INFORMATION: synthetic peptide

<400> SEQUENCE: 47

Ser Ser Pro Pro Arg Val Tyr
1               5

<210> SEQ ID NO 48
<211> LENGTH: 7
<212> TYPE: PRT
<213> ORGANISM: Artificial
<220> FEATURE:
<223> OTHER INFORMATION: synthetic peptide

<400> SEQUENCE: 48

Ser Ser Val Pro Gly Arg Pro
1               5

<210> SEQ ID NO 49
<211> LENGTH: 7
<212> TYPE: PRT
<213> ORGANISM: Artificial
<220> FEATURE:
<223> OTHER INFORMATION: synthetic peptide

<400> SEQUENCE: 49

Leu Pro Phe Gln Pro Pro Ile
1               5

<210> SEQ ID NO 50
<211> LENGTH: 7
<212> TYPE: PRT
<213> ORGANISM: Artificial
<220> FEATURE:
<223> OTHER INFORMATION: synthetic peptide

<400> SEQUENCE: 50

Ile Gln His Gln Ala Lys Thr
1               5

<210> SEQ ID NO 51
<211> LENGTH: 12
<212> TYPE: PRT
<213> ORGANISM: Artificial
<220> FEATURE:
<223> OTHER INFORMATION: synthetic peptide
```

```
<400> SEQUENCE: 51

Leu Pro Arg Asp Leu His Ala Thr Pro Gln Gln Ile
1               5                   10

<210> SEQ ID NO 52
<211> LENGTH: 12
<212> TYPE: PRT
<213> ORGANISM: Artificial
<220> FEATURE:
<223> OTHER INFORMATION: synthetic peptide

<400> SEQUENCE: 52

Leu Thr Pro Thr Met Phe Asn Met His Gly Val Leu
1               5                   10

<210> SEQ ID NO 53
<211> LENGTH: 12
<212> TYPE: PRT
<213> ORGANISM: Artificial
<220> FEATURE:
<223> OTHER INFORMATION: synthetic peptide

<400> SEQUENCE: 53

Ser Ile Pro Lys Met Ile Pro Thr Glu Ser Leu Leu
1               5                   10

<210> SEQ ID NO 54
<211> LENGTH: 12
<212> TYPE: PRT
<213> ORGANISM: Artificial
<220> FEATURE:
<223> OTHER INFORMATION: synthetic peptide

<400> SEQUENCE: 54

Ser Phe Gln Ser Met Ser Leu Met Thr Leu Val Val
1               5                   10

<210> SEQ ID NO 55
<211> LENGTH: 12
<212> TYPE: PRT
<213> ORGANISM: Artificial
<220> FEATURE:
<223> OTHER INFORMATION: synthetic peptide

<400> SEQUENCE: 55

Thr Gln Thr Trp Pro Gln Ser Ser His Gly Leu
1               5                   10

<210> SEQ ID NO 56
<211> LENGTH: 12
<212> TYPE: PRT
<213> ORGANISM: Artificial
<220> FEATURE:
<223> OTHER INFORMATION: synthetic peptide

<400> SEQUENCE: 56

Tyr Glu Leu Gln Met Pro Leu Thr Leu Pro Leu Asn
1               5                   10

<210> SEQ ID NO 57
<211> LENGTH: 12
<212> TYPE: PRT
<213> ORGANISM: Artificial
<220> FEATURE:
<223> OTHER INFORMATION: synthetic peptide

<400> SEQUENCE: 57
```

```
Ala Met Ser Gln Thr Met Thr Ala Ala Ile Glu Lys
1               5                   10

<210> SEQ ID NO 58
<211> LENGTH: 12
<212> TYPE: PRT
<213> ORGANISM: Artificial
<220> FEATURE:
<223> OTHER INFORMATION: synthetic peptide

<400> SEQUENCE: 58

Gly Ser Ala Gly Leu Lys Tyr Pro Leu Tyr Lys Ser
1               5                   10

<210> SEQ ID NO 59
<211> LENGTH: 12
<212> TYPE: PRT
<213> ORGANISM: Artificial
<220> FEATURE:
<223> OTHER INFORMATION: synthetic peptide

<400> SEQUENCE: 59

Ile Asn Phe Gln Phe Leu Lys Pro Ser Thr Thr Arg
1               5                   10

<210> SEQ ID NO 60
<211> LENGTH: 7
<212> TYPE: PRT
<213> ORGANISM: Artificial
<220> FEATURE:
<223> OTHER INFORMATION: synthetic peptide

<400> SEQUENCE: 60

Arg His Thr Leu Pro Leu His
1               5

<210> SEQ ID NO 61
<211> LENGTH: 7
<212> TYPE: PRT
<213> ORGANISM: Artificial
<220> FEATURE:
<223> OTHER INFORMATION: synthetic peptide

<400> SEQUENCE: 61

Asn Phe Ala Met Asn Leu Arg
1               5

<210> SEQ ID NO 62
<211> LENGTH: 7
<212> TYPE: PRT
<213> ORGANISM: Artificial
<220> FEATURE:
<223> OTHER INFORMATION: synthetic peptide

<400> SEQUENCE: 62

Asn Phe Ala Met Asn Leu Arg
1               5

<210> SEQ ID NO 63
<211> LENGTH: 7
<212> TYPE: PRT
<213> ORGANISM: Artificial
<220> FEATURE:
<223> OTHER INFORMATION: synthetic peptide

<400> SEQUENCE: 63

Asn Pro Gln Met Gln Arg Ser
1               5
```

<210> SEQ ID NO 64
<211> LENGTH: 7
<212> TYPE: PRT
<213> ORGANISM: Artificial
<220> FEATURE:
<223> OTHER INFORMATION: synthetic peptide

<400> SEQUENCE: 64

Asn Pro Gln Met Gln Arg Ser
1               5

<210> SEQ ID NO 65
<211> LENGTH: 7
<212> TYPE: PRT
<213> ORGANISM: Artificial
<220> FEATURE:
<223> OTHER INFORMATION: synthetic peptide

<400> SEQUENCE: 65

Asn Pro Gln Met Gln Arg Ser
1               5

<210> SEQ ID NO 66
<211> LENGTH: 7
<212> TYPE: PRT
<213> ORGANISM: Artificial
<220> FEATURE:
<223> OTHER INFORMATION: synthetic peptide

<400> SEQUENCE: 66

Asn Tyr Pro Thr Leu Lys Ser
1               5

<210> SEQ ID NO 67
<211> LENGTH: 7
<212> TYPE: PRT
<213> ORGANISM: Artificial
<220> FEATURE:
<223> OTHER INFORMATION: synthetic peptide

<400> SEQUENCE: 67

Asn Tyr Pro Thr Leu Lys Ser
1               5

<210> SEQ ID NO 68
<211> LENGTH: 7
<212> TYPE: PRT
<213> ORGANISM: Artificial
<220> FEATURE:
<223> OTHER INFORMATION: synthetic peptide

<400> SEQUENCE: 68

Gln Asn Pro Arg Gln Ile Tyr
1               5

<210> SEQ ID NO 69
<211> LENGTH: 7
<212> TYPE: PRT
<213> ORGANISM: Artificial
<220> FEATURE:
<223> OTHER INFORMATION: synthetic peptide

<400> SEQUENCE: 69

Gln Asn Pro Arg Gln Ile Tyr
1               5

```
<210> SEQ ID NO 70
<211> LENGTH: 7
<212> TYPE: PRT
<213> ORGANISM: Artificial
<220> FEATURE:
<223> OTHER INFORMATION: synthetic peptide

<400> SEQUENCE: 70

Gln Asn Pro Arg Gln Ile Tyr
1               5

<210> SEQ ID NO 71
<211> LENGTH: 7
<212> TYPE: PRT
<213> ORGANISM: Artificial
<220> FEATURE:
<223> OTHER INFORMATION: synthetic peptide

<400> SEQUENCE: 71

Gln Asn Pro Arg Gln Ile Tyr
1               5

<210> SEQ ID NO 72
<211> LENGTH: 7
<212> TYPE: PRT
<213> ORGANISM: Artificial
<220> FEATURE:
<223> OTHER INFORMATION: synthetic peptide

<400> SEQUENCE: 72

Glu Thr Tyr Ala Arg Pro Leu
1               5

<210> SEQ ID NO 73
<211> LENGTH: 7
<212> TYPE: PRT
<213> ORGANISM: Artificial
<220> FEATURE:
<223> OTHER INFORMATION: synthetic peptide

<400> SEQUENCE: 73

Glu Thr Val Cys Ala Ser Ser
1               5

<210> SEQ ID NO 74
<211> LENGTH: 7
<212> TYPE: PRT
<213> ORGANISM: Artificial
<220> FEATURE:
<223> OTHER INFORMATION: synthetic peptide

<400> SEQUENCE: 74

Lys Pro Met Gln Phe Val His
1               5

<210> SEQ ID NO 75
<211> LENGTH: 7
<212> TYPE: PRT
<213> ORGANISM: Artificial
<220> FEATURE:
<223> OTHER INFORMATION: synthetic peptide

<400> SEQUENCE: 75

Lys Pro Met Gln Phe Val His
1               5

<210> SEQ ID NO 76
<211> LENGTH: 7
```

```
<212> TYPE: PRT
<213> ORGANISM: Artificial
<220> FEATURE:
<223> OTHER INFORMATION: synthetic peptide

<400> SEQUENCE: 76

Pro Ala Lys Gln Lys Ala His
1               5

<210> SEQ ID NO 77
<211> LENGTH: 7
<212> TYPE: PRT
<213> ORGANISM: Artificial
<220> FEATURE:
<223> OTHER INFORMATION: synthetic peptide

<400> SEQUENCE: 77

Pro Thr Thr Trp Gly His Leu
1               5

<210> SEQ ID NO 78
<211> LENGTH: 7
<212> TYPE: PRT
<213> ORGANISM: Artificial
<220> FEATURE:
<223> OTHER INFORMATION: synthetic peptide

<400> SEQUENCE: 78

Pro Thr Thr Trp Gly His Leu
1               5

<210> SEQ ID NO 79
<211> LENGTH: 7
<212> TYPE: PRT
<213> ORGANISM: Artificial
<220> FEATURE:
<223> OTHER INFORMATION: synthetic peptide

<400> SEQUENCE: 79

Ser Ala Ser Gly Thr Pro Ser
1               5

<210> SEQ ID NO 80
<211> LENGTH: 7
<212> TYPE: PRT
<213> ORGANISM: Artificial
<220> FEATURE:
<223> OTHER INFORMATION: synthetic peptide

<400> SEQUENCE: 80

Ser Ser Tyr Glu Tyr His Ala
1               5

<210> SEQ ID NO 81
<211> LENGTH: 7
<212> TYPE: PRT
<213> ORGANISM: Artificial
<220> FEATURE:
<223> OTHER INFORMATION: synthetic peptide

<400> SEQUENCE: 81

Ser Ser Tyr Glu Tyr His Ala
1               5

<210> SEQ ID NO 82
<211> LENGTH: 7
<212> TYPE: PRT
<213> ORGANISM: Artificial
```

```
<220> FEATURE:
<223> OTHER INFORMATION: synthetic peptide

<400> SEQUENCE: 82

Ser Thr Gln Ala His Pro Trp
1               5

<210> SEQ ID NO 83
<211> LENGTH: 7
<212> TYPE: PRT
<213> ORGANISM: Artificial
<220> FEATURE:
<223> OTHER INFORMATION: synthetic peptide

<400> SEQUENCE: 83

Thr Val Leu Gly Thr Phe Pro
1               5

<210> SEQ ID NO 84
<211> LENGTH: 7
<212> TYPE: PRT
<213> ORGANISM: Artificial
<220> FEATURE:
<223> OTHER INFORMATION: synthetic peptide

<400> SEQUENCE: 84

Trp Tyr Pro Asn His Leu Ala
1               5

<210> SEQ ID NO 85
<211> LENGTH: 7
<212> TYPE: PRT
<213> ORGANISM: Artificial
<220> FEATURE:
<223> OTHER INFORMATION: synthetic peptide

<400> SEQUENCE: 85

Thr Thr Tyr Asn Ser Pro Pro
1               5

<210> SEQ ID NO 86
<211> LENGTH: 7
<212> TYPE: PRT
<213> ORGANISM: Artificial
<220> FEATURE:
<223> OTHER INFORMATION: synthetic peptide

<400> SEQUENCE: 86

Met Thr Ser Gln Thr Leu Arg
1               5

<210> SEQ ID NO 87
<211> LENGTH: 12
<212> TYPE: PRT
<213> ORGANISM: Artificial
<220> FEATURE:
<223> OTHER INFORMATION: synthetic peptide

<400> SEQUENCE: 87

Trp Pro Ala Asn Lys Leu Ser Thr Lys Ser Met Tyr
1               5                   10

<210> SEQ ID NO 88
<211> LENGTH: 12
<212> TYPE: PRT
<213> ORGANISM: Artificial
<220> FEATURE:
<223> OTHER INFORMATION: synthetic peptide
```

<400> SEQUENCE: 88

Trp Pro Ala Asn Lys Leu Ser Thr Lys Ser Met Tyr
1               5                   10

<210> SEQ ID NO 89
<211> LENGTH: 12
<212> TYPE: PRT
<213> ORGANISM: Artificial
<220> FEATURE:
<223> OTHER INFORMATION: synthetic peptide

<400> SEQUENCE: 89

Asn Pro Tyr His Pro Thr Ile Pro Gln Ser Val His
1               5                   10

<210> SEQ ID NO 90
<211> LENGTH: 7
<212> TYPE: PRT
<213> ORGANISM: Artificial
<220> FEATURE:
<223> OTHER INFORMATION: synthetic peptide

<400> SEQUENCE: 90

Asp Lys Leu His Arg Leu Ala
1               5

<210> SEQ ID NO 91
<211> LENGTH: 7
<212> TYPE: PRT
<213> ORGANISM: Artificial
<220> FEATURE:
<223> OTHER INFORMATION: synthetic peptide

<400> SEQUENCE: 91

Gln Pro Gly Leu Trp Pro Ser
1               5

<210> SEQ ID NO 92
<211> LENGTH: 7
<212> TYPE: PRT
<213> ORGANISM: Artificial
<220> FEATURE:
<223> OTHER INFORMATION: synthetic peptide

<400> SEQUENCE: 92

Glu Ser Leu Lys Ser Ile Ser
1               5

<210> SEQ ID NO 93
<211> LENGTH: 7
<212> TYPE: PRT
<213> ORGANISM: Artificial
<220> FEATURE:
<223> OTHER INFORMATION: synthetic peptide

<400> SEQUENCE: 93

Gly Ser Cys Pro Pro Lys Lys
1               5

<210> SEQ ID NO 94
<211> LENGTH: 7
<212> TYPE: PRT
<213> ORGANISM: Artificial
<220> FEATURE:
<223> OTHER INFORMATION: synthetic peptide

<400> SEQUENCE: 94

```
Gly Ser Leu Phe Lys Ala Leu
1               5

<210> SEQ ID NO 95
<211> LENGTH: 7
<212> TYPE: PRT
<213> ORGANISM: Artificial
<220> FEATURE:
<223> OTHER INFORMATION: synthetic peptide

<400> SEQUENCE: 95

His Gln Trp Asp His Lys Tyr
1               5

<210> SEQ ID NO 96
<211> LENGTH: 7
<212> TYPE: PRT
<213> ORGANISM: Artificial
<220> FEATURE:
<223> OTHER INFORMATION: synthetic peptide

<400> SEQUENCE: 96

Leu Ser Ala Pro Met Glu Tyr
1               5

<210> SEQ ID NO 97
<211> LENGTH: 7
<212> TYPE: PRT
<213> ORGANISM: Artificial
<220> FEATURE:
<223> OTHER INFORMATION: synthetic peptide

<400> SEQUENCE: 97

Met Lys Val His Glu Arg Ser
1               5

<210> SEQ ID NO 98
<211> LENGTH: 7
<212> TYPE: PRT
<213> ORGANISM: Artificial
<220> FEATURE:
<223> OTHER INFORMATION: synthetic peptide

<400> SEQUENCE: 98

Phe Val Asn Leu Leu Gly Gln
1               5

<210> SEQ ID NO 99
<211> LENGTH: 7
<212> TYPE: PRT
<213> ORGANISM: Artificial
<220> FEATURE:
<223> OTHER INFORMATION: synthetic peptide

<400> SEQUENCE: 99

Pro Ile Asp Ala Phe Phe Asp
1               5

<210> SEQ ID NO 100
<211> LENGTH: 7
<212> TYPE: PRT
<213> ORGANISM: Artificial
<220> FEATURE:
<223> OTHER INFORMATION: synthetic peptide

<400> SEQUENCE: 100

Pro Pro Asn Met Ala Arg Ala
```

<210> SEQ ID NO 101
<211> LENGTH: 7
<212> TYPE: PRT
<213> ORGANISM: Artificial
<220> FEATURE:
<223> OTHER INFORMATION: synthetic peptide

<400> SEQUENCE: 101

Pro Thr Asn Lys Pro His Thr
1               5

<210> SEQ ID NO 102
<211> LENGTH: 7
<212> TYPE: PRT
<213> ORGANISM: Artificial
<220> FEATURE:
<223> OTHER INFORMATION: synthetic peptide

<400> SEQUENCE: 102

Ser Pro Asn Asn Thr Arg Glu
1               5

<210> SEQ ID NO 103
<211> LENGTH: 7
<212> TYPE: PRT
<213> ORGANISM: Artificial
<220> FEATURE:
<223> OTHER INFORMATION: synthetic peptide

<400> SEQUENCE: 103

Ser Pro Glu Met Lys Pro Arg
1               5

<210> SEQ ID NO 104
<211> LENGTH: 7
<212> TYPE: PRT
<213> ORGANISM: Artificial
<220> FEATURE:
<223> OTHER INFORMATION: synthetic peptide

<400> SEQUENCE: 104

Ser Ser Ser Met Ala Lys Met
1               5

<210> SEQ ID NO 105
<211> LENGTH: 7
<212> TYPE: PRT
<213> ORGANISM: Artificial
<220> FEATURE:
<223> OTHER INFORMATION: synthetic peptide

<400> SEQUENCE: 105

Thr Asp His Pro Pro Lys Ala
1               5

<210> SEQ ID NO 106
<211> LENGTH: 7
<212> TYPE: PRT
<213> ORGANISM: Artificial
<220> FEATURE:
<223> OTHER INFORMATION: synthetic peptide

<400> SEQUENCE: 106

Thr Leu Ala Phe Gln Thr Ala
1               5

<210> SEQ ID NO 107
<211> LENGTH: 7
<212> TYPE: PRT
<213> ORGANISM: Artificial
<220> FEATURE:
<223> OTHER INFORMATION: synthetic peptide

<400> SEQUENCE: 107

Ala Pro Leu Ser Leu Ser Leu
1               5

<210> SEQ ID NO 108
<211> LENGTH: 7
<212> TYPE: PRT
<213> ORGANISM: Artificial
<220> FEATURE:
<223> OTHER INFORMATION: synthetic peptide

<400> SEQUENCE: 108

His Tyr Pro Thr Val Asn Phe
1               5

<210> SEQ ID NO 109
<211> LENGTH: 12
<212> TYPE: PRT
<213> ORGANISM: Artificial
<220> FEATURE:
<223> OTHER INFORMATION: synthetic peptide

<400> SEQUENCE: 109

Gln His Asn Phe Arg Gly Ala Ser Ser Ser Ala Pro
1               5                   10

<210> SEQ ID NO 110
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: VARIANT
<222> LOCATION: (5)..(5)
<223> OTHER INFORMATION: X is Arg or Pro

<400> SEQUENCE: 110

His Gln Phe Pro Xaa Ser Asn Leu Val Trp Lys Pro
1               5                   10

<210> SEQ ID NO 111
<211> LENGTH: 12
<212> TYPE: PRT
<213> ORGANISM: Artificial
<220> FEATURE:
<223> OTHER INFORMATION: synthetic peptide

<400> SEQUENCE: 111

Leu Ser Leu Arg Ala Ser Ala Ala Thr Asp Phe Gln
1               5                   10

<210> SEQ ID NO 112
<211> LENGTH: 12
<212> TYPE: PRT
<213> ORGANISM: Artificial
<220> FEATURE:
<223> OTHER INFORMATION: synthetic peptide

<400> SEQUENCE: 112

Met Gln Phe Thr Pro Ala Pro Ser Pro Ser Asp His

<210> SEQ ID NO 113
<211> LENGTH: 12
<212> TYPE: PRT
<213> ORGANISM: Artificial
<220> FEATURE:
<223> OTHER INFORMATION: synthetic peptide

<400> SEQUENCE: 113

Ser Val Phe Leu Pro Thr Arg His Ser Pro Asp Leu
1               5                   10

<210> SEQ ID NO 114
<211> LENGTH: 12
<212> TYPE: PRT
<213> ORGANISM: Artificial
<220> FEATURE:
<223> OTHER INFORMATION: synthetic peptide

<400> SEQUENCE: 114

Ser Val Ser Val Gly Met Lys Pro Ser Pro Arg Pro
1               5                   10

<210> SEQ ID NO 115
<211> LENGTH: 12
<212> TYPE: PRT
<213> ORGANISM: Artificial
<220> FEATURE:
<223> OTHER INFORMATION: synthetic peptide

<400> SEQUENCE: 115

Ser Val Ser Val Gly Met Lys Pro Ser Pro Arg Pro
1               5                   10

<210> SEQ ID NO 116
<211> LENGTH: 12
<212> TYPE: PRT
<213> ORGANISM: Artificial
<220> FEATURE:
<223> OTHER INFORMATION: synthetic peptide

<400> SEQUENCE: 116

Ser Val Ser Val Gly Met Lys Pro Ser Pro Arg Pro
1               5                   10

<210> SEQ ID NO 117
<211> LENGTH: 12
<212> TYPE: PRT
<213> ORGANISM: Artificial
<220> FEATURE:
<223> OTHER INFORMATION: synthetic peptide

<400> SEQUENCE: 117

Ser Val Ser Val Gly Met Lys Pro Ser Pro Arg Pro
1               5                   10

<210> SEQ ID NO 118
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: VARIANT
<222> LOCATION: (11)..(11)
<223> OTHER INFORMATION: Xaa can be any amino acid residue

<400> SEQUENCE: 118

```
Ser Val Ser Val Gly Met Asn Ala Glu Ser Xaa Ala
1               5                  10
```

<210> SEQ ID NO 119
<211> LENGTH: 7
<212> TYPE: PRT
<213> ORGANISM: Artificial
<220> FEATURE:
<223> OTHER INFORMATION: synthetic peptide

<400> SEQUENCE: 119

```
Arg His Thr Leu Pro Leu His
1               5
```

<210> SEQ ID NO 120
<211> LENGTH: 7
<212> TYPE: PRT
<213> ORGANISM: Artificial
<220> FEATURE:
<223> OTHER INFORMATION: synthetic peptide

<400> SEQUENCE: 120

```
Asn Pro Gln Met Gln Arg Ser
1               5
```

<210> SEQ ID NO 121
<211> LENGTH: 7
<212> TYPE: PRT
<213> ORGANISM: Artificial
<220> FEATURE:
<223> OTHER INFORMATION: synthetic peptide

<400> SEQUENCE: 121

```
Asn Tyr Pro Thr Leu Lys Ser
1               5
```

<210> SEQ ID NO 122
<211> LENGTH: 7
<212> TYPE: PRT
<213> ORGANISM: Artificial
<220> FEATURE:
<223> OTHER INFORMATION: synthetic peptide

<400> SEQUENCE: 122

```
Asn Tyr Pro Thr Leu Lys Ser
1               5
```

<210> SEQ ID NO 123
<211> LENGTH: 7
<212> TYPE: PRT
<213> ORGANISM: Artificial
<220> FEATURE:
<223> OTHER INFORMATION: synthetic peptide

<400> SEQUENCE: 123

```
Asp Met Arg Gln Gln Arg Ser
1               5
```

<210> SEQ ID NO 124
<211> LENGTH: 7
<212> TYPE: PRT
<213> ORGANISM: Artificial
<220> FEATURE:
<223> OTHER INFORMATION: synthetic peptide

<400> SEQUENCE: 124

```
Gln Asn Pro Arg Gln Ile Tyr
```

```
<210> SEQ ID NO 125
<211> LENGTH: 7
<212> TYPE: PRT
<213> ORGANISM: Artificial
<220> FEATURE:
<223> OTHER INFORMATION: synthetic peptide

<400> SEQUENCE: 125

Gln Asn Pro Arg Gln Ile Tyr
1               5

<210> SEQ ID NO 126
<211> LENGTH: 7
<212> TYPE: PRT
<213> ORGANISM: Artificial
<220> FEATURE:
<223> OTHER INFORMATION: synthetic peptide

<400> SEQUENCE: 126

Gln Asn Pro Arg Gln Ile Tyr
1               5

<210> SEQ ID NO 127
<211> LENGTH: 7
<212> TYPE: PRT
<213> ORGANISM: Artificial
<220> FEATURE:
<223> OTHER INFORMATION: synthetic peptide

<400> SEQUENCE: 127

Gln Asn Pro Arg Gln Ile Tyr
1               5

<210> SEQ ID NO 128
<211> LENGTH: 7
<212> TYPE: PRT
<213> ORGANISM: Artificial
<220> FEATURE:
<223> OTHER INFORMATION: synthetic peptide

<400> SEQUENCE: 128

Gln Asn Pro Arg Gln Ile Tyr
1               5

<210> SEQ ID NO 129
<211> LENGTH: 7
<212> TYPE: PRT
<213> ORGANISM: Artificial
<220> FEATURE:
<223> OTHER INFORMATION: synthetic peptide

<400> SEQUENCE: 129

Gln Asn Pro Arg Gln Ile Tyr
1               5

<210> SEQ ID NO 130
<211> LENGTH: 7
<212> TYPE: PRT
<213> ORGANISM: Artificial
<220> FEATURE:
<223> OTHER INFORMATION: synthetic peptide

<400> SEQUENCE: 130

Gln Asn Pro Arg Gln Ile Tyr
1               5
```

```
<210> SEQ ID NO 131
<211> LENGTH: 7
<212> TYPE: PRT
<213> ORGANISM: Artificial
<220> FEATURE:
<223> OTHER INFORMATION: synthetic peptide

<400> SEQUENCE: 131

Gln Asn Pro Arg Gln Ile Tyr
1               5

<210> SEQ ID NO 132
<211> LENGTH: 7
<212> TYPE: PRT
<213> ORGANISM: Artificial
<220> FEATURE:
<223> OTHER INFORMATION: synthetic peptide

<400> SEQUENCE: 132

Gln Asn Pro Arg Gln Ile Tyr
1               5

<210> SEQ ID NO 133
<211> LENGTH: 7
<212> TYPE: PRT
<213> ORGANISM: Artificial
<220> FEATURE:
<223> OTHER INFORMATION: synthetic peptide

<400> SEQUENCE: 133

Gln Thr His Ser Ser Leu Trp
1               5

<210> SEQ ID NO 134
<211> LENGTH: 7
<212> TYPE: PRT
<213> ORGANISM: Artificial
<220> FEATURE:
<223> OTHER INFORMATION: synthetic peptide

<400> SEQUENCE: 134

Glu Thr Tyr Gln Gln Pro Leu
1               5

<210> SEQ ID NO 135
<211> LENGTH: 7
<212> TYPE: PRT
<213> ORGANISM: Artificial
<220> FEATURE:
<223> OTHER INFORMATION: synthetic peptide

<400> SEQUENCE: 135

Glu Thr Tyr Ala Arg Pro Leu
1               5

<210> SEQ ID NO 136
<211> LENGTH: 7
<212> TYPE: PRT
<213> ORGANISM: Artificial
<220> FEATURE:
<223> OTHER INFORMATION: synthetic peptide

<400> SEQUENCE: 136

Gly Thr Ser Arg Leu Phe Ser
1               5

<210> SEQ ID NO 137
```

```
<211> LENGTH: 7
<212> TYPE: PRT
<213> ORGANISM: Artificial
<220> FEATURE:
<223> OTHER INFORMATION: synthetic peptide

<400> SEQUENCE: 137

Leu Thr Gln Thr Leu Gln Tyr
1               5

<210> SEQ ID NO 138
<211> LENGTH: 7
<212> TYPE: PRT
<213> ORGANISM: Artificial
<220> FEATURE:
<223> OTHER INFORMATION: synthetic peptide

<400> SEQUENCE: 138

Lys Ala Phe Asp Lys His Gly
1               5

<210> SEQ ID NO 139
<211> LENGTH: 7
<212> TYPE: PRT
<213> ORGANISM: Artificial
<220> FEATURE:
<223> OTHER INFORMATION: synthetic peptide

<400> SEQUENCE: 139

Lys Pro Met Gln Phe Val His
1               5

<210> SEQ ID NO 140
<211> LENGTH: 7
<212> TYPE: PRT
<213> ORGANISM: Artificial
<220> FEATURE:
<223> OTHER INFORMATION: synthetic peptide

<400> SEQUENCE: 140

Lys Pro Met Gln Phe Val His
1               5

<210> SEQ ID NO 141
<211> LENGTH: 7
<212> TYPE: PRT
<213> ORGANISM: Artificial
<220> FEATURE:
<223> OTHER INFORMATION: synthetic peptide

<400> SEQUENCE: 141

Lys Pro Met Gln Phe Val His
1               5

<210> SEQ ID NO 142
<211> LENGTH: 7
<212> TYPE: PRT
<213> ORGANISM: Artificial
<220> FEATURE:
<223> OTHER INFORMATION: synthetic peptide

<400> SEQUENCE: 142

Pro Ala Lys Gln Lys Ala His
1               5

<210> SEQ ID NO 143
<211> LENGTH: 7
<212> TYPE: PRT
```

```
<213> ORGANISM: Artificial
<220> FEATURE:
<223> OTHER INFORMATION: synthetic peptide

<400> SEQUENCE: 143

Ser Ala Ser Gly Thr Pro Ser
1               5

<210> SEQ ID NO 144
<211> LENGTH: 7
<212> TYPE: PRT
<213> ORGANISM: Artificial
<220> FEATURE:
<223> OTHER INFORMATION: synthetic peptide

<400> SEQUENCE: 144

Ser Ser His His His Arg His
1               5

<210> SEQ ID NO 145
<211> LENGTH: 7
<212> TYPE: PRT
<213> ORGANISM: Artificial
<220> FEATURE:
<223> OTHER INFORMATION: synthetic peptide

<400> SEQUENCE: 145

Ser Ser Tyr Glu Tyr His Ala
1               5

<210> SEQ ID NO 146
<211> LENGTH: 7
<212> TYPE: PRT
<213> ORGANISM: Artificial
<220> FEATURE:
<223> OTHER INFORMATION: synthetic peptide

<400> SEQUENCE: 146

Thr Gly Pro Thr Ser Leu Ser
1               5

<210> SEQ ID NO 147
<211> LENGTH: 12
<212> TYPE: PRT
<213> ORGANISM: Artificial
<220> FEATURE:
<223> OTHER INFORMATION: synthetic peptide

<400> SEQUENCE: 147

Leu Arg Ala Phe Pro Ser Leu Pro His Thr Val Thr
1               5                   10

<210> SEQ ID NO 148
<211> LENGTH: 7
<212> TYPE: PRT
<213> ORGANISM: Artificial
<220> FEATURE:
<223> OTHER INFORMATION: synthetic peptide

<400> SEQUENCE: 148

Asn Pro Arg Ser Gln Ala Thr
1               5

<210> SEQ ID NO 149
<211> LENGTH: 7
<212> TYPE: PRT
<213> ORGANISM: Artificial
<220> FEATURE:
```

<223> OTHER INFORMATION: synthetic peptide

<400> SEQUENCE: 149

His Arg Leu Gly His Met Ser
1               5

<210> SEQ ID NO 150
<211> LENGTH: 7
<212> TYPE: PRT
<213> ORGANISM: Artificial
<220> FEATURE:
<223> OTHER INFORMATION: synthetic peptide

<400> SEQUENCE: 150

Leu Leu Pro Leu Lys Phe Lys
1               5

<210> SEQ ID NO 151
<211> LENGTH: 7
<212> TYPE: PRT
<213> ORGANISM: Artificial
<220> FEATURE:
<223> OTHER INFORMATION: synthetic peptide

<400> SEQUENCE: 151

Leu Pro Ser Ile His Asn Leu
1               5

<210> SEQ ID NO 152
<211> LENGTH: 7
<212> TYPE: PRT
<213> ORGANISM: Artificial
<220> FEATURE:
<223> OTHER INFORMATION: synthetic peptide

<400> SEQUENCE: 152

Lys Ala Thr Ile Thr Gly Met
1               5

<210> SEQ ID NO 153
<211> LENGTH: 7
<212> TYPE: PRT
<213> ORGANISM: Artificial
<220> FEATURE:
<223> OTHER INFORMATION: synthetic peptide

<400> SEQUENCE: 153

Pro Asp Ile Pro Leu Ser Arg
1               5

<210> SEQ ID NO 154
<211> LENGTH: 7
<212> TYPE: PRT
<213> ORGANISM: Artificial
<220> FEATURE:
<223> OTHER INFORMATION: synthetic peptide

<400> SEQUENCE: 154

Pro Ser Met Lys His Trp Arg
1               5

<210> SEQ ID NO 155
<211> LENGTH: 7
<212> TYPE: PRT
<213> ORGANISM: Artificial
<220> FEATURE:
<223> OTHER INFORMATION: synthetic peptide

```
<400> SEQUENCE: 155

Ser Ala Lys Gly Arg Ala Asp
1               5

<210> SEQ ID NO 156
<211> LENGTH: 7
<212> TYPE: PRT
<213> ORGANISM: Artificial
<220> FEATURE:
<223> OTHER INFORMATION: synthetic peptide

<400> SEQUENCE: 156

Ser Arg Thr Gly Ala His His
1               5

<210> SEQ ID NO 157
<211> LENGTH: 7
<212> TYPE: PRT
<213> ORGANISM: Artificial
<220> FEATURE:
<223> OTHER INFORMATION: synthetic peptide

<400> SEQUENCE: 157

Ser Lys Thr Ser Ser Thr Ser
1               5

<210> SEQ ID NO 158
<211> LENGTH: 7
<212> TYPE: PRT
<213> ORGANISM: Artificial
<220> FEATURE:
<223> OTHER INFORMATION: synthetic peptide

<400> SEQUENCE: 158

Ser Pro Asn Asn Pro Arg Glu
1               5

<210> SEQ ID NO 159
<211> LENGTH: 7
<212> TYPE: PRT
<213> ORGANISM: Artificial
<220> FEATURE:
<223> OTHER INFORMATION: synthetic peptide

<400> SEQUENCE: 159

Thr Leu Gln Arg Met Gly Gln
1               5

<210> SEQ ID NO 160
<211> LENGTH: 7
<212> TYPE: PRT
<213> ORGANISM: Artificial
<220> FEATURE:
<223> OTHER INFORMATION: synthetic peptide

<400> SEQUENCE: 160

Thr Met Thr Asn Met Ala Lys
1               5

<210> SEQ ID NO 161
<211> LENGTH: 7
<212> TYPE: PRT
<213> ORGANISM: Artificial
<220> FEATURE:
<223> OTHER INFORMATION: synthetic peptide

<400> SEQUENCE: 161
```

Thr Thr Leu Ser Pro Arg Thr
1               5

<210> SEQ ID NO 162
<211> LENGTH: 7
<212> TYPE: PRT
<213> ORGANISM: Artificial
<220> FEATURE:
<223> OTHER INFORMATION: synthetic peptide

<400> SEQUENCE: 162

Thr Thr Lys Asn Phe Asn Lys
1               5

<210> SEQ ID NO 163
<211> LENGTH: 7
<212> TYPE: PRT
<213> ORGANISM: Artificial
<220> FEATURE:
<223> OTHER INFORMATION: synthetic peptide

<400> SEQUENCE: 163

Tyr Pro Lys Ala Leu Arg Asn
1               5

<210> SEQ ID NO 164
<211> LENGTH: 7
<212> TYPE: PRT
<213> ORGANISM: Artificial
<220> FEATURE:
<223> OTHER INFORMATION: synthetic peptide

<400> SEQUENCE: 164

Val Val Lys Ser Asn Gly Glu
1               5

<210> SEQ ID NO 165
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: X is any amino acid
<220> FEATURE:
<221> NAME/KEY: VARIANT
<222> LOCATION: (4)..(4)
<223> OTHER INFORMATION: X is any amino acid

<400> SEQUENCE: 165

Xaa Ile Thr Xaa Gly Ala Tyr
1               5

<210> SEQ ID NO 166
<211> LENGTH: 7
<212> TYPE: PRT
<213> ORGANISM: Artificial
<220> FEATURE:
<223> OTHER INFORMATION: synthetic peptide

<400> SEQUENCE: 166

Leu Pro Leu Thr Pro Leu Pro
1               5

<210> SEQ ID NO 167
<211> LENGTH: 12
<212> TYPE: PRT

```
<213> ORGANISM: Artificial
<220> FEATURE:
<223> OTHER INFORMATION: synthetic peptide

<400> SEQUENCE: 167

His Ser Met Pro His Met Gly Thr Tyr Leu Leu Thr
1               5                   10

<210> SEQ ID NO 168
<211> LENGTH: 12
<212> TYPE: PRT
<213> ORGANISM: Artificial
<220> FEATURE:
<223> OTHER INFORMATION: synthetic peptide

<400> SEQUENCE: 168

Met Gln Phe Thr Pro Ala Pro Ser Pro Ser Asp His
1               5                   10

<210> SEQ ID NO 169
<211> LENGTH: 12
<212> TYPE: PRT
<213> ORGANISM: Artificial
<220> FEATURE:
<223> OTHER INFORMATION: synthetic peptide

<400> SEQUENCE: 169

Met Pro Gln Thr Leu Val Leu Pro Arg Ser Leu Leu
1               5                   10

<210> SEQ ID NO 170
<211> LENGTH: 12
<212> TYPE: PRT
<213> ORGANISM: Artificial
<220> FEATURE:
<223> OTHER INFORMATION: synthetic peptide

<400> SEQUENCE: 170

Ser Ser Thr Gln Val Gln His Thr Leu Leu Gln Thr
1               5                   10

<210> SEQ ID NO 171
<211> LENGTH: 12
<212> TYPE: PRT
<213> ORGANISM: Artificial
<220> FEATURE:
<223> OTHER INFORMATION: synthetic peptide

<400> SEQUENCE: 171

Ser Trp Pro Leu Tyr Ser Arg Asp Ser Gly Leu Gly
1               5                   10

<210> SEQ ID NO 172
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: VARIANT
<222> LOCATION: (11)..(11)
<223> OTHER INFORMATION: Xaa is any amino acid

<400> SEQUENCE: 172

Ser Val Ser Val Gly Thr Glu Ala Glu Ser Xaa Ala
1               5                   10

<210> SEQ ID NO 173
```

```
<211> LENGTH: 12
<212> TYPE: PRT
<213> ORGANISM: Artificial
<220> FEATURE:
<223> OTHER INFORMATION: synthetic peptide

<400> SEQUENCE: 173

Ser Val Ser Val Gly Met Lys Pro Ser Pro Arg Pro
1               5                   10

<210> SEQ ID NO 174
<211> LENGTH: 12
<212> TYPE: PRT
<213> ORGANISM: Artificial
<220> FEATURE:
<223> OTHER INFORMATION: synthetic peptide

<400> SEQUENCE: 174

Ser Val Ser Val Gly Met Lys Pro Ser Pro Arg Pro
1               5                   10

<210> SEQ ID NO 175
<211> LENGTH: 12
<212> TYPE: PRT
<213> ORGANISM: Artificial
<220> FEATURE:
<223> OTHER INFORMATION: synthetic peptide

<400> SEQUENCE: 175

Ser Val Ser Val Gly Met Lys Pro Ser Pro Arg Pro
1               5                   10

<210> SEQ ID NO 176
<211> LENGTH: 12
<212> TYPE: PRT
<213> ORGANISM: Artificial
<220> FEATURE:
<223> OTHER INFORMATION: synthetic peptide

<400> SEQUENCE: 176

Ser Val Ser Val Gly Met Asn Ala Glu Ser Tyr Gly
1               5                   10

<210> SEQ ID NO 177
<211> LENGTH: 12
<212> TYPE: PRT
<213> ORGANISM: Artificial
<220> FEATURE:
<223> OTHER INFORMATION: synthetic peptide

<400> SEQUENCE: 177

Thr His Pro Val Val Phe Glu Asp Glu Arg Leu Phe
1               5                   10

<210> SEQ ID NO 178
<211> LENGTH: 12
<212> TYPE: PRT
<213> ORGANISM: Artificial
<220> FEATURE:
<223> OTHER INFORMATION: synthetic peptide

<400> SEQUENCE: 178

Thr Leu Pro Ser Pro Leu Ala Leu Leu Thr Val His
1               5                   10

<210> SEQ ID NO 179
<211> LENGTH: 12
<212> TYPE: PRT
```

<213> ORGANISM: Artificial
<220> FEATURE:
<223> OTHER INFORMATION: synthetic peptide

<400> SEQUENCE: 179

Trp Pro Thr Tyr Leu Asn Pro Ser Ser Leu Lys Ala
1               5                   10

<210> SEQ ID NO 180
<211> LENGTH: 7
<212> TYPE: PRT
<213> ORGANISM: Artificial
<220> FEATURE:
<223> OTHER INFORMATION: synthetic peptide

<400> SEQUENCE: 180

Ala Ser His Asn Pro Lys Leu
1               5

<210> SEQ ID NO 181
<211> LENGTH: 7
<212> TYPE: PRT
<213> ORGANISM: Artificial
<220> FEATURE:
<223> OTHER INFORMATION: synthetic peptide

<400> SEQUENCE: 181

Pro Ala Lys Gln Lys Ala His
1               5

<210> SEQ ID NO 182
<211> LENGTH: 7
<212> TYPE: PRT
<213> ORGANISM: Artificial
<220> FEATURE:
<223> OTHER INFORMATION: synthetic peptide

<400> SEQUENCE: 182

Pro Ala Lys Gln Lys Ala His
1               5

<210> SEQ ID NO 183
<211> LENGTH: 7
<212> TYPE: PRT
<213> ORGANISM: Artificial
<220> FEATURE:
<223> OTHER INFORMATION: synthetic peptide

<400> SEQUENCE: 183

Ser Ala Ser Gly Thr Pro Ser
1               5

<210> SEQ ID NO 184
<211> LENGTH: 7
<212> TYPE: PRT
<213> ORGANISM: Artificial
<220> FEATURE:
<223> OTHER INFORMATION: synthetic peptide

<400> SEQUENCE: 184

Thr Arg Phe Tyr Asp Ser Leu
1               5

<210> SEQ ID NO 185
<211> LENGTH: 7
<212> TYPE: PRT
<213> ORGANISM: Artificial
<220> FEATURE:

```
<223> OTHER INFORMATION: synthetic peptide

<400> SEQUENCE: 185

Gln Asn Pro Arg Gln Ile Tyr
1               5

<210> SEQ ID NO 186
<211> LENGTH: 7
<212> TYPE: PRT
<213> ORGANISM: Artificial
<220> FEATURE:
<223> OTHER INFORMATION: synthetic peptide

<400> SEQUENCE: 186

Gln Asn Pro Arg Gln Ile Tyr
1               5

<210> SEQ ID NO 187
<211> LENGTH: 7
<212> TYPE: PRT
<213> ORGANISM: Artificial
<220> FEATURE:
<223> OTHER INFORMATION: synthetic peptide

<400> SEQUENCE: 187

Gln Asn Pro Arg Gln Ile Tyr
1               5

<210> SEQ ID NO 188
<211> LENGTH: 7
<212> TYPE: PRT
<213> ORGANISM: Artificial
<220> FEATURE:
<223> OTHER INFORMATION: synthetic peptide

<400> SEQUENCE: 188

Gln Asn Pro Arg Gln Ile Tyr
1               5

<210> SEQ ID NO 189
<211> LENGTH: 7
<212> TYPE: PRT
<213> ORGANISM: Artificial
<220> FEATURE:
<223> OTHER INFORMATION: synthetic peptide

<400> SEQUENCE: 189

Thr Gly Pro Thr Ser Leu Ser
1               5

<210> SEQ ID NO 190
<211> LENGTH: 7
<212> TYPE: PRT
<213> ORGANISM: Artificial
<220> FEATURE:
<223> OTHER INFORMATION: synthetic peptide

<400> SEQUENCE: 190

Thr Gly Pro Thr Ser Leu Ser
1               5

<210> SEQ ID NO 191
<211> LENGTH: 7
<212> TYPE: PRT
<213> ORGANISM: Artificial
<220> FEATURE:
<223> OTHER INFORMATION: synthetic peptide
```

<400> SEQUENCE: 191

Asn Pro Gln Met Gln Arg Ser
1               5

<210> SEQ ID NO 192
<211> LENGTH: 7
<212> TYPE: PRT
<213> ORGANISM: Artificial
<220> FEATURE:
<223> OTHER INFORMATION: synthetic peptide

<400> SEQUENCE: 192

Asn Pro Gln Met Gln Arg Ser
1               5

<210> SEQ ID NO 193
<211> LENGTH: 7
<212> TYPE: PRT
<213> ORGANISM: Artificial
<220> FEATURE:
<223> OTHER INFORMATION: synthetic peptide

<400> SEQUENCE: 193

Asn Pro Gln Met Gln Arg Ser
1               5

<210> SEQ ID NO 194
<211> LENGTH: 7
<212> TYPE: PRT
<213> ORGANISM: Artificial
<220> FEATURE:
<223> OTHER INFORMATION: synthetic peptide

<400> SEQUENCE: 194

Asn Pro Gln Met Gln Arg Ser
1               5

<210> SEQ ID NO 195
<211> LENGTH: 7
<212> TYPE: PRT
<213> ORGANISM: Artificial
<220> FEATURE:
<223> OTHER INFORMATION: synthetic peptide

<400> SEQUENCE: 195

Asn Pro Gln Met Gln Arg Ser
1               5

<210> SEQ ID NO 196
<211> LENGTH: 7
<212> TYPE: PRT
<213> ORGANISM: Artificial
<220> FEATURE:
<223> OTHER INFORMATION: synthetic peptide

<400> SEQUENCE: 196

Lys Pro Met Gln Phe Val His
1               5

<210> SEQ ID NO 197
<211> LENGTH: 7
<212> TYPE: PRT
<213> ORGANISM: Artificial
<220> FEATURE:
<223> OTHER INFORMATION: synthetic peptide

<400> SEQUENCE: 197

```
Ser Ser Tyr Glu Tyr His Ala
1               5

<210> SEQ ID NO 198
<211> LENGTH: 7
<212> TYPE: PRT
<213> ORGANISM: Artificial
<220> FEATURE:
<223> OTHER INFORMATION: synthetic peptide

<400> SEQUENCE: 198

Ser Thr Gln Ala His Pro Trp
1               5

<210> SEQ ID NO 199
<211> LENGTH: 7
<212> TYPE: PRT
<213> ORGANISM: Artificial
<220> FEATURE:
<223> OTHER INFORMATION: synthetic peptide

<400> SEQUENCE: 199

Gly Thr Ser Arg Leu Phe Ser
1               5

<210> SEQ ID NO 200
<211> LENGTH: 7
<212> TYPE: PRT
<213> ORGANISM: Artificial
<220> FEATURE:
<223> OTHER INFORMATION: synthetic peptide

<400> SEQUENCE: 200

Asn Tyr Pro Thr Leu Lys Ser
1               5

<210> SEQ ID NO 201
<211> LENGTH: 7
<212> TYPE: PRT
<213> ORGANISM: Artificial
<220> FEATURE:
<223> OTHER INFORMATION: synthetic peptide

<400> SEQUENCE: 201

Asn Tyr Pro Thr Leu Lys Ser
1               5

<210> SEQ ID NO 202
<211> LENGTH: 7
<212> TYPE: PRT
<213> ORGANISM: Artificial
<220> FEATURE:
<223> OTHER INFORMATION: synthetic peptide

<400> SEQUENCE: 202

Asn Tyr Pro Thr Leu Lys Ser
1               5

<210> SEQ ID NO 203
<211> LENGTH: 7
<212> TYPE: PRT
<213> ORGANISM: Artificial
<220> FEATURE:
<223> OTHER INFORMATION: synthetic peptide

<400> SEQUENCE: 203

Asn Tyr Pro Thr Leu Lys Ser
1               5
```

<210> SEQ ID NO 204
<211> LENGTH: 7
<212> TYPE: PRT
<213> ORGANISM: Artificial
<220> FEATURE:
<223> OTHER INFORMATION: synthetic peptide

<400> SEQUENCE: 204

Asn Tyr Pro Thr Leu Lys Ser
1               5

<210> SEQ ID NO 205
<211> LENGTH: 7
<212> TYPE: PRT
<213> ORGANISM: Artificial
<220> FEATURE:
<223> OTHER INFORMATION: synthetic peptide

<400> SEQUENCE: 205

Asn Tyr Pro Thr Leu Lys Ser
1               5

<210> SEQ ID NO 206
<211> LENGTH: 7
<212> TYPE: PRT
<213> ORGANISM: Artificial
<220> FEATURE:
<223> OTHER INFORMATION: synthetic peptide

<400> SEQUENCE: 206

Asn Tyr Pro Thr Leu Lys Ser
1               5

<210> SEQ ID NO 207
<211> LENGTH: 7
<212> TYPE: PRT
<213> ORGANISM: Artificial
<220> FEATURE:
<223> OTHER INFORMATION: synthetic peptide

<400> SEQUENCE: 207

His Ala Pro Val Gln Pro Asn
1               5

<210> SEQ ID NO 208
<211> LENGTH: 12
<212> TYPE: PRT
<213> ORGANISM: Artificial
<220> FEATURE:
<223> OTHER INFORMATION: synthetic peptide

<400> SEQUENCE: 208

Asn Pro Tyr His Pro Thr Ile Pro Gln Ser Val His
1               5                   10

<210> SEQ ID NO 209
<211> LENGTH: 12
<212> TYPE: PRT
<213> ORGANISM: Artificial
<220> FEATURE:
<223> OTHER INFORMATION: synthetic peptide

<400> SEQUENCE: 209

Asn Pro Tyr His Pro Thr Ile Pro Gln Ser Val His
1               5                   10

```
<210> SEQ ID NO 210
<211> LENGTH: 12
<212> TYPE: PRT
<213> ORGANISM: Artificial
<220> FEATURE:
<223> OTHER INFORMATION: synthetic peptide

<400> SEQUENCE: 210

Asn Pro Tyr His Pro Thr Ile Pro Gln Ser Val His
1               5                   10

<210> SEQ ID NO 211
<211> LENGTH: 12
<212> TYPE: PRT
<213> ORGANISM: Artificial
<220> FEATURE:
<223> OTHER INFORMATION: synthetic peptide

<400> SEQUENCE: 211

Asn Pro Tyr His Pro Thr Ile Pro Gln Ser Val His
1               5                   10

<210> SEQ ID NO 212
<211> LENGTH: 12
<212> TYPE: PRT
<213> ORGANISM: Artificial
<220> FEATURE:
<223> OTHER INFORMATION: synthetic peptide

<400> SEQUENCE: 212

His Gln Phe Ile Ser Pro Glu Pro Phe Leu Ile Ser
1               5                   10

<210> SEQ ID NO 213
<211> LENGTH: 12
<212> TYPE: PRT
<213> ORGANISM: Artificial
<220> FEATURE:
<223> OTHER INFORMATION: synthetic peptide

<400> SEQUENCE: 213

Ser Pro Asn Phe Ser Trp Leu Pro Leu Gly Thr Thr
1               5                   10

<210> SEQ ID NO 214
<211> LENGTH: 12
<212> TYPE: PRT
<213> ORGANISM: Artificial
<220> FEATURE:
<223> OTHER INFORMATION: synthetic peptide

<400> SEQUENCE: 214

Ser Pro Asn Phe Ser Trp Leu Pro Leu Gly Thr Thr
1               5                   10

<210> SEQ ID NO 215
<211> LENGTH: 12
<212> TYPE: PRT
<213> ORGANISM: Artificial
<220> FEATURE:
<223> OTHER INFORMATION: synthetic peptide

<400> SEQUENCE: 215

Ser Val Ser Val Gly Met Lys Pro Ser Pro Arg Pro
1               5                   10

<210> SEQ ID NO 216
<211> LENGTH: 12
```

```
<212> TYPE: PRT
<213> ORGANISM: Artificial
<220> FEATURE:
<223> OTHER INFORMATION: synthetic peptide

<400> SEQUENCE: 216

Ser Val Ser Val Gly Met Lys Pro Ser Pro Arg Pro
1               5                   10

<210> SEQ ID NO 217
<211> LENGTH: 12
<212> TYPE: PRT
<213> ORGANISM: Artificial
<220> FEATURE:
<223> OTHER INFORMATION: synthetic peptide

<400> SEQUENCE: 217

Thr Pro Leu Thr Ser Pro Ser Leu Val Arg Pro Gln
1               5                   10

<210> SEQ ID NO 218
<211> LENGTH: 12
<212> TYPE: PRT
<213> ORGANISM: Artificial
<220> FEATURE:
<223> OTHER INFORMATION: synthetic peptide

<400> SEQUENCE: 218

Thr Pro Leu Ser Tyr Leu Lys Gly Leu Val Thr Val
1               5                   10

<210> SEQ ID NO 219
<211> LENGTH: 7
<212> TYPE: PRT
<213> ORGANISM: Artificial
<220> FEATURE:
<223> OTHER INFORMATION: synthetic peptide

<400> SEQUENCE: 219

Asn Pro Met Ile Met Asn Gln
1               5

<210> SEQ ID NO 220
<211> LENGTH: 7
<212> TYPE: PRT
<213> ORGANISM: Artificial
<220> FEATURE:
<223> OTHER INFORMATION: synthetic peptide

<400> SEQUENCE: 220

Asn Pro Met Ile Met Asn Gln
1               5

<210> SEQ ID NO 221
<211> LENGTH: 7
<212> TYPE: PRT
<213> ORGANISM: Artificial
<220> FEATURE:
<223> OTHER INFORMATION: synthetic peptide

<400> SEQUENCE: 221

Asn Ile Thr Gln Leu Gly Ser
1               5

<210> SEQ ID NO 222
<211> LENGTH: 7
<212> TYPE: PRT
<213> ORGANISM: Artificial
```

```
<220> FEATURE:
<223> OTHER INFORMATION: synthetic peptide

<400> SEQUENCE: 222

His Thr Leu Leu Ser Thr Thr
1               5

<210> SEQ ID NO 223
<211> LENGTH: 7
<212> TYPE: PRT
<213> ORGANISM: Artificial
<220> FEATURE:
<223> OTHER INFORMATION: synthetic peptide

<400> SEQUENCE: 223

His Thr Leu Leu Ser Thr Thr
1               5

<210> SEQ ID NO 224
<211> LENGTH: 7
<212> TYPE: PRT
<213> ORGANISM: Artificial
<220> FEATURE:
<223> OTHER INFORMATION: synthetic peptide

<400> SEQUENCE: 224

His Thr Leu Leu Ser Thr Thr
1               5

<210> SEQ ID NO 225
<211> LENGTH: 7
<212> TYPE: PRT
<213> ORGANISM: Artificial
<220> FEATURE:
<223> OTHER INFORMATION: synthetic peptide

<400> SEQUENCE: 225

Leu Gly Pro Gly Lys Ala Phe
1               5

<210> SEQ ID NO 226
<211> LENGTH: 7
<212> TYPE: PRT
<213> ORGANISM: Artificial
<220> FEATURE:
<223> OTHER INFORMATION: synthetic peptide

<400> SEQUENCE: 226

Leu Gly Pro Gly Lys Ala Phe
1               5

<210> SEQ ID NO 227
<211> LENGTH: 7
<212> TYPE: PRT
<213> ORGANISM: Artificial
<220> FEATURE:
<223> OTHER INFORMATION: synthetic peptide

<400> SEQUENCE: 227

Leu Gly Pro Gly Lys Ala Phe
1               5

<210> SEQ ID NO 228
<211> LENGTH: 7
<212> TYPE: PRT
<213> ORGANISM: Artificial
<220> FEATURE:
<223> OTHER INFORMATION: synthetic peptide
```

<400> SEQUENCE: 228

Leu Gly Pro Gly Lys Ala Phe
1               5

<210> SEQ ID NO 229
<211> LENGTH: 7
<212> TYPE: PRT
<213> ORGANISM: Artificial
<220> FEATURE:
<223> OTHER INFORMATION: synthetic peptide

<400> SEQUENCE: 229

Lys Thr Ser Ser Trp Ala Asn
1               5

<210> SEQ ID NO 230
<211> LENGTH: 7
<212> TYPE: PRT
<213> ORGANISM: Artificial
<220> FEATURE:
<223> OTHER INFORMATION: synthetic peptide

<400> SEQUENCE: 230

Lys Met Asn His Met Pro Asn
1               5

<210> SEQ ID NO 231
<211> LENGTH: 7
<212> TYPE: PRT
<213> ORGANISM: Artificial
<220> FEATURE:
<223> OTHER INFORMATION: synthetic peptide

<400> SEQUENCE: 231

Ser Leu Leu Thr Pro Trp Leu
1               5

<210> SEQ ID NO 232
<211> LENGTH: 7
<212> TYPE: PRT
<213> ORGANISM: Artificial
<220> FEATURE:
<223> OTHER INFORMATION: synthetic peptide

<400> SEQUENCE: 232

Thr Leu Gly Leu Pro Met Leu
1               5

<210> SEQ ID NO 233
<211> LENGTH: 7
<212> TYPE: PRT
<213> ORGANISM: Artificial
<220> FEATURE:
<223> OTHER INFORMATION: synthetic peptide

<400> SEQUENCE: 233

Thr Gly Leu Ala Lys Thr Ala
1               5

<210> SEQ ID NO 234
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: VARIANT

```
<222> LOCATION: (3)..(3)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is any amino acid

<400> SEQUENCE: 234

Ile Arg Xaa Leu Xaa Ile Ser
1               5

<210> SEQ ID NO 235
<211> LENGTH: 7
<212> TYPE: PRT
<213> ORGANISM: Artificial
<220> FEATURE:
<223> OTHER INFORMATION: synthetic peptide

<400> SEQUENCE: 235

Leu Gly Pro Gly Lys Ala Phe
1               5

<210> SEQ ID NO 236
<211> LENGTH: 7
<212> TYPE: PRT
<213> ORGANISM: Artificial
<220> FEATURE:
<223> OTHER INFORMATION: synthetic peptide

<400> SEQUENCE: 236

Leu Gly Pro Gly Lys Ala Phe
1               5

<210> SEQ ID NO 237
<211> LENGTH: 7
<212> TYPE: PRT
<213> ORGANISM: Artificial
<220> FEATURE:
<223> OTHER INFORMATION: synthetic peptide

<400> SEQUENCE: 237

Leu Gly Pro Gly Lys Ala Phe
1               5

<210> SEQ ID NO 238
<211> LENGTH: 12
<212> TYPE: PRT
<213> ORGANISM: Artificial
<220> FEATURE:
<223> OTHER INFORMATION: synthetic peptide

<400> SEQUENCE: 238

Asp Leu Asn Tyr Phe Thr Leu Ser Ser Lys Arg Glu
1               5                   10

<210> SEQ ID NO 239
<211> LENGTH: 12
<212> TYPE: PRT
<213> ORGANISM: Artificial
<220> FEATURE:
<223> OTHER INFORMATION: synthetic peptide

<400> SEQUENCE: 239

Asp Leu Asn Tyr Phe Thr Leu Ser Ser Lys Arg Glu
1               5                   10

<210> SEQ ID NO 240
<211> LENGTH: 12
```

```
<212> TYPE: PRT
<213> ORGANISM: Artificial
<220> FEATURE:
<223> OTHER INFORMATION: synthetic peptide

<400> SEQUENCE: 240

Thr Met Gly Phe Thr Ala Pro Arg Phe Pro His Tyr
1               5                   10

<210> SEQ ID NO 241
<211> LENGTH: 12
<212> TYPE: PRT
<213> ORGANISM: Artificial
<220> FEATURE:
<223> OTHER INFORMATION: synthetic peptide

<400> SEQUENCE: 241

Thr Met Gly Phe Thr Ala Pro Arg Phe Pro His Tyr
1               5                   10

<210> SEQ ID NO 242
<211> LENGTH: 12
<212> TYPE: PRT
<213> ORGANISM: Artificial
<220> FEATURE:
<223> OTHER INFORMATION: synthetic peptide

<400> SEQUENCE: 242

Thr Met Gly Phe Thr Ala Pro Arg Phe Pro His Tyr
1               5                   10

<210> SEQ ID NO 243
<211> LENGTH: 12
<212> TYPE: PRT
<213> ORGANISM: Artificial
<220> FEATURE:
<223> OTHER INFORMATION: synthetic peptide

<400> SEQUENCE: 243

Thr Met Gly Phe Thr Ala Pro Arg Phe Pro His Tyr
1               5                   10

<210> SEQ ID NO 244
<211> LENGTH: 7
<212> TYPE: PRT
<213> ORGANISM: Artificial
<220> FEATURE:
<223> OTHER INFORMATION: synthetic peptide

<400> SEQUENCE: 244

His Thr Leu Leu Ser Thr Thr
1               5

<210> SEQ ID NO 245
<211> LENGTH: 7
<212> TYPE: PRT
<213> ORGANISM: Artificial
<220> FEATURE:
<223> OTHER INFORMATION: synthetic peptide

<400> SEQUENCE: 245

His Thr Leu Leu Ser Thr Thr
1               5

<210> SEQ ID NO 246
<211> LENGTH: 7
<212> TYPE: PRT
<213> ORGANISM: Artificial
```

```
<220> FEATURE:
<223> OTHER INFORMATION: synthetic peptide

<400> SEQUENCE: 246

Leu Ala Ser Thr Thr His Val
1               5

<210> SEQ ID NO 247
<211> LENGTH: 7
<212> TYPE: PRT
<213> ORGANISM: Artificial
<220> FEATURE:
<223> OTHER INFORMATION: synthetic peptide

<400> SEQUENCE: 247

Leu Gly Pro Gly Lys Ala Phe
1               5

<210> SEQ ID NO 248
<211> LENGTH: 7
<212> TYPE: PRT
<213> ORGANISM: Artificial
<220> FEATURE:
<223> OTHER INFORMATION: synthetic peptide

<400> SEQUENCE: 248

Leu Gly Pro Gly Lys Ala Phe
1               5

<210> SEQ ID NO 249
<211> LENGTH: 7
<212> TYPE: PRT
<213> ORGANISM: Artificial
<220> FEATURE:
<223> OTHER INFORMATION: synthetic peptide

<400> SEQUENCE: 249

Leu Gly Pro Gly Lys Ala Phe
1               5

<210> SEQ ID NO 250
<211> LENGTH: 7
<212> TYPE: PRT
<213> ORGANISM: Artificial
<220> FEATURE:
<223> OTHER INFORMATION: synthetic peptide

<400> SEQUENCE: 250

Ser Leu Leu Thr Pro Trp Leu
1               5

<210> SEQ ID NO 251
<211> LENGTH: 7
<212> TYPE: PRT
<213> ORGANISM: Artificial
<220> FEATURE:
<223> OTHER INFORMATION: synthetic peptide

<400> SEQUENCE: 251

Asn Glu Arg Gln Met Glu Leu
1               5

<210> SEQ ID NO 252
<211> LENGTH: 7
<212> TYPE: PRT
<213> ORGANISM: Artificial
<220> FEATURE:
<223> OTHER INFORMATION: synthetic peptide
```

<400> SEQUENCE: 252

Asn Lys Pro Leu Ser Thr Leu
1               5

<210> SEQ ID NO 253
<211> LENGTH: 7
<212> TYPE: PRT
<213> ORGANISM: Artificial
<220> FEATURE:
<223> OTHER INFORMATION: synthetic peptide

<400> SEQUENCE: 253

His Thr Leu Leu Ser Thr Thr
1               5

<210> SEQ ID NO 254
<211> LENGTH: 7
<212> TYPE: PRT
<213> ORGANISM: Artificial
<220> FEATURE:
<223> OTHER INFORMATION: synthetic peptide

<400> SEQUENCE: 254

Leu Lys Pro Phe Ser Gly Ala
1               5

<210> SEQ ID NO 255
<211> LENGTH: 7
<212> TYPE: PRT
<213> ORGANISM: Artificial
<220> FEATURE:
<223> OTHER INFORMATION: synthetic peptide

<400> SEQUENCE: 255

Leu Gly Pro Gly Lys Ala Phe
1               5

<210> SEQ ID NO 256
<211> LENGTH: 7
<212> TYPE: PRT
<213> ORGANISM: Artificial
<220> FEATURE:
<223> OTHER INFORMATION: synthetic peptide

<400> SEQUENCE: 256

Leu Gly Pro Gly Lys Ala Phe
1               5

<210> SEQ ID NO 257
<211> LENGTH: 7
<212> TYPE: PRT
<213> ORGANISM: Artificial
<220> FEATURE:
<223> OTHER INFORMATION: synthetic peptide

<400> SEQUENCE: 257

Leu Gly Pro Gly Lys Ala Phe
1               5

<210> SEQ ID NO 258
<211> LENGTH: 7
<212> TYPE: PRT
<213> ORGANISM: Artificial
<220> FEATURE:
<223> OTHER INFORMATION: synthetic peptide

<400> SEQUENCE: 258

Leu Gly Pro Gly Lys Ala Phe
1               5

<210> SEQ ID NO 259
<211> LENGTH: 7
<212> TYPE: PRT
<213> ORGANISM: Artificial
<220> FEATURE:
<223> OTHER INFORMATION: synthetic peptide

<400> SEQUENCE: 259

Ser Thr Ser Ala Lys His Trp
1               5

<210> SEQ ID NO 260
<211> LENGTH: 12
<212> TYPE: PRT
<213> ORGANISM: Artificial
<220> FEATURE:
<223> OTHER INFORMATION: synthetic peptide

<400> SEQUENCE: 260

Thr Met Gly Phe Thr Ala Pro Arg Phe Pro His Tyr
1               5                   10

<210> SEQ ID NO 261
<211> LENGTH: 12
<212> TYPE: PRT
<213> ORGANISM: Artificial
<220> FEATURE:
<223> OTHER INFORMATION: synthetic peptide

<400> SEQUENCE: 261

Thr Met Gly Phe Thr Ala Pro Arg Phe Pro His Tyr
1               5                   10

<210> SEQ ID NO 262
<211> LENGTH: 12
<212> TYPE: PRT
<213> ORGANISM: Artificial
<220> FEATURE:
<223> OTHER INFORMATION: synthetic peptide

<400> SEQUENCE: 262

Thr Met Gly Phe Thr Ala Pro Arg Phe Pro His Tyr
1               5                   10

<210> SEQ ID NO 263
<211> LENGTH: 12
<212> TYPE: PRT
<213> ORGANISM: Artificial
<220> FEATURE:
<223> OTHER INFORMATION: synthetic peptide

<400> SEQUENCE: 263

Thr Met Gly Phe Thr Ala Pro Arg Phe Pro His Tyr
1               5                   10

<210> SEQ ID NO 264
<211> LENGTH: 12
<212> TYPE: PRT
<213> ORGANISM: Artificial
<220> FEATURE:
<223> OTHER INFORMATION: synthetic peptide

<400> SEQUENCE: 264

Thr Met Gly Phe Thr Ala Pro Arg Phe Pro His Tyr

```
1               5                  10
```

<210> SEQ ID NO 265
<211> LENGTH: 12
<212> TYPE: PRT
<213> ORGANISM: Artificial
<220> FEATURE:
<223> OTHER INFORMATION: synthetic peptide

<400> SEQUENCE: 265

```
Thr Met Gly Phe Thr Ala Pro Arg Phe Pro His Tyr
1               5                  10
```

<210> SEQ ID NO 266
<211> LENGTH: 12
<212> TYPE: PRT
<213> ORGANISM: Artificial
<220> FEATURE:
<223> OTHER INFORMATION: synthetic peptide

<400> SEQUENCE: 266

```
Thr Met Gly Phe Thr Ala Pro Arg Phe Pro His Tyr
1               5                  10
```

<210> SEQ ID NO 267
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (1)..(9)

<400> SEQUENCE: 267

```
Cys Asn Tyr Pro Thr Leu Lys Ser Cys
1               5
```

<210> SEQ ID NO 268
<211> LENGTH: 36
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:

```
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp

<400> SEQUENCE: 268

Pro Xaa Gly Pro Xaa Gly Pro Xaa Gly Pro Xaa Gly Pro Xaa Gly Pro
1               5                   10                  15

Xaa Ala Pro Xaa Gly Pro Xaa Gly Pro Xaa Gly Pro Xaa Gly Pro Xaa
            20                  25                  30

Gly Pro Xaa Gly
        35

<210> SEQ ID NO 269
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: DOMAIN
<222> LOCATION: (13)..(16)
<223> OTHER INFORMATION: Linker sequence that links the peptide to
      biotin

<400> SEQUENCE: 269

Asn Pro Tyr His Pro Thr Ile Pro Gln Ser Val His Gly Gly Gly Lys
1               5                   10                  15

<210> SEQ ID NO 270
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: DOMAIN
<222> LOCATION: (13)..(16)
<223> OTHER INFORMATION: Linker sequence that links the peptide to
      biotin

<400> SEQUENCE: 270

Asn Pro Asp His Pro Asp Ile Pro Gln Asp Val His Gly Gly Gly Lys
1               5                   10                  15

<210> SEQ ID NO 271
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: DOMAIN
<222> LOCATION: (13)..(16)
<223> OTHER INFORMATION: Linker sequence that links the peptide to
      biotin
```

-continued

```
<400> SEQUENCE: 271

Asn Pro Tyr His Pro Thr Ile Pro Gln Ser Val His Gly Gly Gly Lys
1               5                   10                  15

<210> SEQ ID NO 272
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: DOMAIN
<222> LOCATION: (13)..(16)
<223> OTHER INFORMATION: Linker sequence that links the peptide to
      biotin

<400> SEQUENCE: 272

Asn Pro Tyr Ala Pro Thr Ile Pro Gln Ser Val Ala Gly Gly Gly Lys
1               5                   10                  15

<210> SEQ ID NO 273
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: DOMAIN
<222> LOCATION: (13)..(16)
<223> OTHER INFORMATION: Linker sequence that links the peptide to
      biotin

<400> SEQUENCE: 273

Ala Pro Tyr His Pro Thr Ile Pro Ala Ser Val His Gly Gly Gly Lys
1               5                   10                  15
```

HYDROXYAPATITE-BINDING PEPTIDES FOR BONE GROWTH AND INHIBITION

CROSS-REFERENCE TO RELATED APPLICATIONS

This application claims priority to International Application No. PCT/US2005/043214, filed Nov. 29, 2005, which claims priority to U.S. Provisional Patent Application No. 60/631,660, filed on Nov. 29, 2004, which are hereby incorporated by reference in its entirety.

STATEMENT OF GOVERNMENTAL SUPPORT

This invention was made during work supported by U.S. Department of Energy under Contract Nos. DE-AC03-76SF00098 and DE-AC02-05CH11231. The government has certain rights in this invention.

BACKGROUND OF THE INVENTION

1. Field of the Invention

The present invention generally relates to the field of artificial bone synthesis based on hydroxyapatite binding sequences and peptides.

2. Related Art

A fundamental challenge in the field of biomineralization is to identify the short protein motifs which can specifically nucleate on or bind to the target materials. Although various protein matrices including collagens, osteopontin, and enamelogenin found in bone and dentin have been extensively studied and shown for specific nucleation of the target inorganic biominerals, understanding of the role of specific protein motifs are still limited. See L. Addadi, S. Weiner, *Angew. Chem. Int. Ed. Engl.* 31, 153 (1992); S. Weiner, L. Addadi, *J. Mater. Chem.* 7, 689 (1997); G. He, T. Dahl, A. Veis, A. George, *Nat. Mater.* 2. 552 (2003); C. E. Ye, K. R. Rattray, K. J. Warne, J. Gordon, J. Sodek, G. K. Hunter, H. Goldberg, *J Bio. Chem.* 278, 7949 (2003); and S. Mann, *Biomimetic Materials Chemistry*; VCH: New York, (1996). The long encrypted peptide chains hinder direct incorporation of protein matrices into functional building blocks in organic/inorganic hybrid composite materials.

One of the most promising methods to identify the specific short peptide binding motifs against the unknown inorganic or organic surfaces is phage display. See Whaley, S. R.; English, D. S.; Hu, E. L. Barbara, P. F. Belcher, A. M. *Nature* 405, 665 (2000) and Lee, S.-W.; Mao, C.; Flynn, C. E.; Belcher, A. M., *Science*, 296, 892 (2002). Phage display is a directed evolution process for identifying short peptide binding motifs against target materials. These binding peptides can potentially template the nucleation and growth of magnetic, optical, electrical materials, self-assemble these materials in various environments, or make them biocompatible. See C. Mao, D. Solis, B. Reiss, S. Kottmann, R. Sweeney, A. Hayhurst, G. Georgiou, B. Iverson, A. Belcher, Science, 303, 213 (2004); B. Reiss, C. Mao, D. Solis, K. Ryan, T. Thomson, A. Belcher, *Nano Lett.*, 4, 1127 (2004). Phage display peptide libraries have emerged as a powerful method in identifying such peptide agonists and antagonists. See, for example, Scott et al. (1990), Science 249: 386; Devlin et al. (1990), Science 249: 404; U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference).

In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. The peptide sequences may also suggest which residues may be safely replaced by alanine scanning or by mutagenesis at the DNA level. Mutagenesis libraries may be created and screened to further optimize the sequence of the best binders. See Lowman (1997), *Ann. Rev. Biophys. Biomol. Struct.* 26: 401-24.

SUMMARY OF THE INVENTION

The invention provides for a composition comprising a peptide having a hydroxyapatite (HA)-binding activity comprising an amino acid sequence having a percent homology of at least 20% with an amino acid sequence selected from the group consisting of SEQ ID NOS: 1-267.

The invention also provides for an implantable bone growth inducing composition comprising: a matrix and at least one amino acid sequence selected from the group consisting of SEQ ID NOs: 1-267, attached thereto.

The invention further provides for a method for inhibiting mineral growth in bone, ligament, or cartilage in a mammal comprising administering to said mammal a composition comprising a pharmacologically effective amount of SEQ ID NOS: 1-267 in combination with a pharmaceutically acceptable delivery vehicle.

The invention further provides for an osteogenic device for implantation in a mammal, the device comprising: an osteogenic peptide dispersed or attached within a biocompatible, in vivo biodegradable matrix, wherein said osteogenic peptide comprises at least one of the amino acid sequences of SEQ ID NOS: 1-267.

The invention also provides for a method for directed mineral nucleation or mineralization comprising the steps of: attaching an amino acid sequence to a polymeric organic material to create a mineralized material precursor, wherein the amino acid sequence directs mineralization on the mineralized material precursor.

The invention also provides for a method for synthesizing an implantable article, comprising the steps of: attaching a biocompatible substrate with a polypeptide having a sequence selected from SEQ ID NOS: 1-267.

BRIEF DESCRIPTION OF THE DRAWINGS

FIG. 1 shows schematically the procedure used to identify hydroxyapatite (HA) binding peptides by phage display (Panel A) and the genetically engineered virus used (Panel B).

FIG. 2 shows the virus templated nanocrystal synthesis.

FIG. 3 shows SEM images of polycrystalline (Panel A) and single crystalline hydroxyapatite (Panel B) (scale bars: 20 µm).

FIG. 4 shows the M13 phage libraries used for identification of HA binding peptides.

FIG. 5 shows the binding peptide sequences identified by phage display, along with their characteristics, after the fourth round selection against the single crystal HA (Panel A) and polycrystalline HA (Panel B).

FIG. 6 shows further binding peptide sequences identified by phage display, along with their characteristics, after the fourth round selection against the single crystal HA.

FIG. 7 shows the DNA analysis of randomly selected phages from the 1st round selection against single crystal HA.

FIG. 8 shows the DNA analysis of randomly selected phages from the 2nd round selection against single crystal HA.

FIG. 9 shows the DNA analysis of randomly selected phages from the 3rd round of selection against single crystal HA.

FIG. 10 shows the DNA analysis of randomly selected phages from the 4th round of selection against single crystal HA.

FIG. 11 shows the DNA analysis of randomly selected phages from the 4th round selection against the polycrystalline HA (Panel E).

FIG. 12 shows the results of the binding assay: (Panel A) flow cytometric measurement of fluorescence intensities of HA binding viruses verse wild type viruses, (Panel B) phage titering assay to count the number of eluted phage from HA targets. Single crystalline and polycrystalline HA were freshly etched to remove carbonated contaminates and incubated with $1\times10^{10}$ pfu of phage of W4a-4-14 (Single 14), W4a-4-15 (single 15), HA-4-3 (poly 3), wild type (wild) phages suspension for these assays.

FIG. 13 shows the optical (left panels) and fluorescence (right panels) micrographs of HA crystals bound with phages containing single 14 peptide (Panel A), single 15 peptide (Panel B), poly 3 peptide (Panel C), and wild type (Panel D). The HA-binding phage was labeled with R-phycoerythrin-labeled monoclonal pVIII antibody.

FIG. 14 shows SEM micrographs of the single crystal HA and schematics of 3-D HA crystal structures viewed from various angles.

FIG. 15 shows the experimentally measured zeta potential of HA at pH 7.5 is negative (=−11.45±1.49) consistent with the net negatively charged a, b faces suggested by the HA crystal structure.

FIG. 16 shows a ball-stick model of the lowest energy conformation of single 15 HA-binding peptide obtained by computer simulations to show that the distances between alpha carbons of the hydroxylated/amide residues closely match the lattice parameters of the HA crystal face.

FIG. 17 shows a ball-stick model of the lowest energy conformation of a single 15 HA-binding peptide obtained by molecular mechanics simulation and shows that the distances between the oxygens in hydroxyl residues are 10.66 Å ($O_{Ser}$-$O_{Thr}$) and 10.07 Å ($O_{Tyr}$-$O_{Thr}$) and closely match unit cell distance of single crystal HA on (100) face (9.42 Å) and with those of the neighboring hydroxyproline residues (10.10±0.84 Å) in collagen.

FIG. 18 shows the CD spectra of single 15 peptide (HA), scrambled single 15 peptide (Ile and Pro switched) (PxI), and single 15 peptide with aspartic acid substituted at positions 3, 6 and 10 (Panel E). The graph shows that peptide does not have any specific alpha helix or beta sheet structures.

FIG. 19 shows a schematic of the procedure used in peptide templated HA nucleation on a holey carbon TEM grid, in accordance with one embodiment of the present invention.

FIG. 20 shows concentration and time dependence of HA-mineralization templated by HA-binding peptide single 15-biotin (NPYHPTIPQSVH-GGGK-biotin; SEQ ID NO: 269). Panels A and B show TEM images of HA growth templated by 1.5 mg/ml and 15 mg/ml, respectively, single 15-biotin peptide, two hours after incubation with mineral solutions ($CaCl_2$ (10 mM)+$Na_2HPO_4$ (5 mM)→$Ca_{10}(OH)_2(PO_4)_6$). Panels C, D and E show TEM images collected 30 min, one hour, and two hours, respectively, after initiating HA-biomineralization templated by the HA-binding single 15-biotin peptide. ($CaCl_2$ (10 mM)+$Na_2HPO_4$ (5 mM)→$Ca_{10}(OH)_2(PO_4)_6$). The inset photographs show the X-ray diffraction patterns of the crystals at each timepoint.

FIG. 21 shows the electron micrographs of HA growth templated by the major 12-mer HA-binding peptide single 15-biotin: TEM image and selected area diffraction pattern (inset) (Panel A) and SEM image (Panel B).

FIG. 22, Panel A shows a high-resolution TEM image of HA growth templated by single 15-biotin peptide after 2 h showing the spacing of 0.26 nm, which matches the spacing of the 202 face of the HA crystal lattices. FIG. 22, Panel B shows an SEM-associated EDS area analysis of a cross-section of the crystal resulted from single 15-biotin peptide-templated HA nucleation showing that the ratio of calcium to phosphate is that of HA.

FIG. 23 shows the electron micrographs of control HA nucleation experiment without any templating peptide, where 5 μl of 5 mM $Na_2HPO_4$ and 5 μl of 10 mM $CaCl_2$ were deposited on the holey carbon film of TEM grid and incubated for up to two hours. Panel A is TEM. Panel B is a SEM. TEM samples collected after two hours showed little deposition of crystals on TEM grids (Panel A). When the mineralization control experiment without templating peptides was performed on a gold substrate, amorphous calcium phosphate deposition was observed.

FIG. 24 shows the control HA growth templated by the variations of the HA-binding peptide single 15-biotin to show that each specific residue is critical for HA-binding. The experimental conditions for the control HA-nucleation are: 1.5 mg/ml control peptide solutions were applied.

FIG. 25 shows the control HA growth templated by the variations of the HA-binding peptide single 15-biotin to show that each specific residue is critical for HA-binding. Panels A and B show TEM images showing HA growth templated by peptide 1 and peptide 2, respectively. TEM image of Panel A shows nucleation after switching the proline and isoleucine at positions 2 and 7 of single 15-biotin. TEM image of Panel B shows nucleation after substituting 3Tyr, 6Thr, and 10Ser of single 15-biotin with aspartic acid. Panel C shows TEM image showing HA growth templated by peptide 3 after substituting 3Tyr, 6Thr, and 10Ser of single 15-biotin with alanine.

FIG. 26 shows the control HA growth templated by the variations of the HA-binding peptide single 15-biotin to show that each specific residue is critical for HA-binding. Panels A and B shows TEM images showing HA growth templated by peptide 4 (with alanine substitution of the histidines of single 15-biotin) and peptide 5 (with alanine substitution of 1Asn and 9Gln of single 15-biotin), respectively.

DETAILED DESCRIPTION OF THE PREFERRED EMBODIMENT

The term "peptide" herein refers to an amino acid sequence between 2 and 100 amino acids in length, the amino acids being joined by peptide linkages. The amino acids may be naturally and non-naturally occurring.

The terms "derived from" or "based on" herein refers to, regarding a peptide amino acid sequence, having a relationship to a HA-binding sequence described herein.

The term "substantially identical" herein refers to an amino acid sequence which differs from another amino acid sequence only by amino acid substitutions, deletions, or insertions that do not destroy the HA-binding or nucleation activity of the peptide. It also includes peptides or sequences containing the HA-binding motif.

Figure 13:
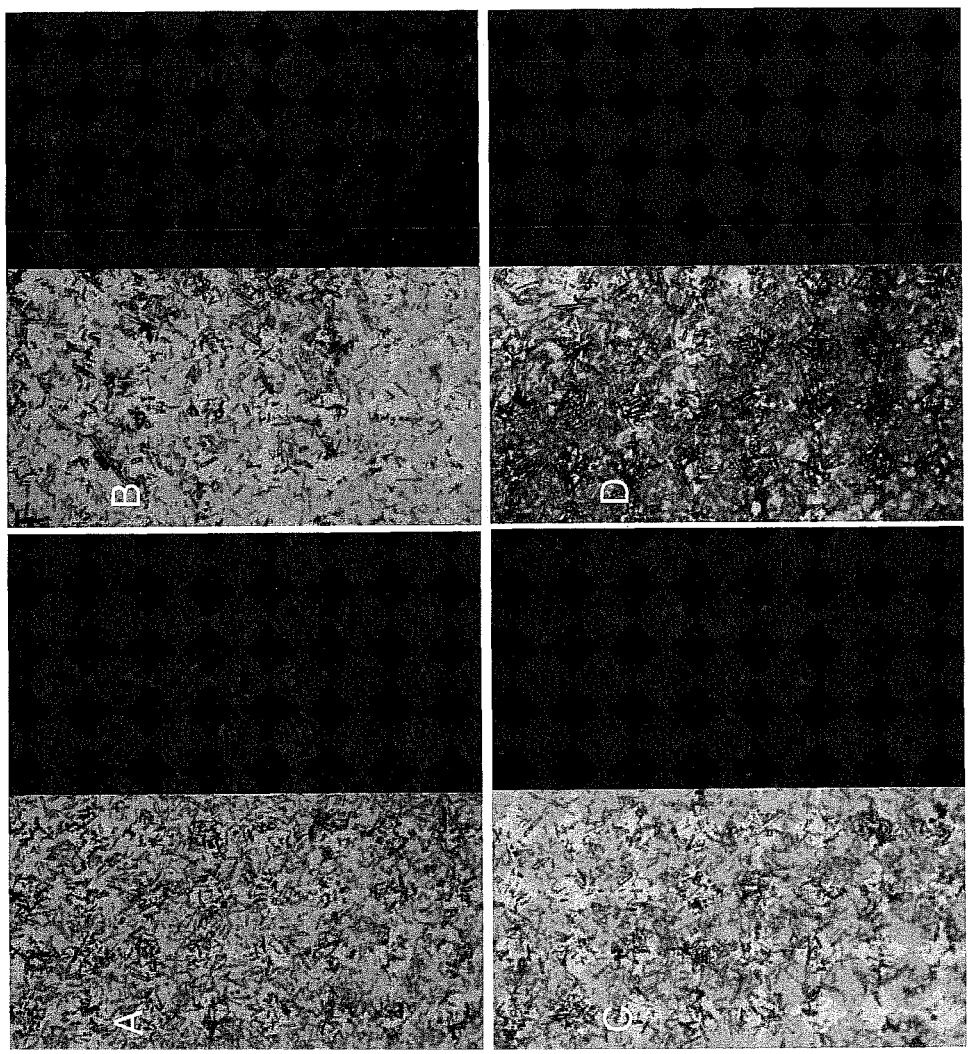
Figure 14:
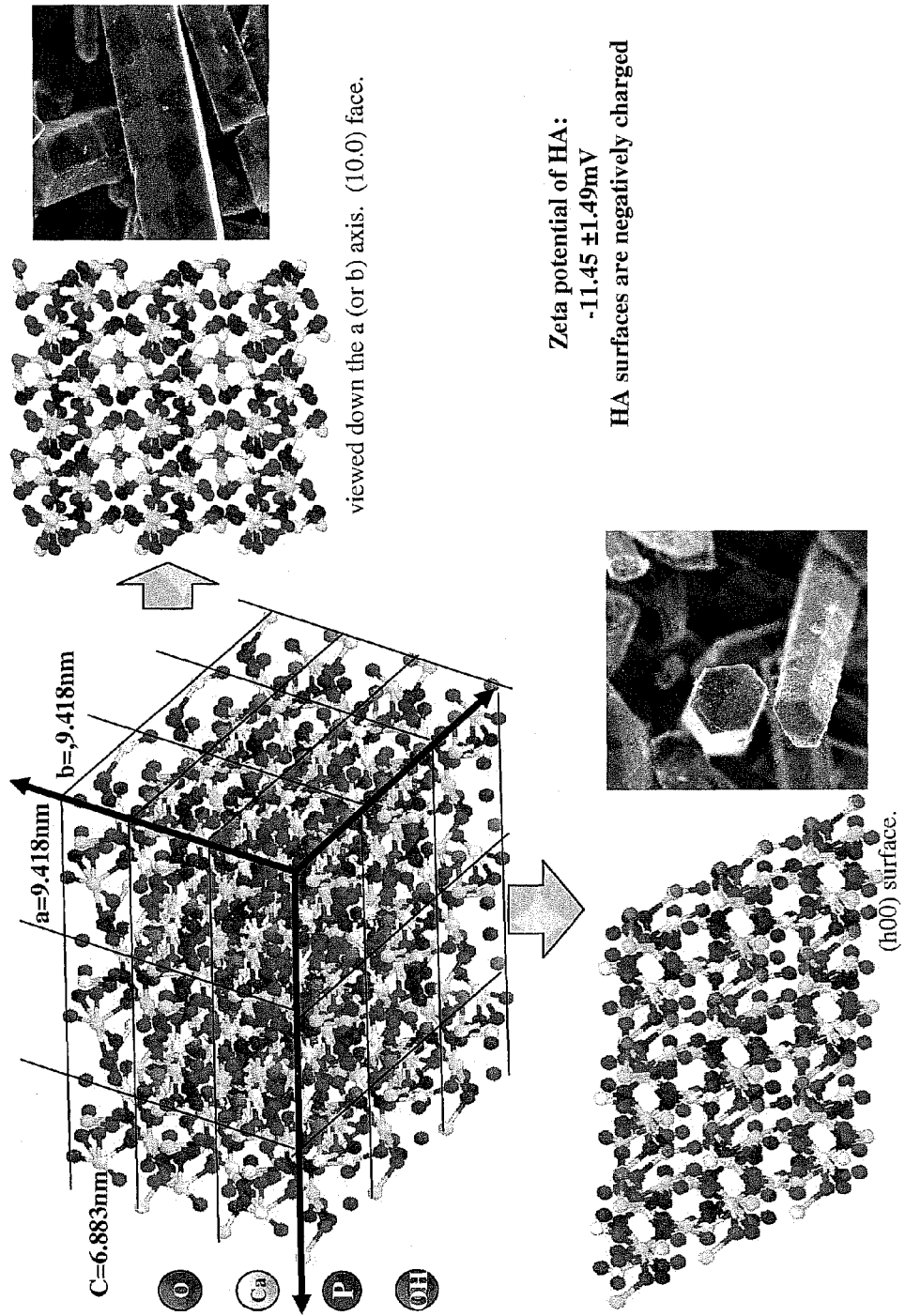
Figure 15:
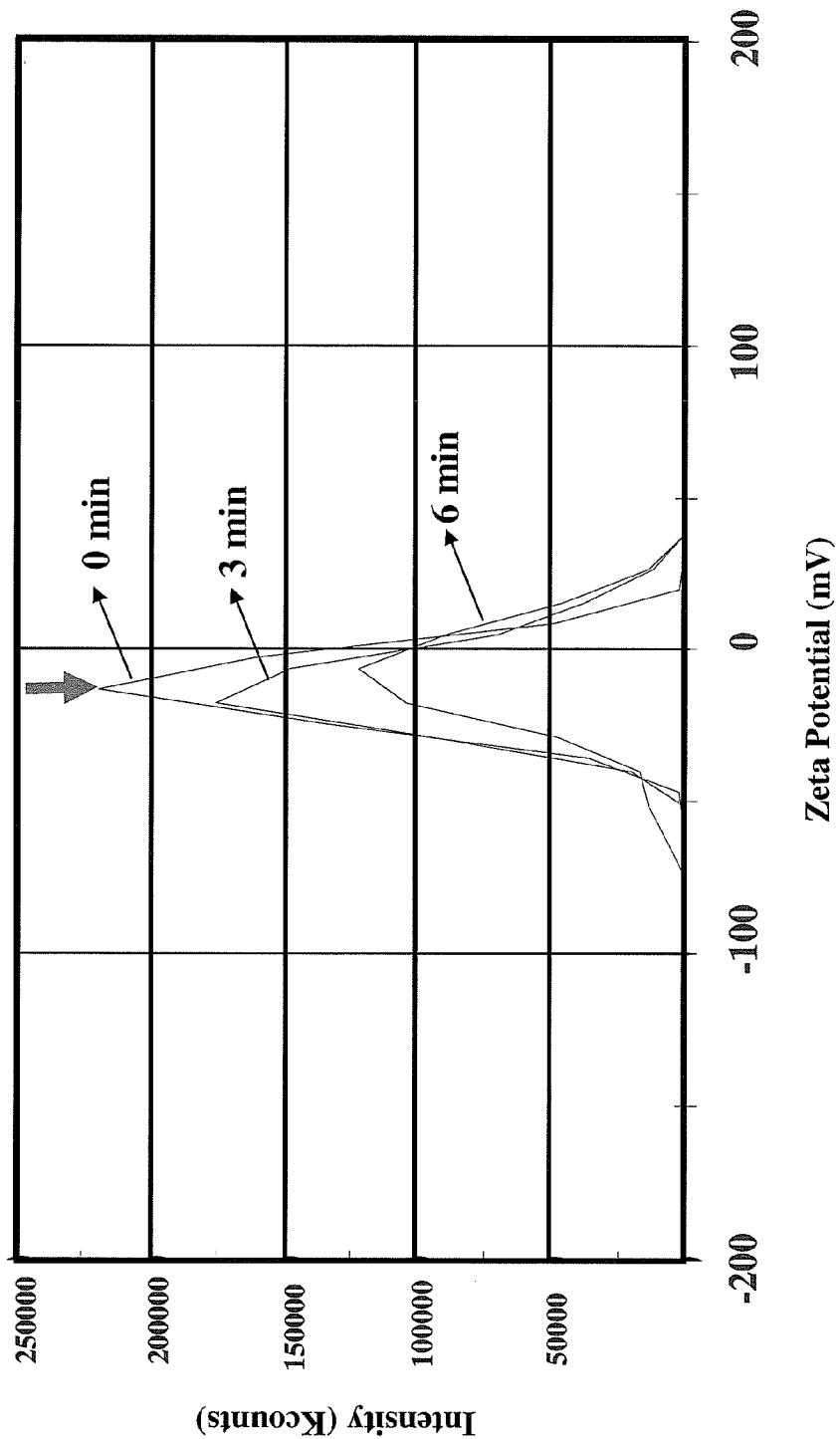
Figure 16:
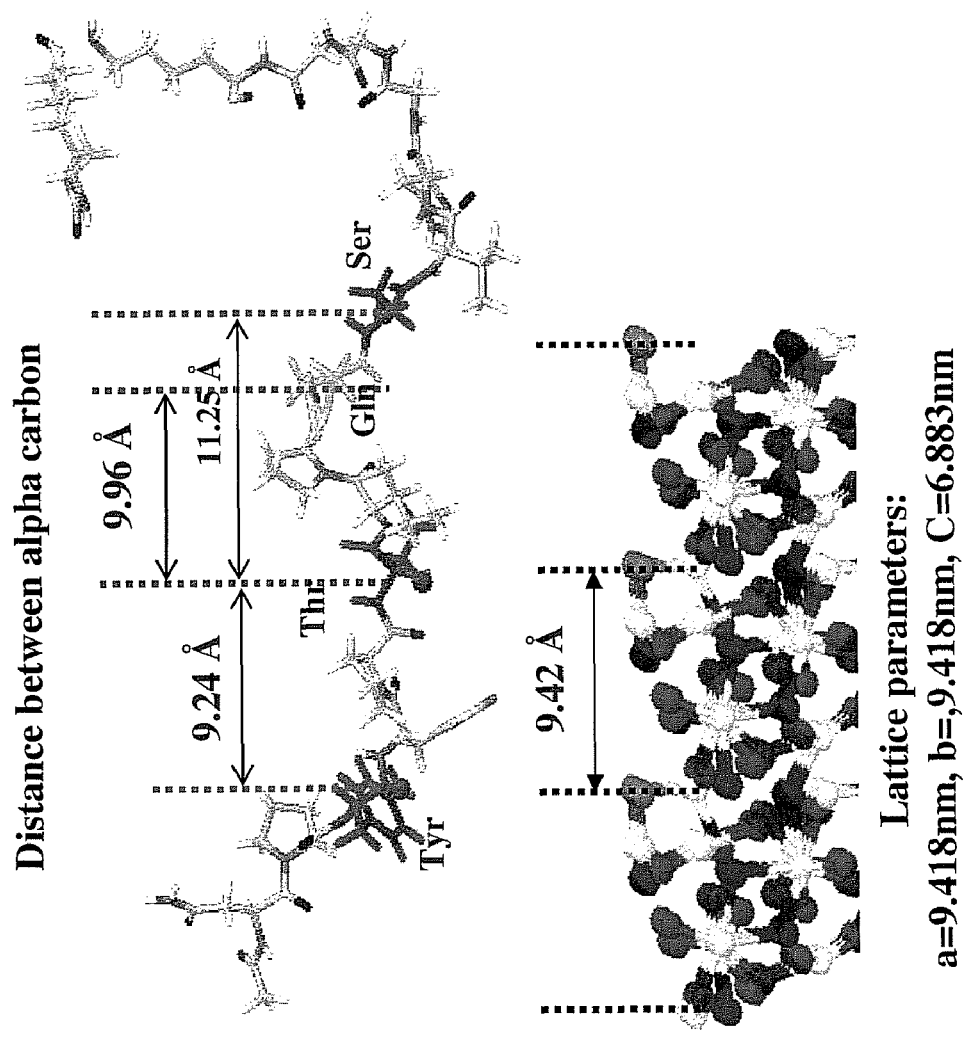
Figure 17:
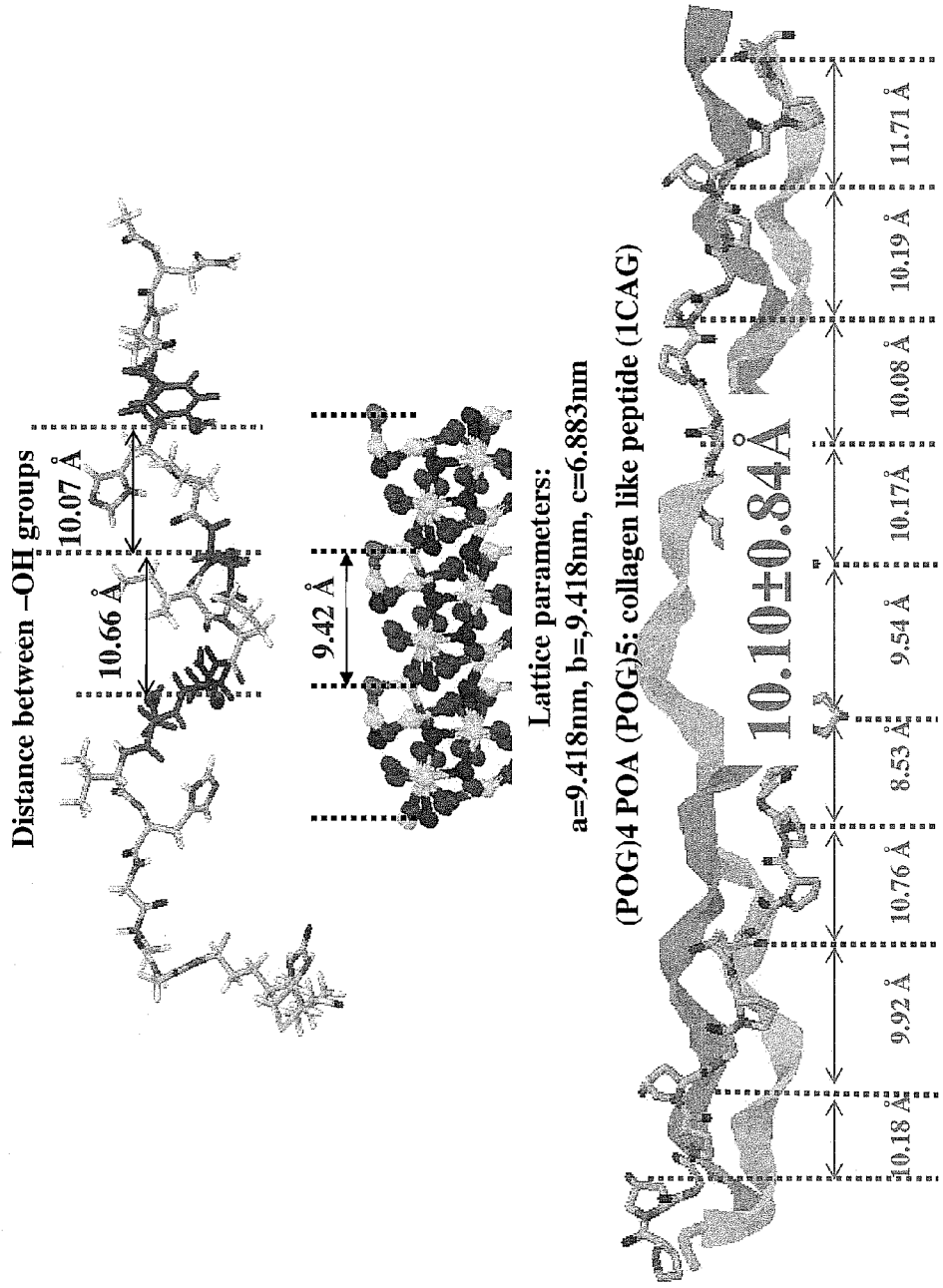
Figure 18:
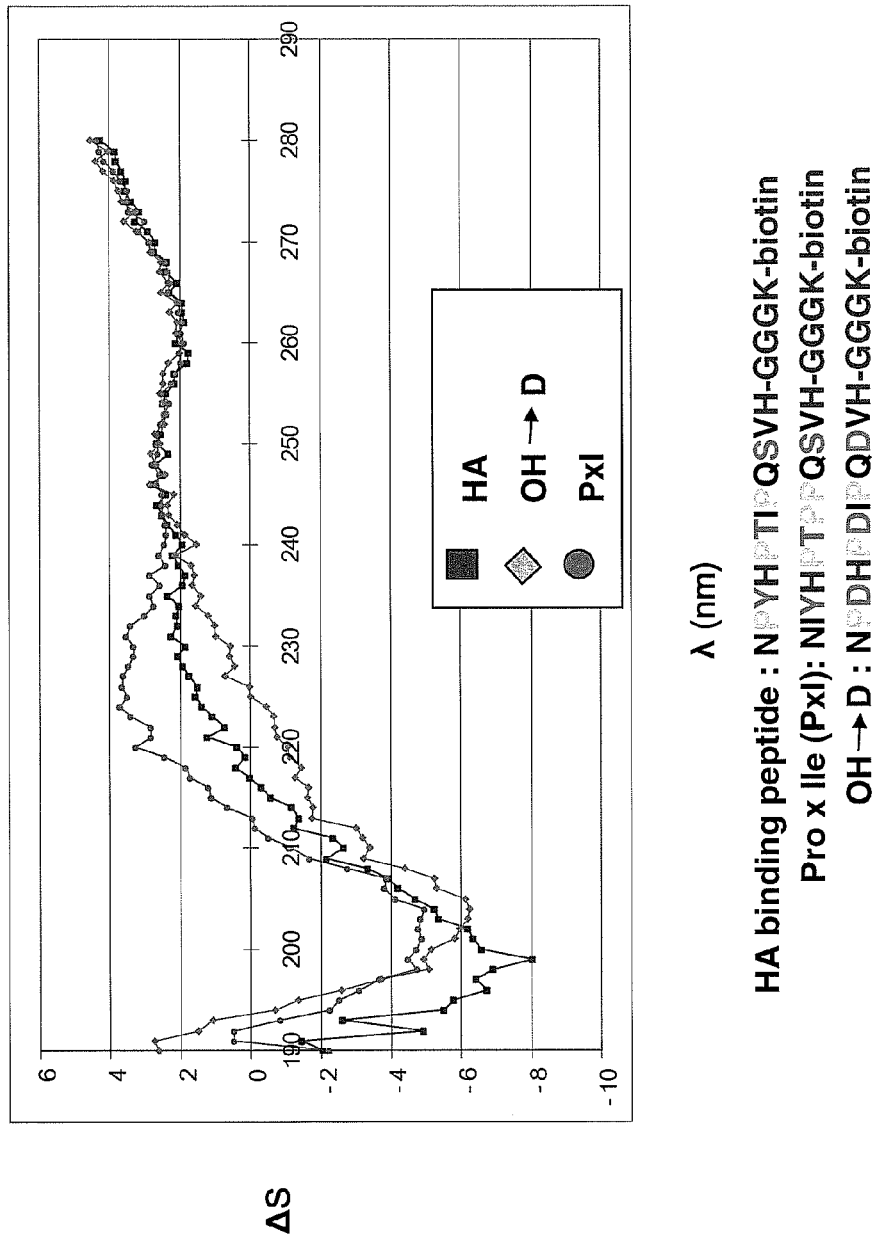

The term "homology" or "homologous" herein refers to an amino acid sequence similarity measured by the program, BLAST (Altschul et al (1997), "Gapped BLAST and PSI-BLAST: a new generation of protein database search programs", Nucleic Acids Res. 25:3389-3402 and expressed as −(% identity n/n). In measuring homology between a peptide and a peptide or protein of greater size, homology is measured only in the corresponding region; that is, the protein is regarded as only having the same general length as the peptide, allowing for gaps and insertions using default values. The term "homologous" herein refers to a percent homology of at least 20%, more preferably 40%, even more preferably 70%, up to 85%, 90%, 91%, 92%, 93%, 94%, 95%, 96%, 97%, 98%, 99%, 99.5%, 99.8%, and 99.9% homology. The term "substantially homologous" herein refers to a percent homology of at least 40%, more preferably 70%, even more preferably 85%, up to 91%, 92%, 93%, 95%, 96%, 97%, 98%, 99%, 99.5%, 99.8%, and 99.9% homology.

The term "mineral" herein refers to any inorganic compound, comprised of inorganic elements, including but not limited to, $Ca^{2+}$, $PO_4^{3-}$, $OH^-$, $CO_3^{2-}$, $Cl^-$ and other trace inorganic elements. The inorganic compound can include, but are not limited to, such compounds as crystalline, nanocrystalline or amorphous HA ($Ca_{10}(PO_4)_6(OH)_2$), calcium carbonate, and calcium phosphates with solubility behavior, under acidic and basic conditions, similar to that of HA, including but not limited to dicalcium phosphate, tricalcium phosphate, octacalcium phosphate or calcium phosphates having a stoichiometry that ranges from $CaO\text{-}2P_2O_5$ to $4CaO\text{-}P_2O_5$, with a definite composition and definite crystalline, nanocrystalline or amorphous structure.

The term "mineralization" herein refers to integration of inorganic components onto a peptide or into a peptide-containing scaffold.

The term "scaffold" herein refers to a three-dimensional polymeric structure with mineral-binding peptides or masked mineral-binding sites along the polymer for mineral or other bone mineral attachment.

The term "nanocrystalline" herein refers to a mineral formation that is lengths-scale from 1000 nm to 1 nm which can be either crystalline or amorphous deposits.

The term "single crystalline" herein refers to solid phase materials characterized by an absence of crystal boundaries and by a uniform atomic structural arrangement. The term also includes materials composed of oriented-crystals or enlarged crystals (when the enlarged crystals are used as though they are a single-crystal or when the enlarged crystals are used individually as single-crystals).

The term "polycrystalline" herein refers to materials composed of variously oriented, and usually a large number of, small individual crystals or crystallites The term "nucleation" herein refers to the first step of mineralization where the inorganic anions or cations are attracted or recruited to the peptides or peptide-containing three-dimensional scaffolds.

The terms "binding activity" or "ability to bind" are herein meant to describe the measure of the binding or affinity of molecules to each other.

Figure 10:
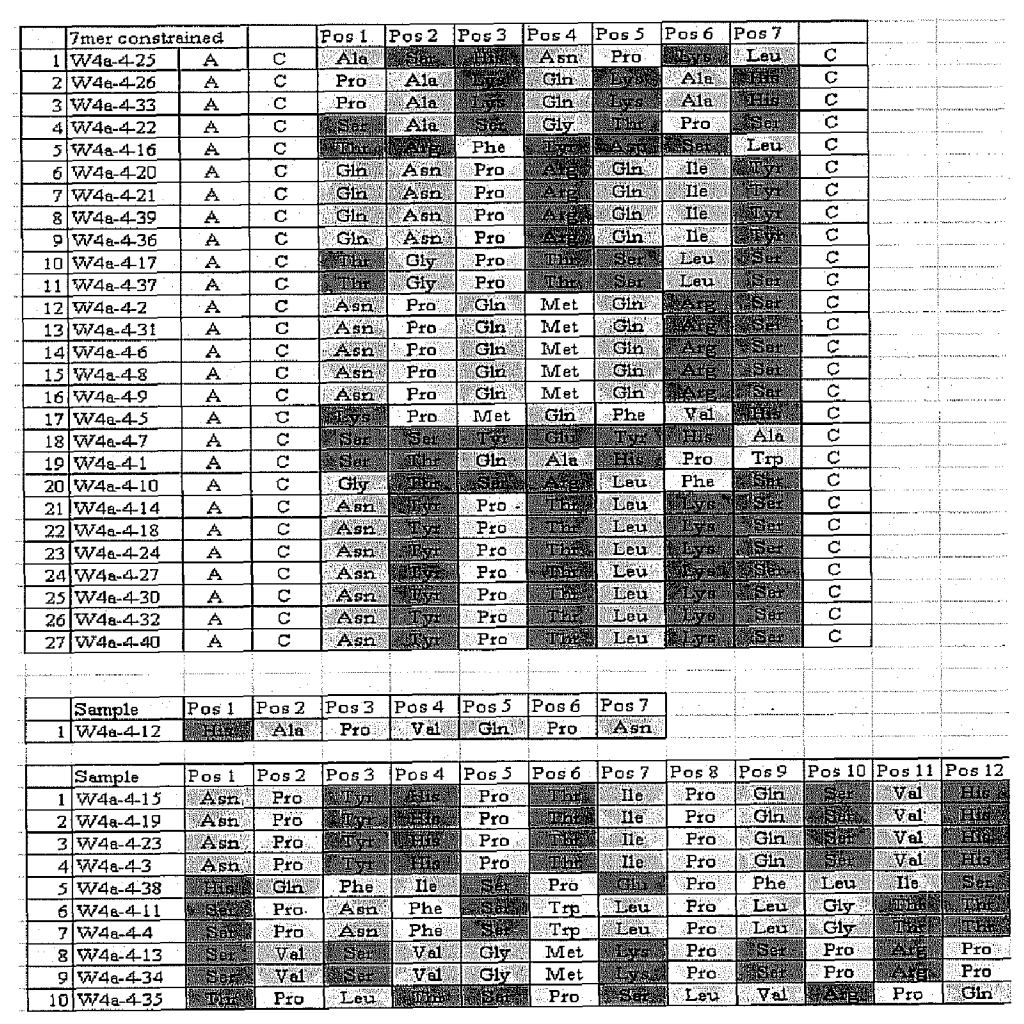

In one embodiment of the present invention, novel short specific binding peptide motifs against single crystalline or polycrystalline HA surfaces were identified by phage display. Phage display was conducted and is schematically shown in FIG. 1, Panel A. An M13 phage combinatorial library was allowed to interact with HA crystals to allow peptides to bind to the HA crystals. Bound phages were pH eluted from the HA particles by incubation. Next the bound phages were enriched by bacteria by growth in *E. coli* for 4.5 hours to enrich the sequences to about $10^6$ copies. The viruses were separated and purified. The eluted phage was titered to count the number of the viruses eluted and to analyze the virus DNA sequences. After purifying amplified phage suspension using polyethylene glycol precipitation, the enriched phage suspension was used to repeat the next round of the biopanning process with much harsher elution condition than the previous round. Successive rounds of screening were performed to enrich the binding sequences. The sequences and peptide motifs identified as having binding activity to HA are shown below (SEQ ID NOS: 1-267) and in tables in FIGS. 7-11.

The peptide motifs described herein can be exploited as templates to grow HA, the major inorganic component of natural bone and teeth. In one embodiment, sequences were identified which contained periodic proline-hydroxylamino acid binding sequences similar to the Gly-Pro-Hyp (Hyp: hydroxyproline) repeats of human type I collagen, which is generally believed to provide spatial guidance for the growth of bone biominerals. Synthesized short binding peptides were further used as a template to grow HA crystals.

Figure 5:
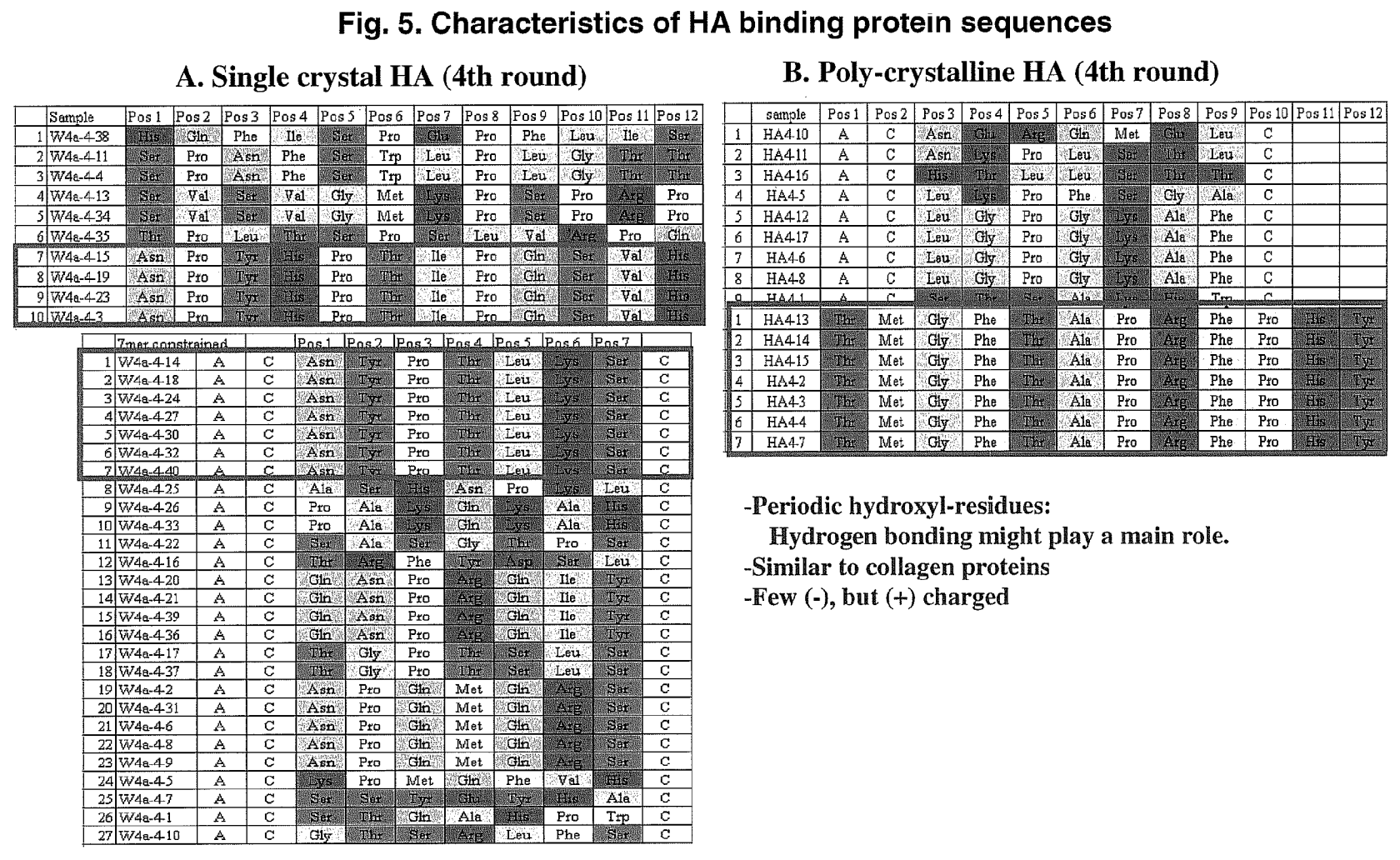

Referring to FIG. 5, peptides were identified as strong binders of HA in both single crystalline HA and poly-crystalline HA. The sequences from the fourth rounds of screening are shown with preferred sequences shown in the bold box. Positively charged residues include histidine, arginine and lysine. Negatively charged residues include glutamic acid and aspartic acid. Hydrophobic residues include leucine, isoleucine, glycine, alanine, and valine. Amide (side chain)-containing residues include asparagines and glutamine. Hydroxyl-containing residues include tyrosine, threonine and serine. Proline provides rigidity in three-dimensional structures. Aromatic residues include phenylalanine and tryptophan. Methionine and cysteine, capable of forming disulfide bonds, were placed in each of their own categories.

In one embodiment, it is contemplated that sequences can be made which are substantially identical to the peptides (SEQ ID NOS: 1-267) listed herein, but still retain the essential HA-binding activity exhibited by the peptides described herein. Thus, in one embodiment, the invention provides for a peptide that binds HA, having a length of 5-15 amino acid residues, wherein the peptide comprises (1) at least one amino acid residue having a hydroxyl side chain, wherein if there is more than one residue having a hydroxyl side chain, that another residue having a hydroxyl side chain occurs every 2-7 residues; and (2) at least one positively-charged residue. In another embodiment, the peptide further comprises (3) at least one residue having an amide side chain. Furthermore, in one preferred embodiment, the distances between the alpha carbons of at least two hydroxylated or amide (side-chain)-containing amino acid residues should closely match the lattice parameters of HA of 9.42 Å, to within at least 0.5 to 2.5 Å. In another preferred embodiment, the distances between the oxygens of at least two hydroxylated amino acid residues closely matches unit cell distance of single crystal HA on (100) face (9.42 Å) and/or the average distance between neighboring hydroxyproline (Hyp, O) residues (10.10±0.84 Å) in a collagen-like peptide (1CAG, SEQ ID NO: 268, having the sequence, POGPOGPOGPOGPOAPOGPOG-POGPOGPOG (P=Pro, O=Hydroxyproline, G=Gly)), to within at least 0.5 to 2.5 Å. The crystal and molecular structure of this collagen-like peptide was characterized to 1.9 Å resolution by J. Bella, M. Eaton, B. Brodsky, H. M. Berman, *Science* 266, 75 (1994).

In another embodiment, it is further contemplated that substantially identical peptides can be made to each of the disclosed peptides from each round of selection by systematically making conserved substitutions. For example, using the color-coding in FIG. 5, it is contemplated that any residue listed in the same category may be used interchangeably with any other residue in the same category. Therefore, peptides having substituted residues can be generated based on the color-coding of the disclosed peptides.

In another embodiment, homologous peptides to any of the peptides of the invention having a percent homology of at least 20%, more preferably at least 40%, even more preferably at least 70%, more preferably up to 85%, most preferably at least 93% homologous, while retaining HA-binding activity. In a preferred embodiment, substantially homologous peptides share a percent homology of at least 40%, more preferably 70%, even more preferably 85%, up to 91%, 92%, 93%, 94%, 95%, 96%, 97%, 98%, 99%, 99.5%, 99.8%, and 99.9% homology, to any of the disclosed peptide sequences and having the ability to bind HA.

In another embodiment, it is further contemplated that the peptides of the invention may be flanked by other amino acids such as cysteines, histidines or glycines, or amino acid sequence which does not destroy or interfere with the HA-binding or nucleation activity of the peptides. For example, the peptides can be constrained and flanked by cysteines on both ends, such as the constrained Single 14 peptide, SEQ ID NO: 267. In another embodiment, the peptides can be attached to biomolecules or materials for binding, labeling or identification including biotin, streptavidin, oligonucleotides, other known sequence, antibodies, nanoparticles, nanocrystals, nanospheres, polyethylene glycols, lipids, biomolecules, and the like. It is further contemplated that the peptides can be attached to the biomolecules through means of linking molecules or flanking amino acid sequence. In one embodiment, the peptides are linked to biotin through means of a linking amino acid sequence, GGGK, thereby producing a peptide having a sequence such as Control Peptide 1, NPY-HPTIPQSVH-GGGK-biotin (SEQ ID NO: 269).

The functional binding activity of HA-binding peptides of the invention can be illustrated in several assays, for example the method used in Example 2. Any peptide shown by flow cytometry to have a relative intensity of fluorescence above the background is said to have mineral or HA-binding activity.

One main characteristic of the HA-binding peptides of the invention is the periodic display of the hydroxyl or amide (side chain) residues. Most of the 7-mer binding peptides identified (22 out of 27) have pseudo-repetitive consensus amino acid sequences possessing periodic hydroxyl side chains at approximately every two to three residues. In addition, when the dominant 7-mer binding sequences are compared with those of the 12-mers, key amino acid patterns were found to be highly conserved. Specifically, Asn, Tyr, Pro, Thr, Leu and Ser appeared at positions 1, 2, 3, 4, 5, and 7 in the 7-mer constrained binding peptides; these residues also appeared at positions 1, 3, 5, 6, 7, and 10, respectively, in the 12-mer linear binding peptides.

Another characteristic of the 12-mer dominant binding sequences is periodic occurrence of proline and hydroxyl/amide (side chain) residues. These pseudo-repetitive sequences resembled the (Gly-Pro-Hyp)$_n$ repeat of human type I collagen, a major component of the extracellular matrices of natural bone.

For example, the most dominant 12-mer binding peptide (NPYHPTIPQSVH, SEQ ID NO: 208) emerged after the fourth round of screening showing the periodic display of prolines (position 2, 5, and 8) and hydroxylated residues (position 3, 6 and 10). Compared with dominant 7-mer constrained binding peptide (CNYPTLKSC, SEQ ID NO: 267; two cysteines form a disulfide bond) isolated under the same experimental conditions, both dominant binding peptides exhibited remarkable conserved amino acid sequences (Asn, Tyr, Pro, Thr, Ile/Leu, and Ser). Considering the lack of hydroxyproline residue in the phage libraries, the sequence similarity between the isolated peptide and the most frequent GPO (Gly-Pro-Hyp) repeat of type I collagen is rather striking. Type I collagen is believed to guide controlled growth of HA in natural bone. Therefore the fact that the single 15 peptide was identified via directed evolutionary screening processes from billions of candidates suggests that the presence of a collagen-like binding peptide motif in the present peptides imparts specific recognition of single crystal HA surfaces.

In addition, these binding peptide sequences tended to possess positively charged residues rather than negatively charged residues. Up till now, the negatively charged groups found in many acidic non-collagenous ECM proteins have been postulated to be important in regulating the biomineralization process in natural bone. Favorable electrostatic interactions between the positively charged residues and the negatively charged HA surfaces under physiological pH (pH 7.5) may be a driving force.

It is known that many ECM proteins in calcified tissues (e.g. sialoprotein, phosphophoryn, amelogenin) are rich in phosphoserine, aspartate, and glutamate residues. These negatively charged residues may be involved in enriching local calcium ions and templating the nucleation of amorphous minerals and their subsequent ripening into more stable crystalline structures.

In addition, it is found that when the sequences are similar, 7-mer constrained viruses generally exhibit better binding affinity than the linear peptides, presumably due to the lack of the structural flexibility. Titering experiments in Example 2 and the results shown in FIG. 12 (single 14 is 7-mer constrained vs. single 15 is 12-mer) also showed similar trends (supporting information) for the binding specificity against HA.

In our phage display against single crystal HA, the a and b faces of the whisker type HA (FIG. 3) was targeted to combinatorial screening. Binding amino acids sequences were found to contain periodic hydroxyl and amide (side chain) residues. For the HA-binding peptides identified in the 12-mer linear type library, hydroxyl/amide (side chain) residues were often coupled with a proline residue, which lends rigidity to peptide helical structure. This pairing is reminiscent of the major repeating sequences in type I collagen of Glycine-Proline-Hydroxyproline repeating sequences which are critical in collagen-HA interaction in human bone formation. It may be that hydrogen bonding between the hydroxyl/amide (side chain) residues and the phosphate group in HA is the major driving force for the binding interaction. This result may decipher the role of the Gly-Pro-Hyp repeating sequences in the collagen-HA interaction in human bone formation.

The peptides of the invention are listed herein according to the round of phage display selection that the peptide was identified. The 7-mer peptides, recited herein and selected from constrained 7-mer libraries, were flanked on both ends by cysteine residues. The cysteines are shown in the Figures. The asterisks in place of residues at various positions in the peptides below indicate that any residue may be placed at the position.

TABLE 1

FIRST ROUND (against single crystal HA)

| SEQ ID NO: | Clone | Sequence |
|---|---|---|
| SEQ ID NO: 1 | W4A-1-22 | Arg Pro His Thr Ile Thr Asn |
| SEQ ID NO: 2 | W4A-1-17 | Gln Ser Ser Tyr Asn Pro Ile |
| SEQ ID NO: 3 | W4A-1-25 | Gln Thr His Ala Arg His Gln |
| SEQ ID NO: 4 | W4A-1-21 | Glu Thr Arg Thr Gln Leu Leu |
| SEQ ID NO: 5 | W4A-1-29 | His His Gln Arg Ser Pro Ala |
| SEQ ID NO: 6 | W4A-1-20 | Leu Gln Lys Ser Pro Ser Leu |
| SEQ ID NO: 7 | W4A-1-4 | Pro Pro Lys Asp Ser Arg Gly |
| SEQ ID NO: 8 | W4A-1-19 | Ser Ala Lys Lys Val Phe Ser |
| SEQ ID NO: 9 | W4A-1-24 | Ser Gln His Ser Thr Gln Asp |
| SEQ ID NO: 10 | W4A-1-27 | Thr Ile His Ser Lys Pro Ala |
| SEQ ID NO: 11 | W4A-1-8 | Thr Lys Asp Trp Leu Pro Ser |
| SEQ ID NO: 12 | W4A-1-10 | Ala Asn Pro Pro Leu Ser Leu |
| SEQ ID NO: 13 | W4A-1-9 | Ala Lys Gln Thr Val Pro Val |
| SEQ ID NO: 14 | W4A-1-15 | Ala Thr Phe Ser Pro Pro Leu |
| SEQ ID NO: 15 | W4A-1-5 | Asp Gln Tyr Trp Gly Leu Arg |
| SEQ ID NO: 16 | W4A-1-14 | Glu Pro Asn His Thr Arg Phe |
| SEQ ID NO: 17 | W4A-1-18 | His Met Leu Ala Gln Thr Phe |
| SEQ ID NO: 18 | W4A-1-12 | Ile Gly Tyr Pro Val Leu Pro |
| SEQ ID NO: 19 | W4A-1-31 | Lys Leu Ser Ala Trp Ser Phe |
| SEQ ID NO: 20 | W4A-1-11 | Met Tyr Pro Leu Pro Ala Pro |
| SEQ ID NO: 21 | W4A-1-6 | Phe Thr Leu Pro Thr Ile Arg |
| SEQ ID NO: 22 | W4A-1-16 | Ser Met Ala Ala Lys Ser Ser |
| SEQ ID NO: 23 | W4A-1-1 | Ser Met Tyr Asp Thr His Ser |
| SEQ ID NO: 24 | W4A-1-32 | Ser Thr Leu Ala Ser Met Arg |
| SEQ ID NO: 25 | W4A-1-23 | Thr Leu Met Thr Thr Pro Pro |
| SEQ ID NO: 26 | W4A-1-13 | Trp Leu Pro Pro Arg Thr Gln |
| SEQ ID NO: 27 | W4A-1-2 | Arg Thr Pro Leu Gln Pro Leu Glu Asp Phe Arg Pro |
| SEQ ID NO: 28 | W4A-1-7 | Asn Thr Thr Asp Ile Pro Ser Gln Phe |
| SEQ ID NO: 29 | W4A-1-3 | Thr Leu Asp Lys Tyr Thr Arg Leu Leu Ser Arg Tyr |
| SEQ ID NO: 30 | W4A-1-28 | Tyr Pro Ile Met Ser His Thr Cys Cys His Gly Val |

SECOND ROUND (against single crystal HA)

| SEQ ID NO: | Clone | Sequence |
|---|---|---|
| SEQ ID NO: 31 | W4-2-31 | Tyr Glu Pro Ala Ala Ala Glu |
| SEQ ID NO: 32 | W4-2-18 | Ala Asn Pro Tyr His Arg His |
| SEQ ID NO: 33 | W4-2-26 | Ala Ser Gly Pro Thr Asn Val |
| SEQ ID NO: 34 | W4-2-39 | Gln Asn Tyr Leu Leu Pro Lys |
| SEQ ID NO: 35 | W4-2-28 | Gly Thr Gln Thr Pro Gln Pro |
| SEQ ID NO: 36 | W4-2-20 | His Ser Thr Gly Pro Thr Arg |
| SEQ ID NO: 37 | W4-2-32 | Leu Ser Lys Asn Pro Leu Leu |
| SEQ ID NO: 38 | W4-2-34 | Leu Ser Lys Asn Pro Leu Leu |
| SEQ ID NO: 39 | W4-2-14 | Lys Leu His Ala Ser Leu Ala |
| SEQ ID NO: 40 | W4-2-3 | Pro Leu Thr Gln Pro Ser His |
| SEQ ID NO: 41 | W4-2-5 | Pro His Asn Pro Gly Lys Leu |
| SEQ ID NO: 42 | W4-2-9 | Pro Thr Thr Met Thr Arg Trp |
| SEQ ID NO: 43 | W4-2-23 | Val His Leu Thr His Gly Gln |
| SEQ ID NO: 44 | W4-2-12 | Thr Leu Ala Pro Thr Phe Arg |
| SEQ ID NO: 45 | W4-2-4 | Val His Pro Arg Pro Ser Leu |
| SEQ ID NO: 46 | W4-2-19 | Thr Leu Leu Arg Thr Gln Val |
| SEQ ID NO: 47 | W4-2-2 | Ser Ser Pro Pro Arg Val Tyr |
| SEQ ID NO: 48 | W4-2-17 | Ser Ser Val Pro Gly Arg Pro |
| SEQ ID NO: 49 | W4-2-37 | Leu Pro Phe Gln Pro Pro Ile |
| SEQ ID NO: 50 | W4-2-8 | Ile Gln His Gln Ala Lys Thr |
| SEQ ID NO: 51 | W4-2-33 | Leu Pro Arg Asp Leu His Ala Thr Pro Gln Gln Ile |
| SEQ ID NO: 52 | W4-2-35 | Leu Thr Pro Thr Met Phe Asn Met His Gly Val Leu |
| SEQ ID NO: 53 | W4-2-11 | Ser Ile Pro Lys Met Ile Pro Thr Glu Ser Leu Leu |
| SEQ ID NO: 54 | W4-2-6 | Ser Phe Gln Ser Met Ser Leu Met Thr Leu Val Val |
| SEQ ID NO: 55 | W4-2-15 | Thr Gln Thr Trp Pro Gln Ser Ser Ser His Gly Leu |
| SEQ ID NO: 56 | W4-2-29 | Tyr Glu Leu Gln Met Pro Leu Thr Leu Pro Leu Asn |
| SEQ ID NO: 57 | W4-2-10 | Ala Met Ser Gln Thr Met Thr Ala Ala Ile Glu Lys |
| SEQ ID NO: 58 | W4-2-7 | Gly Ser Ala Gly Leu Lys Tyr Pro Leu Tyr Lys Ser |
| SEQ ID NO: 59 | W4-2-30 | Ile Asn Phe Gln Phe Leu Lys Pro Ser Thr Thr Arg |
| SEQ ID NO: 60 | W4A-2-19 | Arg His Thr Leu Pro Leu His |
| SEQ ID NO: 61 | W4A-2-18 | Asn Phe Ala Met Asn Leu Arg |
| SEQ ID NO: 62 | W4A-2-29 | Asn Phe Ala Met Asn Leu Arg |
| SEQ ID NO: 63 | W4A-2-15 | Asn Pro Gln Met Gln Arg Ser |
| SEQ ID NO: 64 | W4A-2-24 | Asn Pro Gln Met Gln Arg Ser |
| SEQ ID NO: 65 | W4A-2-32 | Asn Pro Gln Met Gln Arg Ser |
| SEQ ID NO: 66 | W4A-2-13 | Asn Tyr Pro Thr Leu Lys Ser |
| SEQ ID NO: 67 | W4A-2-27 | Asn Tyr Pro Thr Leu Lys Ser |
| SEQ ID NO: 68 | W4A-2-11 | Gln Asn Pro Arg Gln Ile Tyr |
| SEQ ID NO: 69 | W4A-2-20 | Gln Asn Pro Arg Gln Ile Tyr |
| SEQ ID NO: 70 | W4A-2-3 | Gln Asn Pro Arg Gln Ile Tyr |
| SEQ ID NO: 71 | W4A-2-6 | Gln Asn Pro Arg Gln Ile Tyr |
| SEQ ID NO: 72 | W4A-2-22 | Glu Thr Tyr Ala Arg Pro Leu |
| SEQ ID NO: 73 | W4A-2-25 | Glu Thr Val Cys Ala Ser Ser |
| SEQ ID NO: 74 | W4A-2-14 | Lys Pro Met Gln Phe Val His |
| SEQ ID NO: 75 | W4A-2-23 | Lys Pro Met Gln Phe Val His |
| SEQ ID NO: 76 | W4A-2-2 | Pro Ala Lys Gln Lys Ala His |
| SEQ ID NO: 77 | W4A-2-26 | Pro Thr Thr Trp Gly His TABLE 1-continued

| SEQ ID NO: | Clone | Sequence |
|---|---|---|
| SEQ ID NO: 78 | W4A-2-4 | Pro Thr Thr Trp Gly His Leu |
| SEQ ID NO: 79 | W4A-2-7 | Ser Ala Ser Gly Thr Pro Ser |
| SEQ ID NO: 80 | W4A-2-17 | Ser Ser Tyr Glu Tyr His Ala |
| SEQ ID NO: 81 | W4A-2-9 | Ser Ser Tyr Glu Tyr His Ala |
| SEQ ID NO: 82 | W4A-2-30 | Ser Thr Gln Ala His Pro Trp |
| SEQ ID NO: 83 | W4A-2-21 | Thr Val Leu Gly Thr Phe Pro |
| SEQ ID NO: 84 | W4A-2-8 | Trp Tyr Pro Asn His Leu Ala |
| SEQ ID NO: 85 | W4A-2-1 | Thr Thr Tyr Asn Ser Pro Pro |
| SEQ ID NO: 86 | W4A-2-5 | Met Thr Ser Gln Thr Leu Arg |
| SEQ ID NO: 87 | W4A-2-12 | Trp Pro Ala Asn Lys Leu Ser Thr Lys Ser Met Tyr |
| SEQ ID NO: 88 | W4A-2-28 | Trp Pro Ala Asn Lys Leu Ser Thr Lys Ser Met Tyr |
| SEQ ID NO: 89 | W4A-2-31 | Asn Pro Tyr His Pro Thr Ile Pro Gln Ser Val His |

THIRD ROUND (against single crystal HA)

| SEQ ID NO: | Clone | Sequence |
|---|---|---|
| SEQ ID NO: 90 | W4-3-22 | Asp Lys Leu His Arg Leu Ala |
| SEQ ID NO: 91 | W4-3-38 | Gln Pro Gly Leu Trp Pro Ser |
| SEQ ID NO: 92 | W4-3-13 | Glu Ser Leu Lys Ser Ile Ser |
| SEQ ID NO: 93 | W4-3-25 | Gly Ser Cys Pro Pro Lys Lys |
| SEQ ID NO: 94 | W4-3-1 | Gly Ser Leu Phe Lys Ala Leu |
| SEQ ID NO: 95 | W4-3-23 | His Gln Trp Asp His Lys Tyr |
| SEQ ID NO: 96 | W4-3-14 | Leu Ser Ala Pro Met Glu Tyr |
| SEQ ID NO: 97 | W4-3-40 | Met Lys Val His Glu Arg Ser |
| SEQ ID NO: 98 | W4-3-5 | Phe Val Asn Leu Leu Gly Gln |
| SEQ ID NO: 99 | W4-3-15 | Pro Ile Asp Ala Phe Phe Asp |
| SEQ ID NO: 100 | W4-3-29 | Pro Pro Asn Met Ala Arg Ala |
| SEQ ID NO: 101 | W4-3-32 | Pro Thr Asn Lys Pro His Thr |
| SEQ ID NO: 102 | W4-3-4 | Ser Pro Asn Asn Thr Arg Glu |
| SEQ ID NO: 103 | W4-3-34 | Ser Pro Glu Met Lys Pro Arg |
| SEQ ID NO: 104 | W4-3-30 | Ser Ser Ser Met Ala Lys Met |
| SEQ ID NO: 105 | W4-3-17 | Thr Asp His Pro Pro Lys Ala |
| SEQ ID NO: 106 | W4-3-37 | Thr Leu Ala Phe Gln Thr Ala |
| SEQ ID NO: 107 | W4-3-16 | Ala Pro Leu Ser Leu Ser Leu |
| SEQ ID NO: 108 | W4-3-7 | His Tyr Pro Thr Val Asn Phe |
| SEQ ID NO: 109 | W4-3-39 | Gln His Asn Phe Arg Gly Ala Ser Ser Ala Pro |
| SEQ ID NO: 110 | W4-3-36 | His Gln Phe Pro X Ser Asn Leu Val Trp Lys Pro (X = Arg or Pro) |
| SEQ ID NO: 111 | W4-3-31 | Leu Ser Leu Arg Ala Ser Ala Ala Thr Asp Phe Gln |
| SEQ ID NO: 112 | W4-3-24 | Met Gln Phe Thr Pro Ala Pro Ser Pro Ser Asp His |
| SEQ ID NO: 113 | W4-3-27 | Ser Val Phe Leu Pro Thr Arg His Ser Pro Asp Leu |
| SEQ ID NO: 114 | W4-3-20 | Ser Val Ser Val Gly Met Lys Pro Ser Pro Arg Pro |
| SEQ ID NO: 115 | W4-3-3 | Ser Val Ser Val Gly Met Lys Pro Ser Pro Arg Pro |
| SEQ ID NO: 116 | W4-3-8 | Ser Val Ser Val Gly Met Lys Pro Ser Pro Arg Pro |
| SEQ ID NO: 117 | W4-3-28 | Ser Val Ser Val Gly Met Lys Pro Ser Pro Arg Pro |
| SEQ ID NO: 118 | W4-3-35 | Ser Val Ser Val Gly Met Asn Ala Glu Ser * Ala |
| SEQ ID NO: 119 | W4a-3-20 | Arg His Thr Leu Pro Leu His |
| SEQ ID NO: 120 | W4a-3-1 | Asn Pro Gln Met Gln Arg Ser |
| SEQ ID NO: 121 | W4a-3-38 | Asn Tyr Pro Thr Leu Lys Ser |
| SEQ ID NO: 122 | W4a-3-40 | Asn Tyr Pro Thr Leu Lys Ser |
| SEQ ID NO: 123 | W4a-3-24 | Asp Met Arg Gln Gln Arg Ser |
| SEQ ID NO: 124 | W4a-3-14 | Gln Asn Pro Arg Gln Ile Tyr |
| SEQ ID NO: 125 | W4a-3-18 | Gln Asn Pro Arg Gln Ile Tyr |
| SEQ ID NO: 126 | W4a-3-21 | Gln Asn Pro Arg Gln Ile Tyr |
| SEQ ID NO: 127 | W4a-3-22 | Gln Asn Pro Arg Gln Ile Tyr |
| SEQ ID NO: 128 | W4a-3-27 | Gln Asn Pro Arg Gln Ile Tyr |
| SEQ ID NO: 129 | W4a-3-31 | Gln Asn Pro Arg Gln Ile Tyr |
| SEQ ID NO: 130 | W4a-3-32 | Gln Asn Pro Arg Gln Ile Tyr |
| SEQ ID NO: 131 | W4a-3-39 | Gln Asn Pro Arg Gln Ile Tyr |
| SEQ ID NO: 132 | W4a-3-4 | Gln Asn Pro Arg Gln Ile Tyr |
| SEQ ID NO: 133 | W4a-3-6 | Gln Thr His Ser Ser Leu Trp |
| SEQ ID NO: 134 | W4a-3-3 | Glu Thr Tyr Gln Gln Pro Leu |
| SEQ ID NO: 135 | W4a-3-30 | Glu Thr Tyr Ala Arg Pro Leu |
| SEQ ID NO: 136 | W4a-3-35 | Gly Thr Ser Arg Leu Phe Ser |
| SEQ ID NO: 137 | W4a-3-34 | Leu Thr Gln Thr Leu Gln Tyr |
| SEQ ID NO: 138 | W4a-3-23 | Lys Ala Phe Asp Lys His Gly |
| SEQ ID NO: 139 | W4a-3-16 | Lys Pro Met Gln Phe Val His |
| SEQ ID NO: 140 | W4a-3-29 | Lys Pro Met Gln Phe Val His |
| SEQ ID NO: 141 | W4a-3-37 | Lys Pro Met Gln Phe Val His |
| SEQ ID NO: 142 | W4a-3-19 | Pro Ala Lys Gln Lys Ala His |
| SEQ ID NO: 143 | W4a-3-33 | Ser Ala Ser Gly Thr Pro Ser |
| SEQ ID NO: 144 | W4a-3-2 | Ser Ser His His His Arg His |
| SEQ ID NO: 145 | W4a-3-28 | Ser Ser Tyr Glu Tyr His Ala |
| SEQ ID NO: 146 | W4a-3-26 | Thr Gly Pro Thr Ser Leu Ser |
| SEQ ID NO: 147 | W4a-3-36 | Leu Arg Ala Phe Pro Ser Leu Pro His Thr Val Thr |

FOURTH ROUND (against single crystal HA)

| SEQ ID NO: | Clone | Sequence |
|---|---|---|
| SEQ ID NO: 148 | W4-4-9 | Asn Pro Arg Ser Gln Ala Thr |
| SEQ ID NO: 149 | W4-4-25 | His Arg Leu Gly His Met Ser |
| SEQ ID NO: 150 | W4-4-7 | Leu Leu Pro Leu Lys Phe Lys |
| SEQ ID NO: 151 | W4-4-24 | Leu Pro Ser Ile His Asn Leu |
| SEQ ID NO: 152 | W4-4-40 | Lys Ala Thr Ile Thr Gly Met |
| SEQ ID NO: 153 | W4-4-35 | Pro Asp Ile Pro Leu Ser Arg |

TABLE 1-continued

| SEQ ID NO: | Name | Sequence |
|---|---|---|
| SEQ ID NO: 154 | W4-4-5 | Pro Ser Met Lys His Trp Arg |
| SEQ ID NO: 155 | W4-4-13 | Ser Ala Lys Gly Arg Ala Asp |
| SEQ ID NO: 156 | W4-4-6 | Ser Arg Thr Gly Ala His His |
| SEQ ID NO: 157 | W4-4-1 | Ser Lys Thr Ser Ser Thr Ser |
| SEQ ID NO: 158 | W4-4-20 | Ser Pro Asn Asn Pro Arg Glu |
| SEQ ID NO: 159 | W4-4-31 | Thr Leu Gln Arg Met Gly Gln |
| SEQ ID NO: 160 | W4-4-4 | Thr Met Thr Asn Met Ala Lys |
| SEQ ID NO: 161 | W4-4-19 | Thr Thr Leu Ser Pro Arg Thr |
| SEQ ID NO: 162 | W4-4-22 | Thr Thr Lys Asn Phe Asn Lys |
| SEQ ID NO: 163 | W4-4-23 | Tyr Pro Lys Ala Leu Arg Asn |
| SEQ ID NO: 164 | W4-4-29 | Val Val Lys Ser Asn Gly Glu |
| SEQ ID NO: 165 | W4-4-38 | * Ile Thr * Gly Ala Tyr |
| SEQ ID NO: 166 | W4-4-21 | Leu Pro Leu Thr Pro Leu Pro |
| SEQ ID NO: 167 | W4-4-2 | His Ser Met Pro His Met Gly Thr Tyr Leu Leu Thr |
| SEQ ID NO: 168 | W4-4-14 | Met Gln Phe Thr Pro Ala Pro Ser Pro Ser Asp His |
| SEQ ID NO: 169 | W4-4-12 | Met Pro Gln Thr Leu Val Leu Pro Arg Ser Leu Leu |
| SEQ ID NO: 170 | W4-4-17 | Ser Ser Thr Gln Val Gln His Thr Leu Leu Gln Thr |
| SEQ ID NO: 171 | W4-4-18 | Ser Trp Pro Leu Tyr Ser Arg Asp Ser Gly Leu Gly |
| SEQ ID NO: 172 | W4-4-26 | Ser Val Ser Val Gly Thr Glu Ala Glu Ser * Ala |
| SEQ ID NO: 173 | W4-4-28 | Ser Val Ser Val Gly Met Lys Pro Ser Pro Arg Pro |
| SEQ ID NO: 174 | W4-4-30 | Ser Val Ser Val Gly Met Lys Pro Ser Pro Arg Pro |
| SEQ ID NO: 175 | W4-4-37 | Ser Val Ser Val Gly Met Lys Pro Ser Pro Arg Pro |
| SEQ ID NO: 176 | W4-4-32 | Ser Val Ser Val Gly Met Asn Ala Glu Ser Tyr Gly |
| SEQ ID NO: 177 | W4-4-33 | Thr His Pro Val Val Phe Glu Asp Glu Arg Leu Phe |
| SEQ ID NO: 178 | W4-4-8 | Thr Leu Pro Ser Pro Leu Ala Leu Leu Thr Val His |
| SEQ ID NO: 179 | W4-4-34 | Trp Pro Thr Tyr Leu Asn Pro Ser Ser Leu Lys Ala |
| SEQ ID NO: 180 | W4a-4-25 | Ala Ser His Asn Pro Lys Leu |
| SEQ ID NO: 181 | W4a-4-26 | Pro Ala Lys Gln Lys Ala His |
| SEQ ID NO: 182 | W4a-4-33 | Pro Ala Lys Gln Lys Ala His |
| SEQ ID NO: 183 | W4a-4-22 | Ser Ala Ser Gly Thr Pro Ser |
| SEQ ID NO: 184 | W4a-4-16 | Thr Arg Phe Tyr Asp Ser Leu |
| SEQ ID NO: 185 | W4a-4-20 | Gln Asn Pro Arg Gln Ile Tyr |
| SEQ ID NO: 186 | W4a-4-21 | Gln Asn Pro Arg Gln Ile Tyr |
| SEQ ID NO: 187 | W4a-4-39 | Gln Asn Pro Arg Gln Ile Tyr |
| SEQ ID NO: 188 | W4a-4-36 | Gln Asn Pro Arg Gln Ile Tyr |
| SEQ ID NO: 189 | W4a-4-17 | Thr Gly Pro Thr Ser Leu Ser |
| SEQ ID NO: 190 | W4a-4-37 | Thr Gly Pro Thr Ser Leu Ser |
| SEQ ID NO: 191 | W4a-4-2 | Asn Pro Gln Met Gln Arg Ser |
| SEQ ID NO: 192 | W4a-4-31 | Asn Pro Gln Met Gln Arg Ser |
| SEQ ID NO: 193 | W4a-4-6 | Asn Pro Gln Met Gln Arg Ser |
| SEQ ID NO: 194 | W4a-4-8 | Asn Pro Gln Met Gln Arg Ser |
| SEQ ID NO: 195 | W4a-4-9 | Asn Pro Gln Met Gln Arg Ser |
| SEQ ID NO: 196 | W4a-4-5 | Lys Pro Met Gln Phe Val His |
| SEQ ID NO: 197 | W4a-4-7 | Ser Ser Tyr Glu Tyr His Ala |
| SEQ ID NO: 198 | W4a-4-1 | Ser Thr Gln Ala His Pro Trp |
| SEQ ID NO: 199 | W4a-4-10 | Gly Thr Ser Arg Leu Phe Ser |
| SEQ ID NO: 200 | W4a-4-14 | Asn Tyr Pro Thr Leu Lys Ser Single 14 |
| SEQ ID NO: 201 | W4a-4-18 | Asn Tyr Pro Thr Leu Lys Ser |
| SEQ ID NO: 202 | W4a-4-24 | Asn Tyr Pro Thr Leu Lys Ser |
| SEQ ID NO: 203 | W4a-4-27 | Asn Tyr Pro Thr Leu Lys Ser |
| SEQ ID NO: 204 | W4a-4-30 | Asn Tyr Pro Thr Leu Lys Ser |
| SEQ ID NO: 205 | W4a-4-32 | Asn Tyr Pro Thr Leu Lys Ser |
| SEQ ID NO: 206 | W4a-4-40 | Asn Tyr Pro Thr Leu Lys Ser |
| SEQ ID NO: 207 | W4a-4-12 | His Ala Pro Val Gln Pro Asn |
| SEQ ID NO: 208 | W4a-4-15 | Asn Pro Tyr His Pro Thr Ile Pro Gln Ser Val His Single 15 |
| SEQ ID NO: 209 | W4a-4-19 | Asn Pro Tyr His Pro Thr Ile Pro Gln Ser Val His |
| SEQ ID NO: 210 | W4a-4-23 | Asn Pro Tyr His Pro Thr Ile Pro Gln Ser Val His |
| SEQ ID NO: 211 | W4a-4-3 | Asn Pro Tyr His Pro Thr Ile Pro Gln Ser Val His |
| SEQ ID NO: 212 | W4a-4-38 | His Gln Phe Ile Ser Pro Glu Pro Phe Leu Ile Ser |
| SEQ ID NO: 213 | W4a-4-11 | Ser Pro Asn Phe Ser Trp Leu Pro Leu Gly Thr Thr |
| SEQ ID NO: 214 | W4a-4-4 | Ser Pro Asn Phe Ser Trp Leu Pro Leu Gly Thr Thr |
| SEQ ID NO: 215 | W4a-4-13 | Ser Val Ser Val Gly Met Lys Pro Ser Pro Arg Pro |
| SEQ ID NO: 216 | W4a-4-34 | Ser Val Ser Val Gly Met Lys Pro Ser Pro Arg Pro |
| SEQ ID NO: 217 | W4a-4-35 | Thr Pro Leu Thr Ser Pro Ser Leu Val Arg Pro Gln |
| SEQ ID NO: 218 | | Thr Pro Leu Ser Tyr Leu Lys Gly Leu Val Thr Val |

FIRST ROUND (against polycrystalline HA)

| SEQ ID NO: | Name | Sequence |
|---|---|---|
| SEQ ID NO: 219 | HA-2-16 | Asn Pro Met Ile Met Asn Gln |
| SEQ ID NO: 220 | HA-2-30 | Asn Pro Met Ile Met Asn Gln |
| SEQ ID NO: 221 | HA-2-7 | Asn Ile Thr Gln Leu Gly Ser |
| SEQ ID NO: 222 | HA-2-1 | His Thr Leu Leu Ser Thr Thr |
| SEQ ID NO: 223 | HA-2-27 | His Thr Leu Leu Ser Thr Thr |
| SEQ ID NO: 224 | HA-2-6 | His Thr Leu Leu Ser Thr Thr |
| SEQ ID NO: 225 | HA-2-21 | Leu Gly Pro Gly Lys Ala Phe |
| SEQ ID NO: 226 | HA-2-25 | Leu Gly Pro Gly Lys Ala Phe |
| SEQ ID NO: 227 | HA-2-3 | Leu Gly Pro Gly Lys Ala Phe |
| SEQ ID NO: 228 | HA-2-4 | Leu Gly Pro Gly Lys Ala Phe |
| SEQ ID NO: 229 | HA-2-22 | Lys Thr Ser Ser Trp Ala Asn |
| SEQ ID NO: 230 | HA-2-29 | Lys Met Asn His Met Pro Asn |
| SEQ ID NO: 231 | HA-2-12 | Ser Leu Leu Thr Pro Trp Leu |

TABLE 1-continued

| SEQ ID NO: | Name | Sequence |
|---|---|---|
| SEQ ID NO: 232 | HA-2-20 | Thr Leu Gly Leu Pro Met Leu |
| SEQ ID NO: 233 | HA-2-32 | Thr Gly Leu Ala Lys Thr Ala |
| SEQ ID NO: 234 | HA-2-35 | Ile Arg * Leu * Ile Ser |
| SEQ ID NO: 235 | HA-2-18 | Leu Gly Pro Gly Lys Ala Phe |
| SEQ ID NO: 236 | HA-2-2 | Leu Gly Pro Gly Lys Ala Phe |
| SEQ ID NO: 237 | HA-2-28 | Leu Gly Pro Gly Lys Ala Phe |

SECOND ROUND (against polycrystalline HA)

| SEQ ID NO: 238 | HA-2-14 | Asp Leu Asn Tyr Phe Thr Leu Ser Ser Lys Arg Glu |
| SEQ ID NO: 239 | HA-2-15 | Asp Leu Asn Tyr Phe Thr Leu Ser Ser Lys Arg Glu |
| SEQ ID NO: 240 | HA-2-19 | Thr Met Gly Phe Thr Ala Pro Arg Phe Pro His Tyr |
| SEQ ID NO: 241 | HA-2-26 | Thr Met Gly Phe Thr Ala Pro Arg Phe Pro His Tyr |
| SEQ ID NO: 242 | HA-2-31 | Thr Met Gly Phe Thr Ala Pro Arg Phe Pro His Tyr |
| SEQ ID NO: 243 | HA-2-8 | Thr Met Gly Phe Thr Ala Pro Arg Phe Pro His Tyr |

THIRD ROUND (against polycrystalline HA)

| SEQ ID NO: 244 | HA3-4 | His Thr Leu Leu Ser Thr Thr |
| SEQ ID NO: 245 | HA3-7 | His Thr Leu Leu Ser Thr Thr |
| SEQ ID NO: 246 | HA3-3 | Leu Ala Ser Thr Thr His Val |
| SEQ ID NO: 247 | HA3-2 | Leu Gly Pro Gly Lys Ala Phe |
| SEQ ID NO: 248 | HA3-5 | Leu Gly Pro Gly Lys Ala Phe |
| SEQ ID NO: 249 | HA3-8 | Leu Gly Pro Gly Lys Ala Phe |
| SEQ ID NO: 250 | HA3-6 | Ser Leu Leu Thr Pro Trp Leu |

FOURTH ROUND (against polycrystalline HA)

| SEQ ID NO: 251 | HA4-10 | Asn-Glu-Arg-Gln-Met-Glu-Leu |
| SEQ ID NO: 252 | HA4-11 | Asn-Lys-Pro-Leu-Ser-Thr-Leu |
| SEQ ID NO: 253 | HA4-16 | His-Thr-Leu-Leu-Ser-Thr-Thr |
| SEQ ID NO: 254 | HA4-5 | Leu-Lys-Pro-Phe-Ser-Gly-Ala |
| SEQ ID NO: 255 | HA4-12 | Leu-Gly-Pro-Gly-Lys-Ala-Phe |
| SEQ ID NO: 256 | HA4-17 | Leu-Gly-Pro-Gly-Lys-Ala-Phe |
| SEQ ID NO: 257 | HA4-6 | Leu-Gly-Pro-Gly-Lys-Ala-Phe |
| SEQ ID NO: 258 | HA4-8 | Leu-Gly-Pro-Gly-Lys-Ala-Phe |
| SEQ ID NO: 259 | HA4-1 | Ser-Thr-Ser-Ala-Lys-His-Trp |
| SEQ ID NO: 260 | HA4-13 | Thr-Met-Gly-Phe-Thr-Ala-Pro-Arg-Phe-Pro-His-Tyr |
| SEQ ID NO: 261 | HA4-14 | Thr-Met-Gly-Phe-Thr-Ala-Pro-Arg-Phe-Pro-His-Tyr |
| SEQ ID NO: 262 | HA4-15 | Thr-Met-Gly-Phe-Thr-Ala-Pro-Arg-Phe-Pro-His-Tyr |
| SEQ ID NO: 263 | HA4-2 | Thr-Met-Gly-Phe-Thr-Ala-Pro-Arg-Phe-Pro-His-Tyr |
| SEQ ID NO: 264 | HA4-3 | Thr-Met-Gly-Phe-Thr-Ala-Pro-Arg-Phe-Pro-His-Tyr Poly 3 |
| SEQ ID NO: 265 | HA4-4 | Thr-Met-Gly-Phe-Thr-Ala-Pro-Arg-Phe-Pro-His-Tyr |
| SEQ ID NO: 266 | HA4-7 | Thr-Met-Gly-Phe-Thr-Ala-Pro-Arg-Phe-Pro-His-Tyr |
| SEQ ID NO: 267 | W4a-4-14 | Cys Asn Tyr Pro Thr Leu Lys Ser Cys Constrained Single 14 |

Other sequences

| SEQ ID NO: 268 | | 1CAG POG POG POG POG POG POA POG POG POG POG POG POG (O = 4hydroxyproline) |
| SEQ ID NO: 269 | | NPYHPTIPQSVH-GGGK-biotin Control peptide 1 |
| SEQ ID NO: 270 | | NPDHPDIPQDVH-GGGK-biotin Control peptide 2 |
| SEQ ID NO: 271 | | NPYHPTIPQSVH-GGGK-biotin Control peptide 3 |
| SEQ ID NO: 272 | | NPYAPTIPQSVA-GGGK-biotin Control peptide 4 |
| SEQ ID NO: 273 | | APYHPTIPASVH-GGGK-biotin Control peptide 5 |

The peptides may be made and purified by methods known in the art, preferably by in vitro automated synthesis, but also by recombinant DNA methods. Furthermore, these peptides can be synthesized using D- or L-amino acids and selected non-natural or other modified amino acids, as is known in the art, in order to synthesize peptides which can act upon targets in the body and be degraded if necessary, yet do not interfere with normal protein function. The peptides can be stored in lyophilized form and dissolved in aqueous buffers or water prior to use. For the purposes of experimental use, the peptides can be dissolved in sterilized water or buffer. In addition, suitable buffers or diluents should be capable of solubilizing the active peptide, preferably at a suitable pH to prevent the peptide from precipitating out of solution too easily.

In one embodiment, the invention further contemplates the use of the peptides tagged with detectable agents including, but not limited to, antibodies, radioanalogs, products or compounds having distinctive absorption, fluorescence, or chemiluminescence properties, such as rhodamine, fluorescein, green fluorescent protein (GFP) or semiconductor nanocrystal beads. Peptides tagged with such detectable agents would be useful for studying and monitoring the peptides and their effectiveness in templated nucleation of HA.

One embodiment of the present invention involves preparing a library of HA-binding peptides for use with complex solutions and mixtures of minerals to create HA on a surface material. Because of the HA-binding activity of the present peptides, they may be immobilized on soluble or insoluble solid, bulk or polymeric scaffolds or matrices. It is contemplated that the HA-binding peptides can be attached covalently or non-covalently, including physical adsorption, to biomolecules or biomaterials, either organic, inorganic or organic-inorganic composites.

Examples of such polymeric scaffolds include using the monomers and co-monomers disclosed in U.S. Pat. Application Pub. No. 2004/0161444, filed on Dec. 18, 2003, which is hereby incorporated by reference in its entirety. It is contemplated that the peptides of the invention can be attached to co-monomers in the formation of such polymeric scaffolds to be displayed on the scaffolds to promote mineralization. Furthermore, it is contemplated that the peptides of the invention can be used in conjunction with other known peptides or agents in the art for the promotion of mineralization. For example, Bab, et al., in U.S. Pat. No. 6,479,460, and Rodan, et al., in U.S. Pat. No. 5,461,034, which are hereby incorporated by reference in their entirety, disclose synthetic peptides, pseudopeptides, and pharmaceutical compositions having osteogenic activity which can be attached to the co-monomers as functional groups to make the biomimetic composites. Different co-monomers may also be used to control porosity, the concentration of nucleation sites, and other properties.

In another aspect, the scaffold can be coated with at least one material such as gold, avidin, streptavidin, carboxymethyl groups, dextran or collagen to promote the stable attachment of the peptide to the scaffold. In one embodiment, the scaffold is coated with streptavidin and the peptide is biotinylated, whereby the peptide attaches to the scaffold through the binding of biotin and the streptavidin-coating.

In one embodiment, the peptide is attached to the scaffold by means of an oligonucleotide. In this embodiment, the oligonucleotide is biotinylated and attaches to the scaffold through the binding of biotin and the streptavidin-coating. In one aspect, the peptide would further comprise flanking amino acid sequences. In another aspect, the invention further comprises a peptide or protein bound to the peptide by means of a polyhistidine tag.

These HA-binding peptides are expected to be further incorporated into three dimensional organic matrices or cellular environment to orchestrate and regulate the growth or inhibition of the bone structures. Prokaryotic or eukaryotic cell line can be modified by insertion of the short DNA motifs which can express the HA binding peptides. Structural biology also needs to be considered in this in vivo and ex vivo system to display short peptide motifs outside of cellular membranes.

In one embodiment, osteoblasts can be genetically engineered to express the HA-binding peptides. The engineered osteoblasts can then be applied in cell-based treatments of bone defects such as where there is deficient bone growth. The display of the peptides outside the cellular membranes will direct nucleation and mineral growth to the applied areas.

In another embodiment, the HA-binding peptides can be attached onto a scaffold, such as an artificial bone scaffold implant. If such implant is then inserted into a subject, the peptides would direct nucleation of HA in vivo, thus encouraging the integration of the implant with natural bone. Thus, in practice it is contemplated that an implantable structure be formed in vitro and adapted to fit a particular area of bony structure to be repaired or reconstructed. The peptides can be attached to the scaffold, or attached to a surface on a scaffold. After mineralization, the mineralized structure is implanted into the subject in the recipient site. Alternatively, the peptide coated substrates can be implanted to induce mineralization in vivo. Then, the implant can be attached to the bony structure under physiological conditions, such as the modification or mediation of osteoclasts and osteoblasts which express the HA-binding peptides, as described above.

In addition to the utilization of the HA-binding peptides for biomimetic bone synthesis, it is also possible to exploit the inhibitory potential of these peptides in HA crystal growth where these peptides may be coupled with the nucleation frontline. When these peptides are incorporated with soluble polymer matrices, the HA binding peptides can block the nucleation frontline so that the crystal growth can not be propagated further to form elongated crystals. These peptides can also be coated onto organic and inorganic nanoparticles or nanospheres and injected into areas where the HA-deposition needs to be reduced.

In another embodiment, HA-binding peptides are coated, combined, bound or adsorbed with a pharmaceutically acceptable delivery vehicle and injected into interstitial spaces where HA deposition needs to be reduced. Examples of such pharmaceutically acceptable delivery vehicles includes but are not limited to biopolymers, polymethacrylates, a biodegradable polyester, an aqueous polymeric hydrogel or microgel, nanoparticles or nanospheres.

Example 1

Phage Display to Identify Sequences that Bind to Hydroxyapatite

In order to identify the short peptide specific binding motifs, phage display was performed against the single crystal HA surface. Procedures known in the art were used for phage display. The basic procedure used for phage display selection is schematically shown in FIG. 1, Panel A, which in brief shows, a combinatorial library subjected to biopanning or bioselection after interaction with the target HA crystals, elution, bacterial amplification, DNA analysis and repeating the process for enrichment of sequences that bind the target. The procedures for synthesis of the single crystalline HA crystals are described below. The biopanning procedure is also described in this Example.

The combinatorial library comprises M13 phage having genetically altered proteins featured at the pIII units. Equal amount of three different types of phage library suspensions, 7-mer, 7-mer constrained, 12-mer (Ph.D.-7, Ph.D. c7c, and Ph.D. 12 libraries obtained from New England Biolabs), were mixed to generate more than $6.7 \times 10^9$ diversity of randomized amino acid library and suspended in 10 µl each in 1 mL TBST (0.1%).

Single crystalline hydroxyapatite crystals were incubated with 10 µl of each three library suspensions and then washed with buffer and TWEEN20 in the bioselection step.

Synthesis of single crystalline hydroxyapatite. Single crystalline HA crystal were synthesized by molten salt synthesis, as described in A. Tas, *J. Ame. Ceramic Soc.*, 84, 295 (2001), which is hereby incorporated by reference. The preparation of single crystal hydroxyapatite whiskers was achieved by molten salt synthesis with a potassium sulfate flux at 1190° C. In a typical procedure, commercial polycrystalline HA powders were dry-mixed with potassium sulfate at a $K_2SO_4$-to-HA weight ratio of 1.6. The mixture was placed in a clean alumina crucible and heated in a furnace from room temperature to 1190° C. at a rate of 5° C./min. After holding the temperature at 1190° C. for 3.5 h, the sample was cooled naturally to room temperature within the shut-off furnace. The single crystal HA whiskers were separated from the solidified mass by washing the mass with MilliQ water at 90° C. for three times. The whiskers were then air-dried and characterized by SEM, EDS and XRD. As shown in FIG. 3, the aspect ratios (c:a) of these HA single crystals are in the range of 2-18, with the median whisker diameter and length at 9 mm and 55 mm, respectively. These HA whiskers were monodisperse and were not fused with one another.

To remove potential $CaCO_3$ impurities on HA, HA surfaces were etched using 0.2 M Gly-HCl (pH 2.2) immediately prior to biopanning. This etching condition was also used to elute the bound phage from HA.

Biopanning procedure. 4 mg of single crystal HA particles were etched using glycine-HCl (200 mM, pH 2.2) for overnight and washed six times with Tris-buffered saline (TBS) before the biopanning. The HA crystals were incubated with 10 µl of each three library suspensions (Ph.D 12, Ph.D. 7, and Ph.D. C.7C™, New England Biolab, Mass.) in 1 ml TBST (0.1%) suspension for 30 min with slow rocking. Thereafter, the HA particles were washed 10 times with TBST (0.1%) to wash off all nonbinding phages. The bound phages were eluted from the HA particles by incubation at room temperature in 1 ml of 0-0.2 M glycine-HCl (pH 2.2) for 10 min. The eluted phages were neutralized with 150 µl of 1M TBS (pH 9.1). The eluted phages were amplified with *E. coli* (ER2738) for 4.5 hours in LB medium. Similar biopanning procedures were also performed against commercial polycrystalline HA powders.

The DNA of randomly selected phages was analyzed to identify the peptide expressed on phage pIII units. Selected phage DNA analysis results for each round are shown in the tables of FIG. 7-11. DNA analysis of randomly selected phages from 1$^{st}$ round selection (FIG. 7), 2$^{nd}$ round selection (FIG. 8), 3 round of selection (FIG. 9) and 4$^{th}$ round of selection (FIG. 10) against single crystal HA, as well as from the 4$^{th}$ round selection against the polycrystalline HA (FIG. 11). DNA analysis can be conducted as is known in the art and described in Example 3.

In our phage display against single crystal HA, the a and b faces of the whisker type HA crystals were targeted for combinatorial screening. Binding amino acids sequences were found to systematically contain periodic hydroxyl and amide residues. For the 12-mer linear type library, these hydroxyl/amide side chain residues were also coupled with the rigid proline, reminiscent of the major repeating sequences in type I collagen. After the fourth round of screening, several amino acid sequences resulting from the randomly selected viruses showed more conserved sequences from the 7-mer constrained and 12-mer linear libraries (FIGS. 5 and 6).

Example 2

Binding Affinity of Identified Sequences to Hydroxyapatite

Binding peptides against the polycrystalline HA, which has crystallographically impure surfaces, were also obtained. The selected binding peptide, SEQ ID NO: 264, having the sequence, Tyr-Met-Gly-Phe-Tyr-Ala-Pro-Arg-Phe-Pro-His-Tyr, (Poly 3) was also screened and compared with two single crystalline dominant HA binding sequences named single 14 and 15 using two binding assays. The sequences of the other peptides are Asn-Tyr-Pro-Thr-Leu-Lys-Ser (SEQ ID NO: 200, W4a-4-14, Single 14) and Asn-Pro-Tyr-His-Pro-Thr-Ile-Pro-Gln-Ser-Val-His (SEQ ID NO: 208, W4a-4-15, Single 15) and WILD type phage, which does not have an inserted peptides unit. A constrained single 14 peptide (SEQ ID NO: 267) having two cysteines, one on each end, was used.

As described in Example 1, 4 mg of single crystalline HA was freshly etched to remove carbonated contaminates and incubated with 1×10$^{10}$ pfu of phage of constrained W4a-4-14 (Single 14), W4a-4-15 (single 15), HA-4-3 (poly 3), wild type (wild) phages suspension. After washing off with TBST (0.5%) ten times, the bound phage was eluted using glycine-HCl (mM, pH 2.2) and titered to count number of bound phage. The titering result is shown in FIG. 12, Panel B.

Fluorescence intensity of binding viruses on HA surfaces was measured using flow cytometry (FIG. 12, Panel A). The single 14 phage was shown to bind best to HA surfaces among all viruses tested. Comparing to the wild type viruses, the single 14 phage binds HA almost three times stronger than the other three peptides (FIG. 12, Panel B). Single 15 peptide showed around 50% improved binding affinity (FIG. 12, Panel A). Generally, when peptides have similar binding sequence, constrained peptides have better binding affinity then linear peptide due to the lack of the structural flexibility (M. A. McLafferty, R. B. Kent, R. C. Ladner, W. Markland, *Gene* 15, 29 (1993).). The titer assay counting the phage eluted from the HA surfaces showed similar relative binding affinities against HA (FIG. 12, Panel B).

Correspondingly, HA crystals with bound phage were labeled and imaged by fluorescence. After 30 min incubation of 4 mg/ml of HA crystals with ~10$^{10}$ pfu/ml of phages containing single 14, single 15, poly3, or the wild type phage, which does not have peptide inserts, the phage bound to HA surfaces was labeled using R-phycoerythrin-labeled monoclonal pVIII antibody, and imaged by fluorescence microscope (FIG. 13, right panels of Panels A-C). Considerable amount of fluorescence was observed from single and polycrystalline HA-binding viruses comparing to the wild type viruses (FIG. 13, right panel of Panel D).

After 30 minutes incubation of 4 mg/ml of HA crystals with ~10$^{10}$ pfu/ml of each phage, CLP7, CLP12, or the wild type phages, the HA crystals were washed ten times with Tris-buffered saline solution (pH 7.5) contained 0.5% Tween 20. The phage bound to HA surfaces was labeled by R-phycoerythrin-conjugated monoclonal pVIII antibody (Amersham Pharmacia Biotech, UK), and the fluorescence images were acquired (Nikon fluorescence microscope, Japan) and the fluorescence intensity was quantified by FACS Calibur flow cytometer (BD Biosciences, Calif.).

Example 3

DNA Analysis of Hydroxyapatite-Binding Sequences

Plaque amplification was carried out according to the New England BioLabs, Inc. Ph.D.-12™ Phage Display Peptide Library Kit, Catalog #E8110S, version 2.7, pg. 12-13, as follows: (1) Dilute the ER2738 overnight culture 1:100 in LB. Dispense 1 ml diluted culture into culture tubes, one for each clone to be characterized. 10 clones from the third round are often sufficient to detect a consensus binding sequence. (2) Using a sterile wooden stick or pipet tip, stab a blue plaque and transfer to a tube containing diluted culture. Important: pick plaques from plates having no more than ~100 plaques. This will ensure that each plaque contains a single DNA sequence. (3) Incubate tubes at 37° C. with shaking for 4.5-5 hours (no longer). (4) Optional. In addition to sequencing individual clones, the entire pool of selected phage can be sequenced. This can yield a consensus binding sequence in a single step, but only if the common sequence elements appear in the same positions within the 12-residue "window" in each clone. Add 10 µl of the unamplified eluate to 1 ml diluted overnight culture and incubate at 37° C. with shaking for 4.5-5 hours. (5) Transfer cultures to microcentrifuge tubes, centrifuge 30 seconds. Transfer the supernatant to a fresh tube and re-spin. Using a pipet, transfer the upper 80% of the supernatant to a fresh tube. This is the amplified phage stock and can be stored at 4° C. for several weeks with little loss of titer. For long-term storage, dilute 1:1 with sterile glycerol and store at −20° C.

Rapid purification of sequencing templates. This extremely rapid procedure produces template of sufficient purity for manual or automated dideoxy sequencing, without the use of phenol or chromatography. (1) Carry out the plaque amplification procedure described above. After the first centrifugation step, transfer 500 µl of the phage-containing supernatant to a fresh microfuge tube. (2) Add 200 µl PEG/NaCl. Invert to mix, and let stand at room temperature 10 minutes. (3) Centrifuge 10 minutes, discard supernatant. (4) Re-spin briefly. Carefully pipet away any remaining supernatant. (5) Suspend pellet thoroughly in 100 µl Iodide Buffer and add 250 µl ethanol. Incubate 10 minutes at room temperature. Short incubation at room temperature will preferentially precipitate single-stranded phage DNA, leaving most phage protein in solution. (6) Spin 10 minutes, discard supernatant. Wash pellet in 70% ethanol, dry briefly under vacuum. (7) Suspend pellet in 30 µl TE buffer [10 mM Tris-HCl (pH 8.0), 1 mM EDTA]. (8) 5 µl of the resuspended template should be sufficient for manual dideoxy sequencing with 35S or 33P, or automated cycle sequencing with dye-labeled dideoxynucleotides. More or less template may be required depending on the sequencing method used.

Sequencing of the peptides. Sequencing of the peptides was performed as follows: (1) The −28 primer is recommended for manual dideoxy sequencing. The −96 primer should be used for automated sequencing. (2) The sequence being read corresponds to the anticodon strand of the template. Write out the complementary strand and check against the top strand sequence. Check that the 3rd position of each codon in the randomized region is G or T. Determine the amino acid sequence from this strand 4. (3) TAG stop codons are suppressed by glutamine in ER2738 (supE), the strain originally used to produce the library. TAG should thus be considered a glutamine codon when translating.

Assaying selected peptides for target binding by ELISA. (1) When carrying out the plaque amplification for DNA sequencing, save the remaining phage-containing supernatants at 4° C. (2) For each clone to be characterized, inoculate 20 ml of LB medium with ER2738 and incubate at 37° C. until slightly turbid. Alternatively, dilute an overnight culture of ER2738 1:100 in 20 ml LB. (3) Add 5 µl of phage supernatant to each culture and incubate at 37° C. with vigorous aeration for 4½ hours. (4) Transfer the culture to a centrifuge tube and spin 10 minutes at 10,000 rpm (Sorvall SS-34, Beckman JA-17 or equivalent). Transfer supernatant to a fresh tube and re-spin. (5) Pipet the upper 80% of the supernatant to a fresh tube and add 1/6 volume of PEG/NaCl. Allow phage to precipitate at 4° C. for at least 1 hour or overnight. (6) Spin PEG precipitation 15 minutes at 10,000 rpm at 4° C. Decant supernatant, re-spin briefly, and remove residual supernatant with a pipette. (7) Suspend the pellet in 1 ml TBS. Transfer the suspension to a microcentrifuge tube and spin for 5 minutes at 4° C. to pellet residual cells. (8) Transfer the supernatant to a fresh microcentrifuge tube and re-precipitate with 1/6 volume of PEG/NaCl. Incubate on ice 15-60 minutes. Microcentrifuge for 10 minutes at 4° C. Discard supernatant, re-spin briefly, and remove residual supernatant with a micropipet. (9) Suspend the pellet in 50 µl TBS. Titer as described in Example 2, store at 4° C.

Example 4

Nucleation Ability of Hydroxyapatite-Binding Sequences

Figure 19:
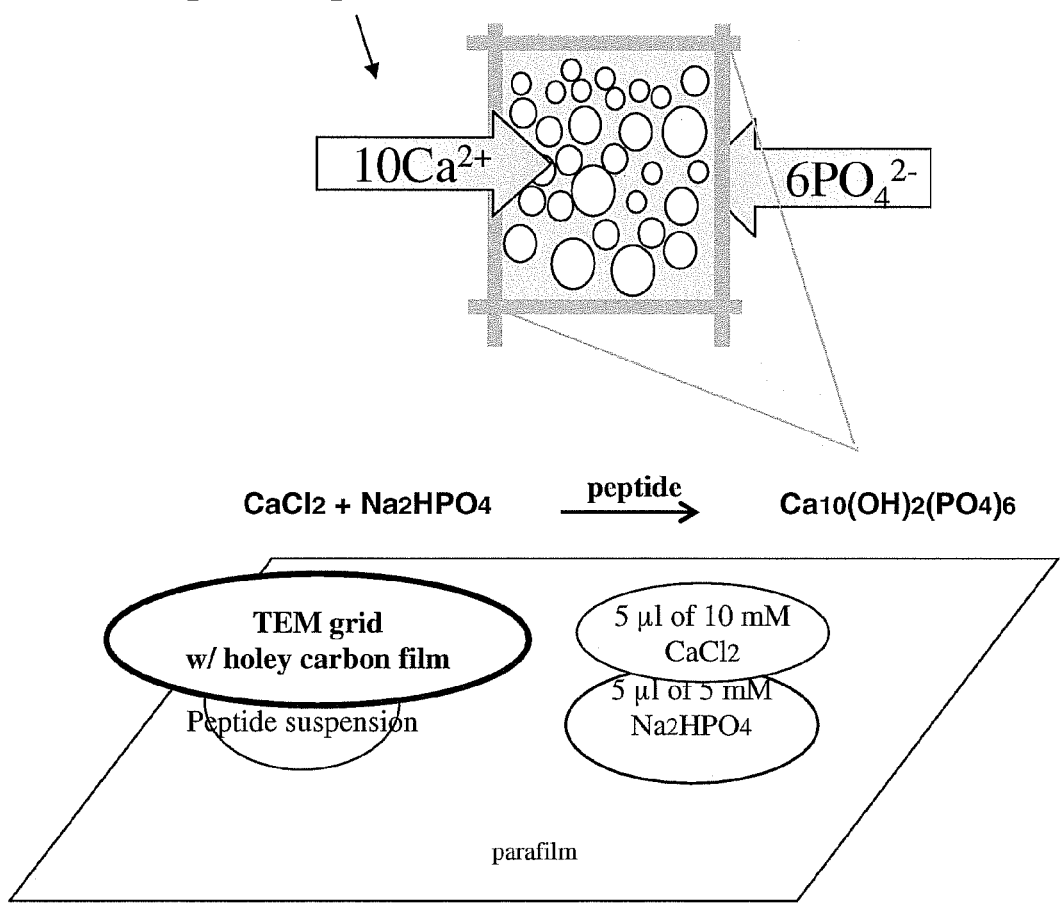

In order to investigate the nucleation ability of these binding peptides, the major 12-mer linear binding peptide was synthesized by solid phase synthetic method and subjected to HA-mineralization on holey carbon film-coated TEM grids according to J. D. Hartgerink, E. Beniash, S. I. Stupp, *Science*, 294, 1684 (2001), which is hereby incorporated by reference. A schematic showing the protocol used is shown in FIGS. 19 and 24.

Figure 20:
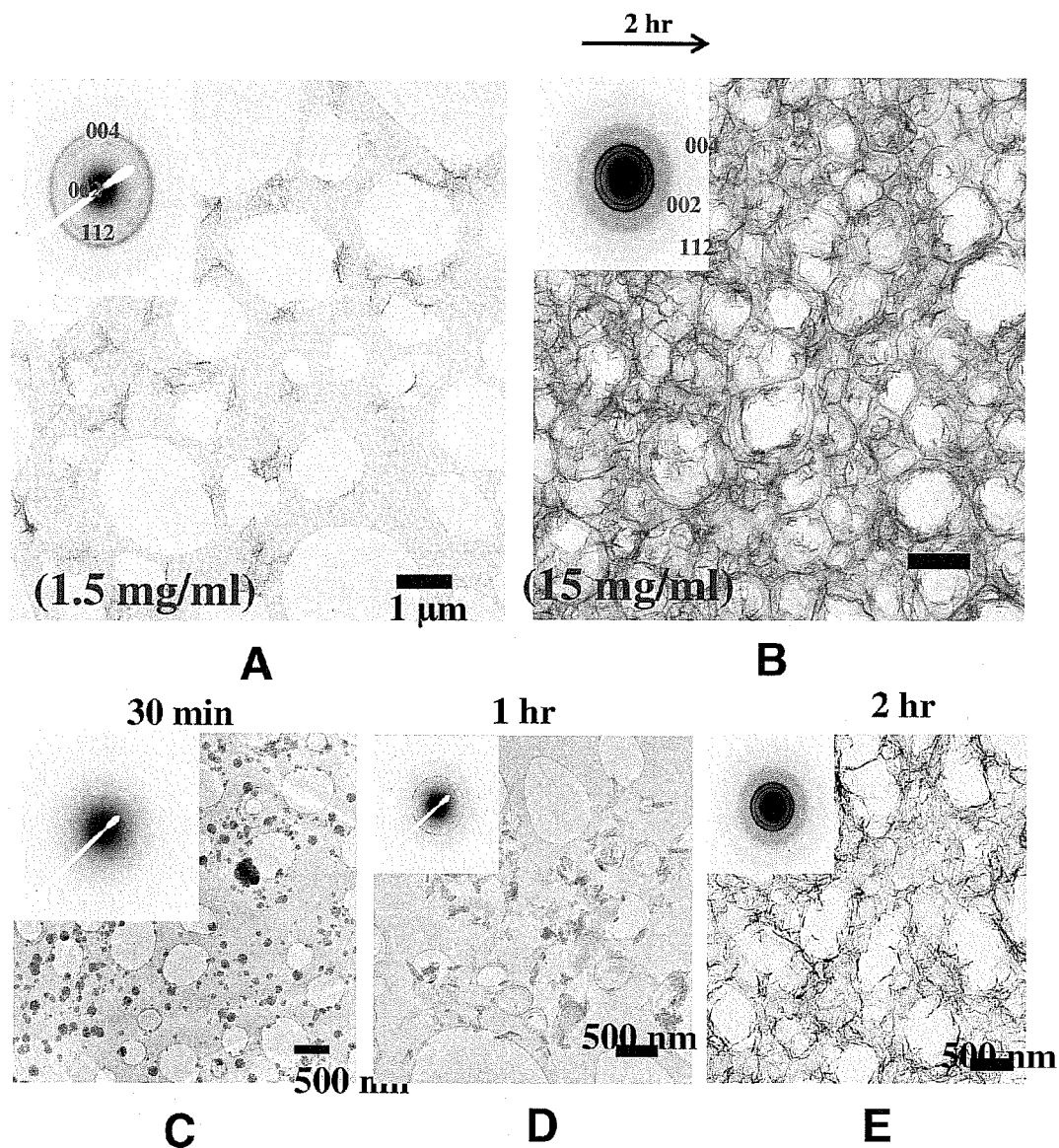

Referring to FIG. 20, Panel A, using the HA-binding peptides identified by phage display, HA crystals can be nucleated. 1.5 mg/ml suspension of peptide NPYHPTIPQSVHGGGK-biotin (single 15-biotin) showed the well crystallized HA deposition. Selected area electron diffraction pattern (SAED) showed the clear polycrystalline ring pattern from (002), (112), and (004) planes. When a ten times higher concentration (15 mg/ml) of the same peptide suspension was applied, well-crystallized HA crystals (FIG. 20, Panel B) covered the entire TEM grids which showed the characteristic SAED patterns for HA, suggesting that the HA deposition depends on the peptide concentration as the same amount of $CaCl_2$ and $Na_2HPO_4$ was used (5 µl of 5 mM $Na_2HPO_4$ and 5 µl of 10 mM $CaCl_2$) for the HA nucleation.

In order to study kinetics of HA nucleation by this peptide suspension, time dependence nucleation was investigated by preparing parallel TEM samples where HA was nucleated for 30 min (FIG. 20, Panel C), 1 hr (FIG. 20, Panel D), and 2 hrs (FIG. 20, Panel E) by same concentration peptide suspension. HA nucleation sample collected after 30 min showed the amorphous deposition of calcium phosphate which showed no clear SAED patterns. After one hour, 50-100 nm sized HA crystals began to be observed as evidenced by the (002) and (112) SAED patterns, with diffraction patterns matching those of crystalline HA (FIG. 20, Panel D). After 2 hours, fully developed HA crystals were nucleated, which covered the entire TEM grids (FIG. 20, Panel E).

Figure 21:
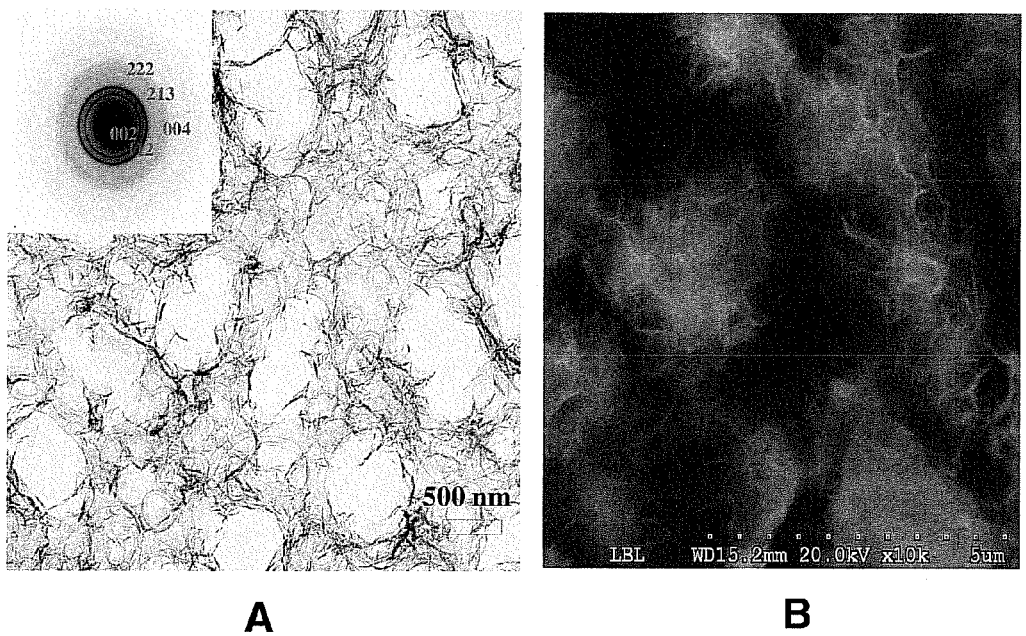
Figure 22:
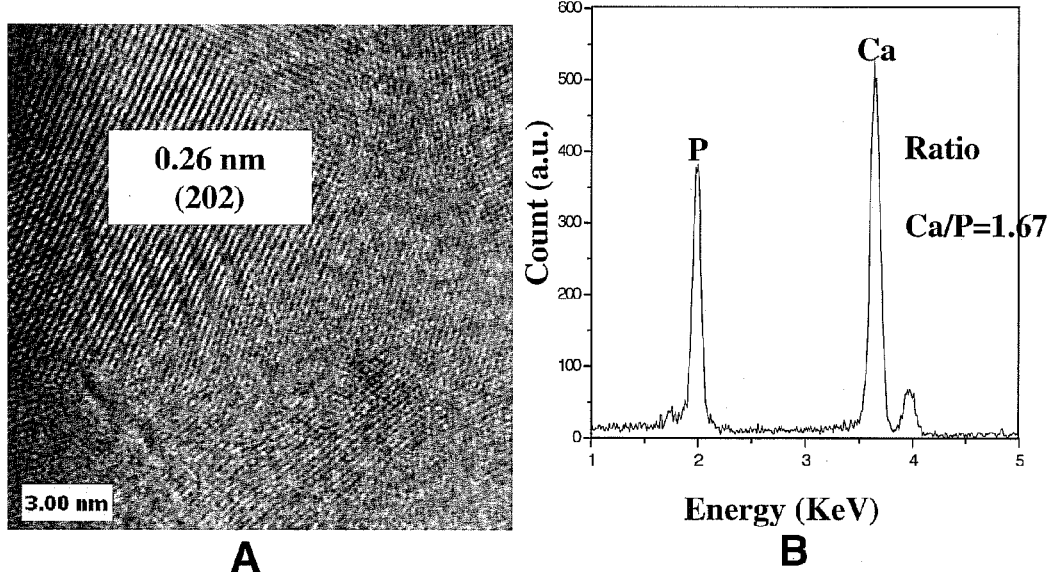

Selected area electron diffraction patterns clearly showed that the crystals are well crystallized yet without a preferred crystal growth orientation (inset in FIG. 20, Panel C). An SEM image of HA-biomineralization templated by the HA-binding 12-mer peptide collected after two hours (FIG. 21, Panel B) was compared to an SEM image of the template. At higher magnification, TEM images revealed that the plate-like HA minerals were composed of ~20 nm HA nanocrystals (FIG. 22).

In high-resolution TEM, the lattice fringe images support that well-crystallized HA was formed. The lattice spacing of the crystals was measured as 0.26 nm, matching the spacing of the (202) face of the HA crystal lattices (FIG. 22, Panel A). Energy dispersive spectroscopy (EDS) measured from the HA crystals showed the Ca/P ratio of 1.67 (FIG. 22, Panel B), matching the theoretical value of the Ca/P ratio of HA. HA nucleation control experiment without HA-binding peptide suspension rarely showed any deposition of calcium phosphate (FIG. 23).

Example 5

Nucleation Ability of Substituted Hydroxyapatite-Binding Sequences

Five control peptides (Table 2) were synthesized and tested to show that single-15-biotin peptide that contains the 12-mer HA binding sequence was not composition specific but sequence-specific to bind and to nucleate HA.

TABLE 2

| Control peptide | Amino acid sequence | SEQ ID NO. |
|---|---|---|
| 1 | NIYHPTPPQSVH-GGGK-biotin | 269 |
| 2 | NPDHPDIPQDVH-GGGK-biotin | 270 |
| 3 | NPYHPTIPQSVH-GGGK-biotin | 271 |
| 4 | NPYAPTIPQSVA-GGGK-biotin | 272 |
| 5 | APYHPTIPASVH-GGGK-biotin | 273 |

Using the same procedure described in Example 4 to template HA growth on holey TEM grids, synthetic peptides not attached to phage were used for a control experiment. FIGS. 24-26 show TEM images of HA growth templated by the variations of the 12-mer HA-binding peptide to show that each specific residue is critical for HA-binding. FIG. 25, Panel A shows nucleation after switching the proline and isoleucine at positions 2 and 7. FIG. 25, Panel B shows nucleation after substituting 3Tyr, 6Thr, and 10Ser with aspartic acid. FIG. 25, Panel C shows nucleation after alanine substitution of the histidines. FIG. 26, Panel A shows nucleation after alanine substitution of 1Asn and 9Gln.

Control experiments of HA nucleation with the scrambled sequence (control peptide 1, SEQ ID NO: 269) by switching proline (from position 2 to 7) and isoleucine (from position 7 to 2) showed amorphous calcium phosphate deposition without any clear SAED patterns. Control peptide 2 (SEQ ID NO: 270) which substituted hydroxyl residue to aspartic acid residue also showed amorphous deposition of calcium phosphate without any clear diffraction patterns within the two hours mineralization time frame.

Control peptides 3-5 which substituted hydroxyl (peptide 3, SEQ ID NO: 271), positively charged (peptide 4, SEQ ID NO: 272), and amide side chain (peptide 5, SEQ ID NO: 273) residues to alanine generally showed low solubility in pure waters. Due to the low solubility of these peptides (control peptides 3, 4 and 5), 1.5 mg/ml peptide suspension in a cosolvent system of acetonitrile and water (1:1/v:v) was prepared and 5 μl of the suspensions were deposited and completely dried in dessicators in a day. When HA crystals were nucleated by soaking the peptide deposited TEM grids into 20 μl of mixture of mineral precursor solutions (10 μl of 5 mM $Na_2HPO_4$ and 10 μl of 10 mM $CaCl_2$), nucleation phenomena similar to those templated by HA binding peptides were observed. When parallel control experiments were conducted using the peptide 3, 4 and 5 solutions in 100% water, control peptides 4 and 5 showed relatively bigger amorphous calcium phosphate aggregation comparing to those templated by peptides 1 and 2, but no well-crystallized crystals were observed. Peptide 3 showed reduced HA-nucleation ability with different morphology of HA crystals (FIG. 25, Panel C). Substitution caused three-dimensional conformational changes of peptides, thereby causing changes in HA surface bonding ability to HA crystals.

Example 6

Characterizing Hydroxyapatite-Binding Sequences

Although negatively charged amino acid residues are thought to be dominant in non-collagenous proteins (e.g. sialoproteins) in bone, (See G. K. Hunter and H. A. Goldberg, *Biochem. J.* 302, 175 (1994); B. L. George, et al., *J. Biol. Chem.* 271, 32869 (1996); and A. Veis, A. Perry, *Biochemistry* 6, 2409 (1967)), the HA-binding peptides identified here possess primarily positively charged residues. This is likely due to the negatively charged surfaces of target HA under physiological screening condition (pH 7.5) (FIG. 7B). Surface charge (zeta potential) of HA whiskers in pH 7.5 buffer was measured using Zetasizer (Malvern Instruments, UK), which gave the value of 11.45±1.49 mV. It is likely that both the hydrogen bonding between the phosphates of HA and the hydroxyl residues of the peptides and the coulombic interaction between negatively charged HA surfaces and the positively charged histidines collectively contribute to the interfacial binding event.

Specific spatial position of each amino acid residue could play an important role in HA-binding as shown by molecular mechanics modeling in FIG. 16, showing that the lattice parameters of HA crystals matching the distances between hydroxylated/amide (side chain) residues of the peptide. Molecular mechanics calculations were performed using the MMFF force field and the analytical Generalized-Born/Surface-Area (GB/SA) solvation model for water implemented in the MacroModel program (Maestro graphical user interface version 6.5.007). Furthermore, the lowest energy conformation of Single 15 peptide (FIG. 17) obtained through molecular mechanics simulation showed that the distances between the oxygens in hydroxyl residues are 10.66 Å ($O_{Ser}$-$O_{Thr}$) and 10.07 Å ($O_{Tyr}$-$O_{Thr}$) closely match with those of the neighboring hydroxyproline residues (10.10±0.84 Å) in collagen (J. Bella, M. Eaton, B. Brodsky, H. M. Berman, *Science* 266 75 (1994)). Referring to FIG. 17, the regularly spaced proline and hydroxyl residues (Tyr, Thr, and Ser, in green) resemble the type I collagen repeating sequence. Considering the flexibility of the O—H bonds of the hydroxyl groups, these distances are commensurate with the unit cell distance of single crystal HA on (100) face (9.42 Å).

The present examples, methods, procedures, treatments, specific peptides, sequences, compounds and molecules are meant to exemplify and illustrate the invention and should in no way be seen as limiting the scope of the invention. Any patents or publications mentioned in this specification are indicative of levels of those skilled in the art to which the patent pertains and are hereby incorporated by reference to the same extent as if each was specifically and individually incorporated by reference for all purposes.

What is claimed is:

1. An implantable bone growth inducing composition comprising a matrix and a peptide having a hydroxyapatite (HA)-binding activity comprising an amino acid sequence having a percent homology of at least 90% with an amino acid sequence selected from the group consisting of SEQ ID NOS: 1-267.

2. The composition of claim 1, wherein the peptide is flanked by a cysteine, histidine or glycine.

3. The composition of claim 1, wherein the peptide is flanked by an amino acid sequence which does not destroy or interfere with the HA-binding activity of the peptide.

4. The composition of claim 1, wherein the HA-binding activity is capable of being shown by flow cytometry to have a relative intensity of fluorescence above the background.

5. The composition of claim 1, wherein the peptide comprises a length of 5-15 amino acid residues.

6. The composition of claim 1, wherein the peptide comprises (a) at least one amino acid residue comprising a hydroxyl side chain, and (b) at least one positively-charged residue.

7. The composition of claim 6, wherein the peptide comprises one amino acid residue comprising a hydroxyl side chain for each 2-7 amino acid residues.

8. The composition of claim 1, wherein the peptide comprises one amino acid residue comprising a hydroxyl side chain for each 2-7 amino acid residues.

9. The composition of claim 1, wherein the peptide comprises the amino acid residues Asn, Tyr, Pro, Thr, Leu and Ser at positions 1, 2, 3, 4, 5, and 7, or positions 1, 3, 5, 6, 7, and 10, respectively.

10. The composition of claim 1, wherein the peptide comprises at least two hydroxylated or amide (side-chain)-containing amino acid residues, and the distance between the alpha carbons of the two hydroxylated or amide (side-chain)-containing amino acid residues, or between the oxygens in hydroxyl groups of the two hydroxylated amino acid residues, closely match the unit cell distance of 9.42 Å in single crystal HA on (100) face to within at least 0.5 to 2.5 Å.

11. The composition of claim 1, wherein the peptide further comprises a nucleation activity.

12. The composition of claim 11, wherein the peptide is flanked by amino acid sequences which do not destroy or interfere with the HA-binding activity and the nucleation activity.

13. The composition of claim 1, further comprising an organic, inorganic or organic-inorganic composite that is attached covalently or non-covalently to the peptide.

14. The composition of claim 1, wherein the peptide comprises an amino acid sequence selected from the group consisting of SEQ ID NOS: 1-267.

15. An implantable bone growth inducing composition comprising: a matrix and at least one amino acid sequence selected from the group consisting of SEQ ID NOs: 1-267, attached thereto.

16. The composition of claim 15, wherein the matrix is selected from the group consisting of ceramics, polymers, bone, demineralized bone, extracellular matrix, and combinations thereof.

17. The composition of claim 16, wherein each of the ceramics comprises calcium phosphate or calcium sulfate.

18. The composition of claim 17, wherein the calcium phosphate is selected from the group consisting of amorphous calcium phosphate, poorly crystalline hydroxyapatite, nanocrystalline hydroxyapatite, stoichiometric hydroxyapatite, calcium deficient hydroxyapatite, substituted hydroxyapatites, tri calcium phosphate, tetracalcium phosphate, dicalcium phosphate dihydrate, and monocalcium phosphate.

19. A method for inhibiting mineral growth in bone, ligament, or cartilage in a mammal comprising administering to said mammal a composition comprising a pharmacologically effective amount of SEQ ID NOS: 1-267 in combination with a pharmaceutically acceptable delivery vehicle.

20. The method of claim 19, wherein the delivery vehicle is polymethacrylate, a biodegradable polyester, an aqueous polymeric gel, a nanoparticle or nanosphere.

21. An osteogenic device for implantation in a mammal, the device comprising: an osteogenic peptide dispersed or attached within a biocompatible, in vivo biodegradable matrix, wherein said osteogenic peptide comprises at least one of the amino acid sequences of SEQ ID NOS: 1-267.

22. The device of claim 21 wherein said matrix comprises a material selected from the group consisting of collagen, hydroxyapatite, tricalcium phosphate, ceramics, biocompatible polymers, extracellular matrix, demineralized bone, and mixtures thereof.

23. A method for directed mineral nucleation or mineralization comprising the steps of: attaching an amino acid sequence to a polymeric organic material to create a mineralized material precursor, wherein the amino acid sequence directs mineralization on the mineralized material precursor, wherein the amino acid sequence has a percent homology of at least 80% with an amino acid sequence selected from the group consisting of SEQ ID NOS: 1-267, wherein the amino acid sequence has a length of 5-15 amino acid residues.

24. The method of claim 23, wherein the amino acid sequence is an amino acid oligomer.

25. The method of claim 23, wherein the amino acid sequence is an amino acid oligomer on the surface of a bacteriophage.

26. The method of claim 23, wherein the amino acid sequence is an amino acid oligomer displayed on the surface of bacteria.

27. The method of claim 23, wherein the amino acid sequence is an amino acid oligomer displayed on the surface of cell as a label.

28. The method of claim 23, wherein the amino acid sequence is selected from a combinatorial library.

29. The method of claim 23, wherein the amino acid sequence is selected from a 7-mer, 7-mer constrained or 12-mer combinatorial library.

30. The method of claim 23, wherein the amino acid sequence comprises amino acid polymers of between about 7 and 15 amino acids.

31. The method of claim 23, wherein the mineralization is polycrystalline.

32. The method of claim 23, wherein the mineralization is single crystalline.

33. The method of claim 23, wherein the polymeric organic material comprises a scaffold.

34. The method of claim 23, wherein the polymeric organic material comprises a three-dimensional polymer.

35. A method for synthesizing an implantable article, comprising the steps of: attaching a biocompatible substrate with a polypeptide having a sequence selected from SEQ ID NOS: 1-267.

36. The composition of claim 1, wherein the matrix is selected from the group consisting of ceramics, polymers, bone, demineralized bone, extracellular matrix, and combinations thereof.

37. The composition of claim 36, wherein each of the ceramics comprises calcium phosphate or calcium sulfate.

38. The composition of claim 37, wherein the calcium phosphate is selected from the group consisting of amorphous calcium phosphate, poorly crystalline hydroxyapatite, nanocrystalline hydroxyapatite, stoichiometric hydroxyapatite, calcium deficient hydroxyapatite, substituted hydroxyapatites, tri calcium phosphate, tetracalcium phosphate, dicalcium phosphate dihydrate, and monocalcium phosphate.

39. A composition comprising a matrix and a peptide having a hydroxyapatite (HA)-binding activity comprising an amino acid sequence having a percent homology of at least 90% with an amino acid sequence selected from the group consisting of SEQ ID NOS: 1-267.

40. The composition of claim 39, wherein the HA-binding activity is capable of being shown by flow cytometry to have a relative intensity of fluorescence above the background.

41. The composition of claim 39, wherein the peptide comprises a length of 5-15 amino acid residues.

42. The composition of claim 39, wherein the peptide comprises (a) at least one amino acid residue comprising a hydroxyl side chain, and (b) at least one positively-charged residue.

43. The composition of claim 42, wherein the peptide comprises one amino acid residue comprising a hydroxyl side chain for each 2-7 amino acid residues.

44. The composition of claim 39, wherein the peptide comprises the amino acid residues Asn, Tyr, Pro, Thr, Leu and Ser at positions 1, 2, 3, 4, 5, and 7, or positions 1, 3, 5, 6, 7, and 10, respectively.

45. The composition of claim 39, wherein the peptide comprises at least two hydroxylated or amide (side-chain)-containing amino acid residues, and the distance between the alpha carbons of the two hydroxylated or amide (side-chain)-containing amino acid residues, or between the oxygens in hydroxyl groups of the two hydroxylated amino acid residues, closely match the unit cell distance of 9.42 Å in single crystal HA on (100) face to within at least 0.5 to 2.5 Å.

46. The composition of claim 39, further comprising an organic, inorganic or organic-inorganic composite that is attached covalently or non-covalently to the peptide.

47. The composition of claim 39, wherein the peptide comprises an amino acid sequence selected from the group consisting of SEQ ID NOS: 1-267.

48. A composition comprising a matrix and a peptide having a hydroxyapatite (HA)-binding activity comprising an amino acid sequence having a percent homology of at least 80% with an amino acid sequence selected from the group consisting of SEQ ID NOS: 1-267, wherein the peptide has a length of 5-15 amino acid residues.

49. The composition of claim 48, wherein the HA-binding activity is capable of being shown by flow cytometry to have a relative intensity of fluorescence above the background.

50. The composition of claim 48, wherein the peptide comprises (a) at least one amino acid residue comprising a hydroxyl side chain, and (b) at least one positively-charged residue.

51. The composition of claim 50, wherein the peptide comprises one amino acid residue comprising a hydroxyl side chain for each 2-7 amino acid residues.

52. The composition of claim 48, wherein the peptide comprises the amino acid residues Asn, Tyr, Pro, Thr, Leu and Ser at positions 1, 2, 3, 4, 5, and 7, or positions 1, 3, 5, 6, 7, and 10, respectively.

53. The composition of claim 48, wherein the peptide comprises at least two hydroxylated or amide (side-chain)-containing amino acid residues, and the distance between the alpha carbons of the two hydroxylated or amide (side-chain)-containing amino acid residues, or between the oxygens in hydroxyl groups of the two hydroxylated amino acid residues, closely match the unit cell distance of 9.42 Å in single crystal HA on (100) face to within at least 0.5 to 2.5 Å.

54. The composition of claim 48, further comprising an organic, inorganic or organic-inorganic composite that is attached covalently or non-covalently to the peptide.

* * * * *